(12) United States Patent
Gottschling et al.

(10) Patent No.: US 8,450,327 B2
(45) Date of Patent: May 28, 2013

(54) CGRP ANTAGONISTS

(75) Inventors: Dirk Gottschling, Mittelbiberach (DE);
Georg Dahmann, Attenweiler (DE);
Henri Doods, Warthausen (DE);
Annekatrin Heimann, Biberach (DE);
Stephan Georg Mueller, Warthausen
(DE); Klaus Rudolf, Warthausen (DE);
Gerhard Schaenzle, Biberach (DE);
Dirk Stenkamp, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 87 days.

(21) Appl. No.: 12/682,853

(22) PCT Filed: Oct. 16, 2008

(86) PCT No.: PCT/EP2008/063967
§ 371 (c)(1),
(2), (4) Date: Jul. 23, 2010

(87) PCT Pub. No.: WO2009/050234
PCT Pub. Date: Apr. 23, 2009

(65) Prior Publication Data
US 2011/0172218 A1 Jul. 14, 2011

(30) Foreign Application Priority Data
Oct. 18, 2007 (EP) .................................... 07118811

(51) Int. Cl.
*A01N 43/54* (2006.01)
*A61K 31/517* (2006.01)
*C07D 239/02* (2006.01)

(52) U.S. Cl.
USPC ............................ 514/258; 544/298; 546/112

(58) Field of Classification Search
USPC .............................. 544/298; 546/112; 514/258
See application file for complete search history.

(56) References Cited

U.S. PATENT DOCUMENTS

| | | |
|---|---|---|
| 8,110,575 B2 | 2/2012 | Gottschling et al. |
| 2007/0099903 A1 | 5/2007 | Mueller et al. |
| 2011/0059954 A1 | 3/2011 | Gottschling et al. |
| 2011/0172218 A1 | 7/2011 | Gottschling et al. |
| 2011/0195954 A1 | 8/2011 | Gottschling et al. |
| 2012/0149698 A1 | 6/2012 | Gottschling et al. |

FOREIGN PATENT DOCUMENTS

| | | |
|---|---|---|
| CA | 2562529 A1 | 10/2005 |
| CA | 2626009 A1 | 4/2007 |
| WO | 9952896 A1 | 10/1999 |
| WO | 0055154 A1 | 9/2000 |
| WO | 0132648 A1 | 5/2001 |
| WO | 0222592 A2 | 3/2002 |
| WO | 03040128 A1 | 5/2003 |
| WO | 2004037810 A1 | 5/2004 |
| WO | 2004037811 A1 | 5/2004 |
| WO | 2005030751 A2 | 4/2005 |
| WO | 2005100343 A1 | 10/2005 |
| WO | 2005100360 A1 | 10/2005 |
| WO | 2005103037 A2 | 11/2005 |
| WO | 2006031513 A2 | 3/2006 |
| WO | 2006100009 A1 | 9/2006 |
| WO | 2006127588 A2 | 11/2006 |
| WO | 2007000340 A2 | 1/2007 |
| WO | 2007045672 A1 | 4/2007 |
| WO | 2008020902 A1 | 2/2008 |
| WO | 2008070014 A2 | 6/2008 |
| WO | 2009034029 A2 | 3/2009 |
| WO | 2009050232 A1 | 4/2009 |

OTHER PUBLICATIONS

International Search Report, Form PCT/ISA/210, for corresponding PCT/EP2008/063967, Date of mailing Jan. 19, 2009.
Doods et al., CGRP antagonists: unravelling the role of CGRP in migraine, TRENDS in Pharmacological Sciences, 2007, vol. 28, No. 11, pp. 580-587.

*Primary Examiner* — Paul V. Ward
(74) *Attorney, Agent, or Firm* — Michael P. Morris; Alan R. Stempel

(57) ABSTRACT

The present invention relates to novel CGRP antagonists of the general formula (I) in which U, V, X, Y, $R^1$, $R^2$, $R^3$ are defined as described below, the tautomers, isomers, diastereomers, enantiomers, hydrates, mixtures and salts thereof, and the hydrates of the salts, particularly the physiologically compatible salts thereof having inorganic or organic acids or bases, pharmaceuticals comprising said compounds, the use thereof, and the method for the production thereof.

23 Claims, No Drawings

CGRP ANTAGONISTS

The present invention relates to new CGRP-antagonists of general formula I

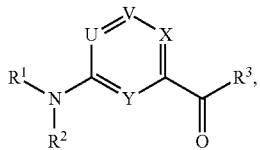

wherein U, V, X, Y, $R^1$, $R^2$ and $R^3$ are defined as stated hereinafter, the tautomers, the isomers, the diastereomers, the enantiomers, the hydrates, the mixtures thereof and the salts thereof and the hydrates of the salts, particularly the physiologically acceptable salts thereof with inorganic or organic acids or bases, pharmaceutical compositions containing these compounds, their use and processes for preparing them.

DETAILED DESCRIPTION OF THE INVENTION

In the above general formula I in a first embodiment
$R^1$ denotes a group of general formula IIa or IIb

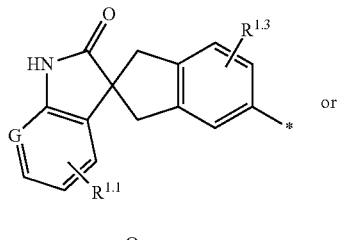

and
$R^2$ denotes H or $C_{1-3}$-alkyl, or
$R^1$ and $R^2$ together with the nitrogen atom to which they are bound denote a group of general formulae IIIa or IIIb

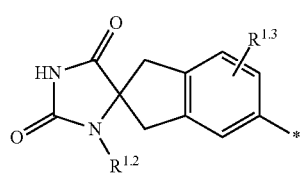

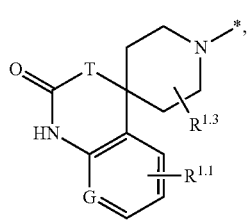

G denotes C—$R^{1.1}$ or N,
T denotes N—$R^{1.2}$ or O,
$R^{1.1}$ independently of one another denote
  (a) H,
  (b) halogen, $C_{1-3}$-alkyl, —OH, —CN, —O—$C_{1-3}$-alkyl, —C(O)—O—$C_{1-3}$-alkyl, $C_{2-4}$-alkenyl, —$C_{2-4}$-alkynyl, $C_{1-3}$-alkyl-S, cyclopropyl, —$NH_2$, —COOH, —NH—C(O)—O—$C_{1-3}$-alkyl, —NH—C(O)—$C_{1-3}$-alkyl,
  (c) a $C_{1-3}$-alkyl group or $C_{1-3}$-alkyl-O— group wherein each methylene group is substituted by up to two fluorine atoms and each methyl group is substituted by up to three fluorine atoms,
$R^{1.2}$ independently of one another denote
  (a) H or
  (b) $C_{1-3}$-alkyl,
$R^{1.3}$ denotes
  (a) H,
  (b) F, —CN, $C_{1-3}$-alkyl, —$CO_2$—$R^{1.3.1}$ or
  (c) a $C_{1-3}$-alkyl group wherein each methylene group may be substituted by up to two fluorine atoms and each methyl group may be substituted by up to three fluorine atoms,
$R^{1.3.1}$ denotes
  (a) H,
  (b) $C_{1-6}$-alkyl,
$R^3$ a 6 or 10-membered aryl group substituted by the groups $R^{3.1}$, $R^{3.2}$ and $R^{3.3}$ or
a 6-membered heteroaryl group substituted by the groups $R^{3.1}$, $R^{3.2}$ and $R^{3.3}$ which is attached via a carbon atom,
$R^{3.1}$ denotes
  (a) H,
  (b) halogen, —$NH_2$, $C_{1-4}$-alkyl-NH, ($C_{1-4}$-alkyl)$_2$N, $C_{1-3}$-alkyl-C(O)—NH, $C_{1-3}$-alkyl-S($O_2$)—NH, —CN, —OH, —O—C(O)—NH—$C_{1-3}$-alkyl,
  (c) $C_{1-4}$-alkyl, $R^{3.1.1}$—$C_{1-3}$-alkylene, $C_{2-4}$-alkenyl, $C_{2-4}$-alkynyl, $C_{1-3}$-alkyl-O, $C_{1-3}$-alkyl-S(O)$_m$, cyclopropyl,
  (d) a $C_{1-3}$-alkyl or $C_{1-3}$-alkyl-O— group wherein each methylene group is substituted by up to two fluorine atoms and each methyl group is substituted by up to three fluorine atoms,
  (e) —C(O)—$R^{3.1.2}$,
  (f) —S(O)$_2$—$R^{3.1.3}$,
$R^{3.1.1}$ denotes
  (a) H,
  (b) $C_{3-6}$-cycloalkyl, $C_{5-6}$-cycloalkenyl,
  (c) ($R^{3.1.1.1}$)$_2$N,
  (d) a saturated, mono- or diunsaturated 5- or 6-membered heterocyclic group which is substituted at a nitrogen atom by a group $R^{3.1.1.1}$ and is substituted at a carbon atom by one or two groups $R^{3.1.1.2}$, or
  (e) a heteroaryl group which is substituted at a carbon atom by a group $R^{3.1.1.2}$,
$R^{3.1.1.1}$ independently of one another denote
  (a) H, $C_{1-4}$-alkyl, $C_{3-6}$-cycloalkyl,
  (b) heterocyclyl,
  (c) aryl-$C_{0-3}$-alkylene or heteroaryl-$C_{0-3}$-alkylene,

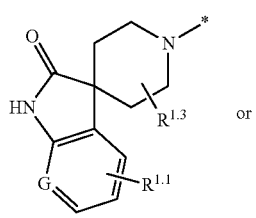

$R^{3.1.1.2}$ independently of one another denote
- (a) H, F, $C_{1-3}$-alkyl, —CN, —OH, —O—$C_{1-3}$-alkyl, —CO(O)$R^{3.1.1.2.1}$, $H_2N$, ($C_{1-4}$-alkyl)-NH, ($C_{1-4}$-alkyl)$_2$N,
- (b) phenyl or phenyl-$CH_2$,
- (c) a $C_{1-3}$-alkyl or —O—$C_{1-3}$-alkyl group wherein each methylene group is substituted by up to two fluorine atoms and each methyl group is substituted by up to three fluorine atoms, or $R^{3.1.1.2.1}$ denotes H, $C_{1-6}$-alkyl, benzyl,
$R^{3.1.2}$ denotes —O—$C_{1-3}$-alkyl, —OH, —$NR^{3.1.2.1}R^{3.1.2.2}$,
$R^{3.1.2.1}$ denotes H, $C_{1-3}$-alkyl,
$R^{3.1.2.2}$ denotes H, $C_{1-3}$-alkyl,
$R^{3.1.2.1}$ and $R^{3.1.2.2}$ together may also form a ring which is selected from among azetidinyl, pyrrolidinyl, piperidinyl, piperazinyl and morpholinyl,
$R^{3.1.3}$ denotes —O—$C_{1-3}$-alkyl, —$NR^{3.1.3.1}R^{3.1.3.2}$,
$R^{3.1.3.1}$ denotes H, $C_{1-3}$-alkyl,
$R^{3.1.3.2}$ denotes H, $C_{1-3}$-alkyl,
$R^{3.1.3.1}$ and $R^{3.1.3.2}$ together may also form a ring which is selected from among azetidinyl, pyrrolidinyl, piperidinyl, piperazinyl and morpholinyl,
$R^{3.2}$ denotes
- (a) H,
- (b) halogen, —$NH_2$, $C_{1-4}$-alkyl-NH, ($C_{1-4}$-alkyl)$_2$N, $C_{1-3}$-alkyl-C(O)—NH, $C_{1-3}$-alkyl-S(O$_2$)—NH, —CN, —OH, —O—C(O)—NH—$C_{1-3}$-alkyl,
- (c) $C_{1-4}$-alkyl, $C_{2-4}$-alkenyl, $C_{2-4}$-alkynyl, $C_{1-3}$-alkyl-O, $C_{1-3}$-alkyl-S(O)$_m$, cyclopropyl,
- (d) a $C_{1-3}$-alkyl or $C_{1-3}$-alkyl-O— group wherein each methylene group is substituted by up to two fluorine atoms and each methyl group is substituted by up to three fluorine atoms,
- (e) —C(O)—$R^{3.2.1}$,
- (f) —S(O)$_2$—$R^{3.2.2}$, $R^{3.2.1}$ denotes —O—$C_{1-3}$-alkyl, —OH, —$NR^{3.2.1.1}R^{3.2.1.2}$,
$R^{3.2.1.1}$ denotes H, $C_{1-3}$-alkyl,
$R^{3.1.1.2}$ denotes H, $C_{1-3}$-alkyl,
$R^{3.2.1.1}$ and $R^{3.2.1.2}$ together may also form a ring which is selected from among azetidinyl, pyrrolidinyl, piperidinyl, piperazinyl and morpholinyl,
$R^{3.2.2}$ denotes —$NR^{3.2.2.1}R^{3.2.2.2}$,
$R^{3.2.2.1}$ denotes H, $C_{1-3}$-alkyl,
$R^{3.2.2.2}$ denotes H, $C_{1-3}$-alkyl,
$R^{3.2.2.1}$ and $R^{3.2.2.2}$ together may also form a ring which is selected from among azetidinyl, pyrrolidinyl, piperidinyl, piperazinyl and morpholinyl,
$R^{3.3}$ denotes
- (a) H,
- (b) halogen, —$NH_2$, $C_{1-4}$-alkyl-NH, ($C_{1-4}$-alkyl)$_2$N, $C_{1-3}$-alkyl-C(O)—NH, $C_{1-3}$-alkyl-S(O$_2$)—NH, —CN, —OH, —O—C(O)—NH—$C_{1-3}$-alkyl,
- (c) $C_{1-4}$-alkyl, $C_{2-4}$-alkenyl, $C_{2-4}$-alkynyl, $C_{1-3}$-alkyl-O, $C_{1-3}$-alkyl-S(O)$_m$, cyclopropyl,
- (d) a $C_{1-3}$-alkyl or $C_{1-3}$-alkyl-O— group wherein each methylene group is substituted by up to two fluorine atoms and each methyl group is substituted by up to three fluorine atoms,
- (e) —C(O)—$R^{3.3.1}$,
- (f) —S(O)$_2$—$R^{3.3.2}$, $R^{3.3.1}$ denotes —O—$C_{1-3}$-alkyl, —OH, —$NR^{3.3.1.1}R^{3.3.1.2}$,
$R^{3.3.1.1}$ denotes H, $C_{1-3}$-alkyl,
$R^{3.3.1.2}$ denotes H, $C_{1-3}$-alkyl,
$R^{3.3.1.1}$ and $R^{3.3.1.2}$ together may also form a ring which is selected from among azetidinyl, pyrrolidinyl, piperidinyl, piperazinyl and morpholinyl,
$R^{3.3.2}$ denotes —O—$C_{1-3}$-alkyl, —$NR^{3.3.2.1}R^{3.3.2.2}$,
$R^{3.3.2.1}$ denotes H, $C_{1-3}$-alkyl,
$R^{3.3.2.2}$ denotes H, $C_{1-3}$-alkyl,
$R^{3.3.2.1}$ and $R^{3.3.2.2}$ together may also form a ring which is selected from among azetidinyl, pyrrolidinyl, piperidinyl, piperazinyl and morpholinyl, or
$R^{3.2}$ und $R^{3.3}$ together with the carbon atoms to which they are attached form a monounsaturated 5-membered or a mono- or diunsaturated 6-membered heterocyclic group or a 5- to 6-membered heteroaryl group, wherein
the heterocycles mentioned previously may contain a carbonyl, thiocarbonyl or cyanoimino group adjacent to a nitrogen atom, and
may optionally be additionally substituted at one or two nitrogen atoms by a group $R^{3.3.3}$ in each case and
may optionally be additionally substituted at one or two carbon atoms by one or two groups $R^{3.3.4}$ in each case,
$R^{3.3.3}$ independently of one another denote
- (a) $C_{1-4}$-alkyl or
- (b) $C_{3-6}$-cycloalkyl, $R^{3.3.4}$ independently of one another denote
- (a) $C_{1-4}$-alkyl or
- (b) $C_{3-6}$-cycloalkyl,
- (c) halogen, CN, —O—$C_{1-3}$-alkyl, —$NH_2$,
- (d) a $C_{1-3}$-alkyl or $C_{1-3}$-alkyl-O— group wherein each methylene group is substituted by up to two fluorine atoms and each methyl group is substituted by up to three fluorine atoms, U denotes N,N-oxide or C—$R^4$,
V denotes N,N-oxide or C—$R^5$,
X denotes N,N-oxide or $CR^6$,
Y denotes N or C—$R^7$,
while at most three of the previously mentioned groups U, V, X or Y simultaneously denote a nitrogen atom, $R^4$ denotes
- (a) H,
- (b) a $C_{1-6}$-alkyl or $C_{1-3}$-alkyl-O— group which is substituted in each case by a group $R^{4.1}$,
- (c) $R^{4.2}R^{4.3}N$, $R^{4.2}R^{4.3}N$—$C_{1-3}$-alkylene,
- (d) halogen, —CN, —OH, —COOH, $C_{1-3}$-alkyl-O, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
- (e) a $C_{1-3}$-alkyl or $C_{1-3}$-alkyl-O— group wherein each methylene group is substituted by up to two fluorine atoms and each methyl group is substituted by up to three fluorine atoms, $R^{4.1}$ denotes H, OH or —O—$CH_3$,
$R^{4.2}$ denotes H or $C_{1-3}$-alkyl,
$R^{4.3}$ denotes H or $C_{1-3}$-alkyl, or
$R^{4.2}$ and $R^{4.3}$ together with the nitrogen atom to which they are bound denote a 3- to 6-membered heterocyclic group,
$R^5$ denotes
- (a) H,
- (b) a $C_{1-6}$-alkyl or $C_{1-3}$-alkyl-O— group which is substituted in each case by a group $R^{5.1}$,
- (c) —$NR^{5.2}R^{5.3}$, $NR^{5.2}R^{5.3}$—$C_{1-3}$-alkylene,
- (d) halogen, —CN, —OH, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
- (e) aryl-$C_{0-3}$-alkylen-O— group,
- (f) a $C_{1-3}$-alkyl or $C_{1-3}$-alkyl-O— group wherein each methylene group is substituted by up to two fluorine atoms and each methyl group is substituted by up to three fluorine atoms, $R^{5.1}$ denotes H, OH or —O—$CH_3$,
$R^{5.2}$ denotes H or $C_{1-6}$-alkyl,
$R^{5.3}$ denotes H, $C_{1-6}$-alkyl or —$SO_2$—$C_{1-3}$-alkyl, or $R^{5.2}$ and $R^{5.3}$ together with the nitrogen atom to which they are bound denote a 3- to 6-membered heterocyclic group, $R^6$ denotes
(a) H,
(b) a $C_{1-6}$-alkyl or $C_{1-3}$-alkyl-O— group which is substituted in each case by a group $R^{6.1}$,
(c) $R^{6.2}R^{6.3}N$, $R^{6.2}R^{6.3}N$—$C_{1-3}$-alkylene,
(d) halogen, —CN, —OH, —COOH, $C_{1-3}$-alkyl-O, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
(e) a $C_{1-3}$-alkyl or $C_{1-3}$-alkyl-O— group wherein each methylene group is substituted by up to two fluorine atoms and each methyl group is substituted by up to three fluorine atoms, $R^{6.1}$ denotes H, OH or —O—$CH_3$,
$R^{6.2}$ denotes H or $C_{1-3}$-alkyl,
$R^{6.3}$ denotes H or $C_{1-3}$-alkyl, or
$R^{6.2}$ and $R^{6.3}$ together with the nitrogen atom to which they are bound denote a 3- to 6-membered heterocyclic group, and $R^7$ denotes H, halogen or $C_{1-3}$-alkyl, the tautomers, the diastereomers, the enantiomers, the hydrates, the mixtures thereof and the salts thereof and the hydrates of the salts, particularly the physiologically acceptable salts thereof with inorganic or organic acids or bases.

A second embodiment of the present invention comprises the compounds of the above general formula I, wherein U, V, X, Y, $R^2$ and $R^3$ are defined as hereinbefore in the first embodiment and $R^1$ denotes a group selected from

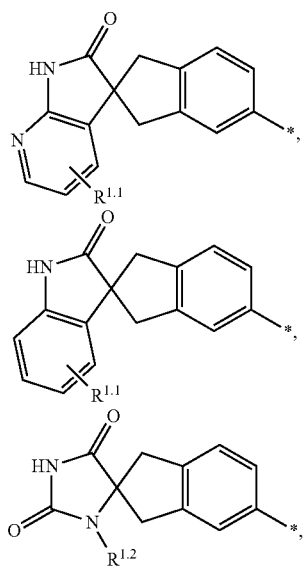

$R^{1.1}$ denotes
a) H,
b) halogen, $C_{1-3}$-alkyl, —OH, —CN, —O—$C_{1-3}$-alkyl, —C(O)—O—$C_{1-3}$-alkyl, $C_{2-4}$-alkenyl, $C_{2-4}$-alkynyl, $C_{1-3}$-alkyl-S, —$NH_2$,
c) a $C_{1-3}$-alkyl group or $C_{1-3}$-alkyl-O— group wherein each methylene group is substituted by up to two fluorine atoms and each methyl group is substituted by up to three fluorine atoms, and $R^{1.2}$ denotes
(a) H or
(b) $CH_3$, the tautomers, the diastereomers, the enantiomers, the hydrates, the mixtures thereof and the salts thereof and the hydrates of the salts, particularly the physiologically acceptable salts thereof with inorganic or organic acids or bases.

A third embodiment of the present invention comprises the compounds of the above general formula I, wherein U, V, X, Y and $R^3$ are defined as hereinbefore in the first embodiment and $R^1$ and $R^2$ together with the nitrogen atom to which they are bound denote a group selected from

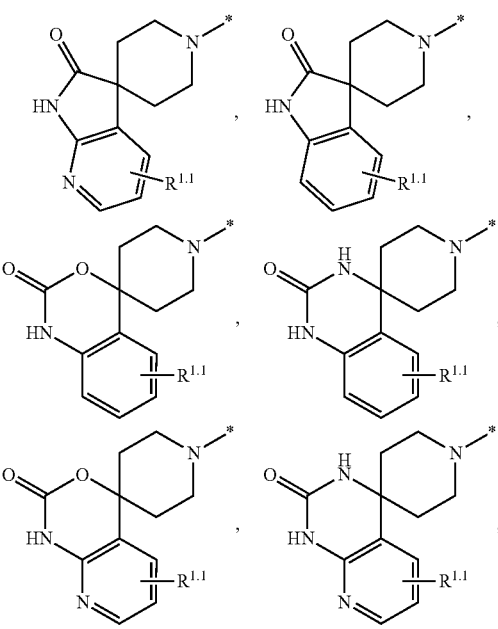

$R^{1.1}$ denotes
(a) H,
(b) halogen, $C_{1-3}$-alkyl, —OH, —CN, —O—$C_{1-3}$-alkyl, —C(O)—O—$C_{1-3}$-alkyl, $C_{2-4}$-alkenyl, $C_{2-4}$-alkynyl, $C_{1-3}$-alkyl-S, —$NH_2$,
(c) a $C_{1-3}$-alkyl group or $C_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof and the hydrates of the salts, particularly the physiologically acceptable salts thereof with inorganic or organic acids or bases.

A fourth embodiment of the present invention comprises the compounds of the above general formula I, wherein U, V, X, Y, $R^2$ and $R^3$ are defined as hereinbefore in the first embodiment and $R^1$ denotes a group selected from

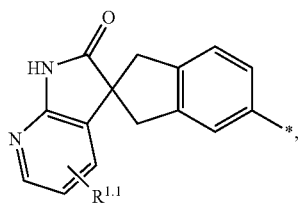

-continued

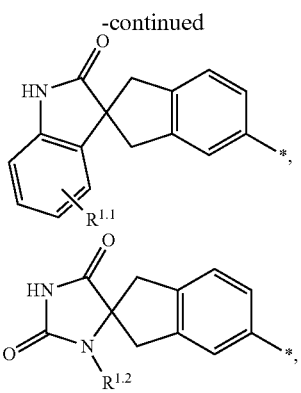

$R^{1.1}$ denotes
(a) F, CH$_3$, —OH, —O—CH$_3$ or
(b) CF$_3$, the tautomers, the diastereomers, the enantiomers, the hydrates, the mixtures thereof and the salts thereof and the hydrates of the salts, particularly the physiologically acceptable salts thereof with inorganic or organic acids or bases.

A fifth embodiment of the present invention comprises the compounds of the above general formula I, wherein U, V, X, Y and $R^3$ are defined as hereinbefore in the first embodiment and $R^1$ and $R^2$ together with the nitrogen atom to which they are bound denote a group selected from

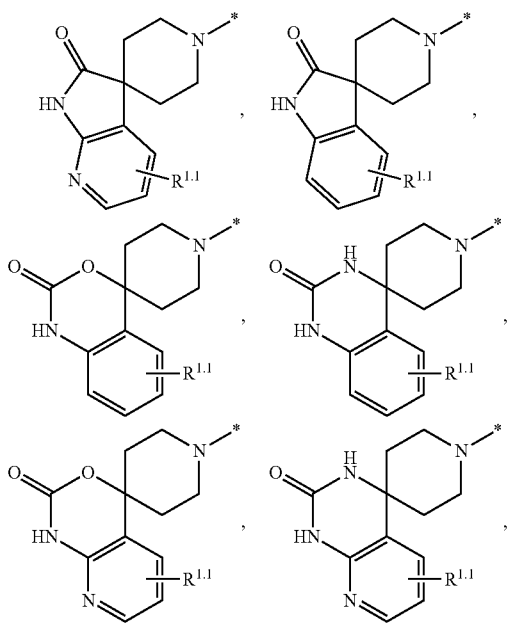

$R^{1.1}$ denotes
(a) F, CH$_3$, —OH, —O—CH$_3$ or CF$_3$, the tautomers, the diastereomers, the enantiomers, the hydrates, the mixtures thereof and the salts thereof and the hydrates of the salts, particularly the physiologically acceptable salts thereof with inorganic or organic acids or bases.

A sixth embodiment of the present invention comprises the compounds of the above general formula I, wherein U, V, X, Y, $R^2$ and $R^3$ are defined as hereinbefore in the first embodiment and $R^1$ denotes a group selected from

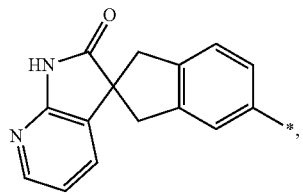

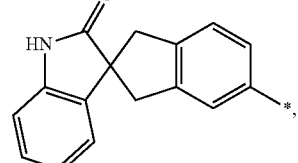

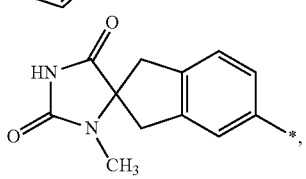

the tautomers, the diastereomers, the enantiomers, the hydrates, the mixtures thereof and the salts thereof and the hydrates of the salts, particularly the physiologically acceptable salts thereof with inorganic or organic acids or bases.

A seventh embodiment of the present invention comprises the compounds of the above general formula I, wherein U, V, X, Y and $R^3$ are defined as hereinbefore in the first embodiment and $R^1$ and $R^2$ together with the nitrogen atom to which they are bound denote a group selected from

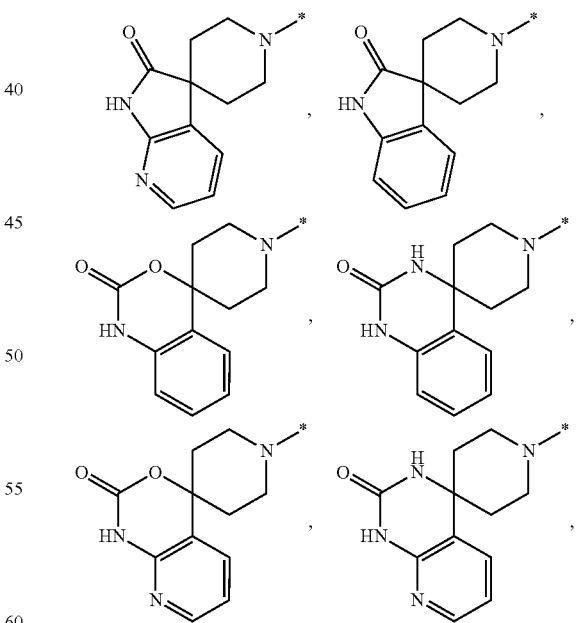

the tautomers, the diastereomers, the enantiomers, the hydrates, the mixtures thereof and the salts thereof and the hydrates of the salts, particularly the physiologically acceptable salts thereof with inorganic or organic acids or bases.

An eighth embodiment of the present invention comprises the compounds of the above general formula I, wherein U, V, X, Y, $R^1$ and $R^2$ are defined as hereinbefore in the first, second, fourth or sixth embodiment and
$R^3$ denotes a group of general formula IV

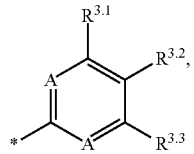 (IV)

A independently of one another denote C—H, C—F or N,
$R^{3.1}$ denotes
  (a) H,
  (b) halogen, —$NH_2$, $C_{1-4}$-alkyl-NH, ($C_{1-4}$-alkyl)$_2$N, $C_{1-3}$-alkyl-C(O)—NH, $C_{1-3}$-alkyl-S(O)$_2$—NH, —CN, —OH, —O—C(O)—NH—$C_{1-3}$-alkyl,
  (c) $C_{1-4}$-alkyl, $R^{3.1.1}$—$C_{1-3}$-alkylene, $C_{2-4}$-alkenyl, $C_{2-4}$-alkynyl, $C_{1-3}$-alkyl-O, $C_{1-3}$-alkyl-S,
  (d) a $C_{1-3}$-alkyl or $C_{1-3}$-alkyl-O— group wherein each methylene group is substituted by up to two fluorine atoms and each methyl group is substituted by up to three fluorine atoms,
  (e) —C(O)—$R^{3.1.2}$,
  (f) —S(O)$_2$—$R^{3.1.3}$,
$R^{3.1.1}$ denotes
  (a) H,
  (b) $C_{3-6}$-cycloalkyl, $C_{5-6}$-cycloalkenyl,
  (c) ($R^{3.1.1.1}$)$_2$N,
  (d) a saturated, mono- or diunsaturated 5- or 6-membered heterocyclic group which is substituted at a nitrogen atom by a group $R^{3.1.1.1}$ and is substituted at a carbon atom by one or two groups $R^{3.1.1.2}$, or
  (e) a heteroaryl group which is substituted at a carbon atom by a group $R^{3.1.1.2}$,
$R^{3.1.1.1}$ independently of one another denote
  (a) H, $C_{1-4}$-alkyl, $C_{3-6}$-cycloalkyl,
  (b) heterocyclyl,
  (c) aryl-$C_{0-3}$-alkylene or heteroaryl-$C_{0-3}$-alkylene,
$R^{3.1.1.2}$ independently of one another denote
  (a) H, F, $C_{1-3}$-alkyl, —CN, —OH, —O—$C_{1-3}$-alkyl, —CO(O)$R^{3.1.1.2.1}$, $H_2N$, ($C_{1-4}$-alkyl)-NH, ($C_{1-4}$-alkyl)$_2$N,
  (b) phenyl or phenyl-$CH_2$,
  (c) a $C_{1-3}$-alkyl or —O—$C_{1-3}$-alkyl group wherein each methylene group is substituted by up to two fluorine atoms and each methyl group is substituted by up to three fluorine atoms, or
$R^{3.1.1.2.1}$ denotes H, $C_{1-6}$-alkyl, benzyl,
$R^{3.1.2}$ denotes —O—$C_{1-3}$-alkyl, —OH, —$NR^{3.1.2.1}R^{3.1.1.2}$,
$R^{3.1.2.1}$ denotes H, $C_{1-3}$-alkyl,
$R^{3.1.2.2}$ denotes H, $C_{1-3}$-alkyl,
$R^{3.1.3}$ denotes —$NR^{3.1.3.1}R^{3.1.3.2}$,
$R^{3.1.3.1}$ denotes H, $C_{1-3}$-alkyl,
$R^{3.1.3.2}$ denotes H, $C_{1-3}$-alkyl,
$R^{3.2}$ denotes
  (a) H,
  (b) halogen, —$NH_2$, $C_{1-4}$-alkyl-NH, ($C_{1-4}$-alkyl)$_2$N, $C_{1-3}$-alkyl-C(O)—NH, $C_{1-3}$-alkyl-S(O)$_2$—NH, —CN, —OH, —O—C(O)—NH—$C_{1-3}$-alkyl,
  (c) $C_{1-4}$-alkyl, $C_{2-4}$-alkenyl, $C_{2-4}$-alkynyl, $C_{1-3}$-alkyl-O, $C_{1-3}$-alkyl-S,
  (d) a $C_{1-3}$-alkyl or $C_{1-3}$-alkyl-O— group wherein each methylene group is substituted by up to two fluorine atoms and each methyl group is substituted by up to three fluorine atoms,
  (e) —C(O)—$R^{3.2.1}$,
  (f) —S(O)$_2$—$R^{3.2.2}$,
$R^{3.2.1}$ denotes —O—$C_{1-3}$-alkyl, —OH, —$NR^{3.2.1.1}R^{3.2.1.2}$,
$R^{3.2.1.1}$ denotes H, $C_{1-3}$-alkyl,
$R^{3.2.1.2}$ denotes H, $C_{1-3}$-alkyl,
$R^{3.2.2}$ denotes —$NR^{3.2.2.1}R^{3.2.2.2}$,
$R^{3.2.2.1}$ denotes H, $C_{1-3}$-alkyl,
$R^{3.2.2.2}$ denotes H, $C_{1-3}$-alkyl,
$R^{3.3}$ denotes
  (a) H,
  (b) halogen, —$NH_2$, $C_{1-4}$-alkyl-NH, ($C_{1-4}$-alkyl)$_2$N, $C_{1-3}$-alkyl-C(O)—NH, $C_{1-3}$-alkyl-S(O)$_2$—NH, —CN, —OH, —O—C(O)—NH—$C_{1-3}$-alkyl,
  (c) $C_{1-4}$-alkyl, $C_{2-4}$-alkenyl, $C_{2-4}$-alkynyl, $C_{1-3}$-alkyl-O, $C_{1-3}$-alkyl-S,
  (d) a $C_{1-3}$-alkyl or $C_{1-3}$-alkyl-O— group wherein each methylene group is substituted by up to two fluorine atoms and each methyl group is substituted by up to three fluorine atoms,
  (e) —C(O)—$R^{3.3.1}$,
  (f) —S(O)$_2$—$R^{3.3.2}$,
$R^{3.3.1}$ denotes —O—$C_{1-3}$-alkyl, —OH, —$NR^{3.3.1.1}R^{3.3.1.2}$,
$R^{3.3.1.1}$ denotes H, $C_{1-3}$-alkyl,
$R^{3.3.1.2}$ denotes H, $C_{1-3}$-alkyl,
$R^{3.3.2}$ denotes —O—$C_{1-3}$-alkyl, —$NR^{3.3.2.1}R^{3.3.2.2}$,
$R^{3.3.2.1}$ denotes H, $C_{1-3}$-alkyl,
$R^{3.3.2.2}$ denotes H, $C_{1-3}$-alkyl, or
$R^{3.2}$ and $R^{3.3}$ together with the carbon atoms to which they are attached form a monounsaturated 5-membered or a mono- or diunsaturated 6-membered heterocyclic group or a 5- to 6-membered heteroaryl group, wherein
  the heterocycles mentioned previously may contain a carbonyl, thiocarbonyl or cyanoimino group adjacent to a nitrogen atom, and
  may optionally be additionally substituted at one or two nitrogen atoms by a group $R^{3.3.3}$ in each case and
  may optionally be additionally substituted at one or two carbon atoms by one or two groups $R^{3.3.4}$ in each case,
$R^{3.3.3}$ independently of one another denote
  (a) $C_{1-4}$-alkyl or
  (b) $C_{3-6}$-cycloalkyl,
$R^{3.3.4}$ independently of one another denote
  (a) $C_{1-4}$-alkyl, $C_{3-6}$-cycloalkyl,
  (b) halogen, CN, $C_{1-3}$-alkyl-O—, —$NH_2$,
  (c) a $C_{1-3}$-alkyl or $C_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof and the hydrates of the salts, particularly the physiologically acceptable salts thereof with inorganic or organic acids or bases.

A ninth embodiment of the present invention comprises the compounds of the above general formula I, wherein U, V, X, Y, $R^1$ and $R^2$ are defined as hereinbefore in the first, second, fourth or sixth embodiment and R³ denotes a group of general formula IV

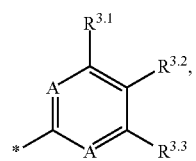

(IV)

A independently of one another denote C—H, C—F or N,
R³·¹ denotes
  (a) H,
  (b) halogen, —NH$_2$, C$_{1-4}$-alkyl-NH, (C$_{1-4}$-alkyl)$_2$N, C$_{1-3}$-alkyl-C(O)—NH, —CN, —OH, —O—C(O)—NH—C$_{1-3}$-alkyl,
  (c) C$_{1-4}$-alkyl, C$_{2-4}$-alkenyl, C$_{2-4}$-alkynyl, C$_{1-3}$-alkyl-O, C$_{1-3}$-alkyl-S,
  (d) a C$_{1-3}$-alkyl or C$_{1-3}$-alkyl-O— group wherein each methylene group is substituted by up to two fluorine atoms and each methyl group is substituted by up to three fluorine atoms,
R³·² denotes
  (a) H,
  (b) halogen, —NH$_2$, C$_{1-4}$-alkyl-NH, (C$_{1-4}$-alkyl)$_2$N, C$_{1-3}$-alkyl-C(O)—NH, —CN, —OH, —O—C(O)—NH—C$_{1-3}$-alkyl,
  (c) C$_{1-4}$-alkyl, C$_{2-4}$-alkenyl, C$_{2-4}$-alkynyl, C$_{1-3}$-alkyl-O, C$_{1-3}$-alkyl-S,
  (d) a C$_{1-3}$-alkyl or C$_{1-3}$-alkyl-O— group wherein each methylene group is substituted by up to two fluorine atoms and each methyl group is substituted by up to three fluorine atoms,
R³·³ denotes
  (a) H,
  (b) halogen, —NH$_2$, C$_{1-4}$-alkyl-NH, (C$_{1-4}$-alkyl)$_2$N, C$_{1-3}$-alkyl-C(O)—NH, —CN, —OH, —O—C(O)—NH—C$_{1-3}$-alkyl,
  (c) C$_{1-4}$-alkyl, C$_{2-4}$-alkenyl, C$_{2-4}$-alkynyl, C$_{1-3}$-alkyl-O, C$_{1-3}$-alkyl-S,
  (d) a C$_{1-3}$-alkyl or C$_{1-3}$-alkyl-O— group wherein each methylene group is substituted by up to two fluorine atoms and each methyl group is substituted by up to three fluorine atoms,
R³·² and R³·³ together with the carbon atoms to which they are attached form a monounsaturated 5-membered or a mono- or diunsaturated 6-membered heterocyclic group or a 5- to 6-membered heteroaryl group, wherein
  the heterocycles mentioned previously may contain a carbonyl, thiocarbonyl or cyanoimino group adjacent to a nitrogen atom, and
  may optionally be additionally substituted at one or two nitrogen atoms by a group R³·³·³ in each case and
  may optionally be additionally substituted at one or two carbon atoms by one or two groups R³·³·⁴ in each case,
R³·³·³ independently of one another denote
  (a) C$_{1-4}$-alkyl or
  (b) C$_{3-6}$-cycloalkyl,
R³·³·⁴ independently of one another denote
  (a) C$_{1-4}$-alkyl, C$_{3-6}$-cycloalkyl,
  (b) halogen, CN, C$_{1-3}$-alkyl-O—, —NH$_2$,
  (c) a C$_{1-3}$-alkyl or C$_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof and the hydrates of the salts, particularly the physiologically acceptable salts thereof with inorganic or organic acids or bases.

A tenth embodiment of the present invention comprises the compounds of the above general formula I, wherein U, V, X, Y, R¹ and R² are defined as hereinbefore in the first, second, fourth or sixth embodiment and
R³ denotes a group of general formula IVa

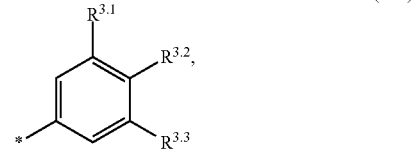

(IVa)

R³·¹ denotes
  (a) H,
  (b) F, Cl, Br, —NH$_2$, C$_{1-3}$-alkyl-NH, (C$_{1-3}$-alkyl)$_2$N, C$_{1-3}$-alkyl-C(O)—NH, —CN, —OH,
  (c) C$_{1-4}$-alkyl, C$_{2-4}$-alkenyl, C$_{2-4}$-alkynyl, C$_{1-3}$-alkyl-S,
  (d) a C$_{1-3}$-alkyl or C$_{1-3}$-alkyl-O— group wherein each methylene group is substituted by up to two fluorine atoms and each methyl group is substituted by up to three fluorine atoms,
R³·² denotes
  (a) H,
  (b) F, Cl, Br, H$_2$N, (C$_{1-4}$-alkyl)-NH, (C$_{1-4}$-alkyl)$_2$N, (C$_{1-3}$-alkyl)-C(O)—NH, —OH,
  (c) C$_{1-4}$-alkyl,
  (d) a C$_{1-3}$-alkyl or C$_{1-3}$-alkyl-O— group wherein each methylene group is substituted by up to two fluorine atoms and each methyl group is substituted by up to three fluorine atoms,
R³·³ denotes
  (a) H,
  (b) F, Cl, Br, H$_2$N, (C$_{1-4}$-alkyl)-NH, (C$_{1-4}$-alkyl)$_2$N, (C$_{1-3}$-alkyl)-C(O)—NH, —OH,
  (c) C$_{1-4}$-alkyl,
  (d) a C$_{1-3}$-alkyl or C$_{1-3}$-alkyl-O— group wherein each methylene group is substituted by up to two fluorine atoms and each methyl group is substituted by up to three fluorine atoms,
R³·² and R³·³ together with the carbon atoms to which they are attached form a monounsaturated 5-membered or a mono- or diunsaturated 6-membered heterocyclic group or a 5- to 6-membered heteroaryl group, wherein
  the heterocycles mentioned previously may contain a carbonyl, thiocarbonyl or cyanoimino group adjacent to a nitrogen atom, and
  may optionally be additionally substituted at one or two nitrogen atoms by a group R³·³·³ in each case and
  may optionally be additionally substituted at one or two carbon atoms by one or two groups R³·³·⁴ in each case,
R³·³·³ independently of one another denote
  (a) C$_{1-4}$-alkyl or
  (b) C$_{3-6}$-cycloalkyl,
R³·³·⁴ independently of one another denote
  (a) C$_{1-4}$-alkyl, C$_{3-6}$-cycloalkyl,
  (b) halogen, CN, C$_{1-3}$-alkyl-O—, —NH$_2$,
  (c) a C$_{1-3}$-alkyl or C$_{1-3}$-alkyl-O— group wherein each methylene group is substituted by up to two fluorine atoms and each methyl group is substituted by up to three fluorine atoms, and $R^{3.4}$ denotes H or F, the tautomers, the diastereomers, the enantiomers, the hydrates, the mixtures thereof and the salts thereof and the hydrates of the salts, particularly the physiologically acceptable salts thereof with inorganic or organic acids or bases.

An eleventh embodiment of the present invention comprises the compounds of the above general formula I, wherein U, V, X, Y, $R^1$ and $R^2$ are defined as hereinbefore in the first, second, fourth or sixth embodiment and $R^3$ denotes a group selected from

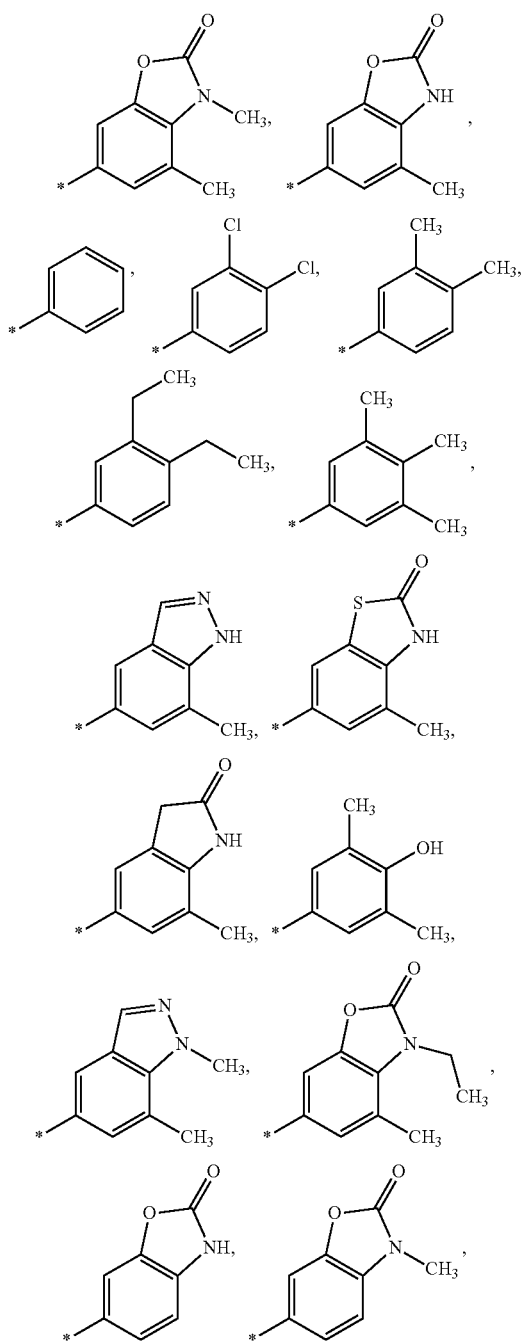

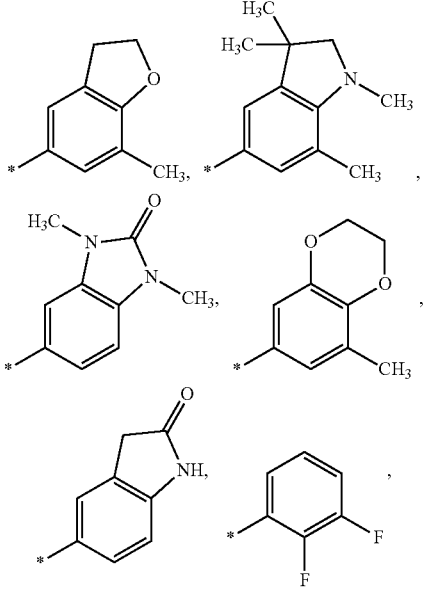

the tautomers, the diastereomers, the enantiomers, the hydrates, the mixtures thereof and the salts thereof and the hydrates of the salts, particularly the physiologically acceptable salts thereof with inorganic or organic acids or bases.

A twelfth embodiment of the present invention comprises the compounds of the above general formula I, wherein U, V, X, Y, $R^1$ and $R^2$ are as defined hereinbefore in the first, second, third, fourth, fifth, sixth or seventh embodiment and $R^3$ denotes a group of general formula IVb

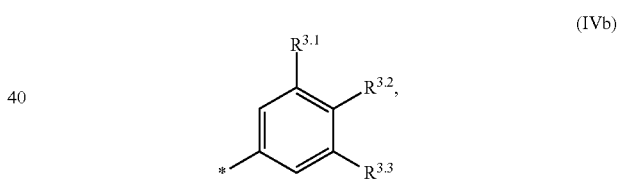

(IVb)

$R^{3.1}$ denotes
  (a) H,
  (b) F, Cl, Br, —NH$_2$, $C_{1-3}$-alkyl-NH, ($C_{1-3}$-alkyl)$_2$N, $C_{1-3}$-alkyl-C(O)—NH, —CN, —OH,
  (c) $C_{1-4}$-alkyl, $C_{2-4}$-alkenyl, $C_{2-4}$-alkynyl, $C_{1-3}$-alkyl-O, $C_{1-3}$-alkyl-S,
  (d) a $C_{1-3}$-alkyl or $C_{1-3}$-alkyl-O— group wherein each methylene group is substituted by up to two fluorine atoms and each methyl group is substituted by up to three fluorine atoms, $R^{3.2}$ and $R^{3.3}$ together with the carbon atoms to which they are bound form a monounsaturated 5-membered heterocyclic group or a mono- or diunsaturated 6-membered heterocyclic group or a 5- to 6-membered heteroaryl group, wherein the previously mentioned heterocycles contain a carbonyl, thiocarbonyl or cyanimino group adjacent to a nitrogen atom, and may each optionally additionally be substituted at one or two nitrogen atoms by a group $R^{3.3.3}$ and may each optionally additionally be substituted at one or two carbon atoms by one or two groups $R^{3.3.4}$, $R^{3.3.3}$ independently of one another denote
(a) $C_{1-4}$-alkyl or
(b) $C_{3-6}$-cycloalkyl, and $R^{3.3.4}$ independently of one another denote
(a) $C_{1-4}$-alkyl, $C_{3-6}$-cycloalkyl,
(b) halogen, —CN, —O—$C_{1-3}$-alkyl, —NH$_2$,
(c) a $C_{1-3}$-alkyl or $C_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof and the hydrates of the salts, particularly the physiologically acceptable salts thereof with inorganic or organic acids or bases.

A thirteenth embodiment of the present invention comprises the compounds of the above general formula I, wherein U, V, X, Y, $R^1$ and $R^2$ are as defined hereinbefore in the first, second, third, fourth, fifth, sixth or seventh embodiment and $R^3$ denotes a group of general formula IVb

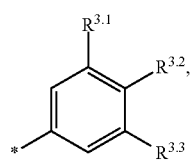

(IVb)

$R^{3.1}$ denotes
(a) H,
(b) F, Cl, Br, —NH$_2$, $C_{1-3}$-alkyl-NH, ($C_{1-3}$-alkyl)$_2$N, $C_{1-3}$-alkyl-C(O)—NH, —CN, —OH,
(c) $C_{1-4}$-alkyl, $C_{2-4}$-alkenyl, $C_{2-4}$-alkynyl, $C_{1-3}$-alkyl-O, $C_{1-3}$-alkyl-S,
(d) a $C_{1-3}$-alkyl or $C_{1-3}$-alkyl-O— group wherein each methylene group is substituted by up to two fluorine atoms and each methyl group is substituted by up to three fluorine atoms, $R^{3.2}$ and $R^{3.3}$ together with the carbon atoms to which they are bound form a monounsaturated 5-membered heterocyclic group or a 5-membered heteroaryl group, wherein
the previously mentioned heterocycles contain a carbonyl, thiocarbonyl or cyanimino group adjacent to a nitrogen atom, and
may each optionally additionally be substituted at one or two nitrogen atoms by a group $R^{3.3.3}$ and
may each optionally additionally be substituted at one or two carbon atoms by one or two groups $R^{3.3.4}$, $R^{3.3.3}$ independently of one another denote
(a) $C_{1-4}$-alkyl or
(b) $C_{3-6}$-cycloalkyl, and $R^{3.3.4}$ independently of one another denote
(a) $C_{1-4}$-alkyl, $C_{3-6}$-cycloalkyl,
(b) halogen, —CN, —O—$C_{1-3}$-alkyl, —NH$_2$,
(c) a $C_{1-3}$-alkyl or $C_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof and the hydrates of the salts, particularly the physiologically acceptable salts thereof with inorganic or organic acids or bases.

A fourteenth embodiment of the present invention comprises the compounds of the above general formula I, wherein U, V, X, Y, $R^1$ and $R^2$ are as defined hereinbefore in the first, second, third, fourth, fifth, sixth or seventh embodiment and $R^3$ denotes a group of general formula IVc

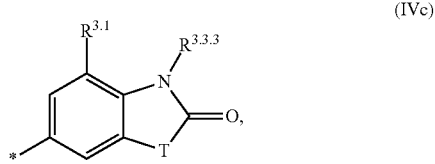

(IVc)

T denotes O, S, CH$_2$, NH or N—$R^{3.3.3}$, $R^{3.1}$ denotes
(a) H,
(b) F, Cl, Br, —NH$_2$, $C_{1-3}$-alkyl-NH, ($C_{1-3}$-alkyl)$_2$N, $C_{1-3}$-alkyl-C(O)—NH, —CN, —OH,
(c) $C_{1-4}$-alkyl, $C_{2-4}$-alkenyl, $C_{2-4}$-alkynyl, $C_{1-3}$-alkyl-O, $C_{1-3}$-alkyl-S,
(d) a $C_{1-3}$-alkyl or $C_{1-3}$-alkyl-O— group wherein each methylene group is substituted by up to two fluorine atoms and each methyl group is substituted by up to three fluorine atoms, and $R^{3.3.3}$ independently of one another denote
(a) $C_{1-4}$-alkyl or
(b) $C_{3-6}$-cycloalkyl, the tautomers, the diastereomers, the enantiomers, the hydrates, the mixtures thereof and the salts thereof and the hydrates of the salts, particularly the physiologically acceptable salts thereof with inorganic or organic acids or bases.

A fifteenth embodiment of the present invention comprises the compounds of the above general formula I, wherein U, V, X, Y, $R^1$ and $R^2$ are as defined hereinbefore in the first, second, third, fourth, fifth, sixth or seventh embodiment and $R^3$ denotes a group selected from

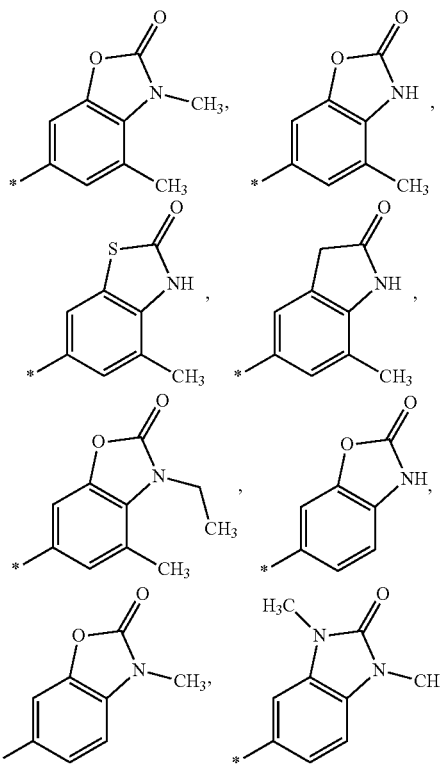

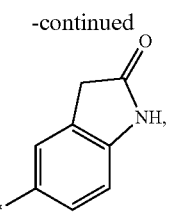

the tautomers, the diastereomers, the enantiomers, the hydrates, the mixtures thereof and the salts thereof and the hydrates of the salts, particularly the physiologically acceptable salts thereof with inorganic or organic acids or bases.

A sixteenth embodiment of the present invention comprises the compounds of the above general formula I, wherein Y, $R^1$, $R^2$ and $R^3$ are as defined hereinbefore in the first, second, third, fourth, fifth, sixth, seventh, eighth, ninth, tenth, eleventh, twelfth, thirteenth, fourteenth or fifteenth embodiment and U—V—X denotes a group selected from
—N=N—(C—$R^6$)=, —N=(C—$R^5$)—N=, —N=(C—$R^5$)—(C—$R^6$)=, —(N-oxide)=(C—$R^5$)—(C$R^6$)=, —(C$R^4$)=N—N=, —(C$R^4$)=N—(C$R^6$)=, —(C—$R^4$)=N(oxide)-(C—$R^6$)=, —(C$R^4$)=(C—$R^5$)—N=, —(C$R^4$)=(C—$R^5$)—(N-oxide)=, —(C$R^4$)=(C—$R^5$)—(C$R^6$)=, and $R^4$ denotes
(a) H,
(b) a $C_{1-6}$-alkyl or $C_{1-3}$-alkyl-O— group which is substituted in each case by a group $R^{4.1}$,
(c) $R^{4.2}R^{4.3}$N, $R^{4.2}R^{4.3}$N—$C_{1-3}$-alkylene,
(d) halogen, —CN, —OH, —COOH, $C_{1-3}$alkyl-O, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
(e) a $C_{1-3}$-alkyl or $C_{1-3}$-alkyl-O— group wherein each methylene group is substituted by up to two fluorine atoms and each methyl group is substituted by up to three fluorine atoms, $R^{4.1}$ denotes H, OH or —O—$CH_3$,
$R^{4.2}$ denotes H or $C_{1-3}$-alkyl,
$R^{4.3}$ denotes H or $C_{1-3}$-alkyl, or
$R^{4.2}$ and $R^{4.3}$ together with the nitrogen atom to which they are bound denote a 3- to 6-membered heterocyclic group, $R^5$ denotes
(a) H,
(b) a $C_{1-6}$-alkyl or $C_{1-3}$-alkyl-O— group which is substituted by a group $R^{5.1}$ in each case,
(c) —N$R^{5.2}R^{5.3}$, N$R^{5.2}R^{5.3}$—$C_{1-3}$-alkylene,
(d) halogen, —CN, —OH, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
(e) aryl-$C_{0-3}$-alkylen-O— group,
(f) a $C_{1-3}$-alkyl or $C_{1-3}$-alkyl-O— group wherein each methylene group is substituted by up to two fluorine atoms and each methyl group is substituted by up to three fluorine atoms, $R^{5.1}$ denotes H, OH or —O—$CH_3$,
$R^{5.2}$ denotes H or $C_{1-6}$-alkyl,
$R^{5.3}$ denotes H, $C_{1-6}$-alkyl or —$SO_2$—$C_{1-3}$-alkyl $R^6$ denotes
(a) H,
(b) a $C_{1-6}$-alkyl or $C_{1-3}$-alkyl-O— group which is substituted in each case by a group $R^{6.1}$,
(c) $R^{6.2}R^{6.3}$N, $R^{6.2}R^{6.3}$N—$C_{1-3}$-alkylene,
(d) halogen, —CN, —OH, —COOH, $C_{1-3}$-alkyl-O, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
(e) a $C_{1-3}$-alkyl or $C_{1-3}$-alkyl-O— group wherein each methylene group is substituted by up to two fluorine atoms and each methyl group is substituted by up to three fluorine atoms, $R^{6.1}$ denotes H, OH or —O—$CH_3$,
$R^{6.2}$ denotes H or $C_{1-3}$-alkyl,
$R^{6.3}$ denotes H or $C_{1-3}$-alkyl, or
$R^{6.2}$ and $R^{6.3}$ together with the nitrogen atom to which they are bound denote a 3- to 6-membered heterocyclic group, the tautomers, the diastereomers, the enantiomers, the hydrates, the mixtures thereof and the salts thereof and the hydrates of the salts, particularly the physiologically acceptable salts thereof with inorganic or organic acids or bases.

A seventeenth embodiment of the present invention comprises the compounds of the above general formula I, wherein Y, $R^1$, $R^2$ and $R^3$ are as defined hereinbefore in the first, second, third, fourth, fifth, sixth, seventh, eighth, ninth, tenth, eleventh, twelfth, thirteenth, fourteenth or fifteenth embodiment and the ring

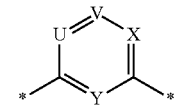

denotes a group selected from

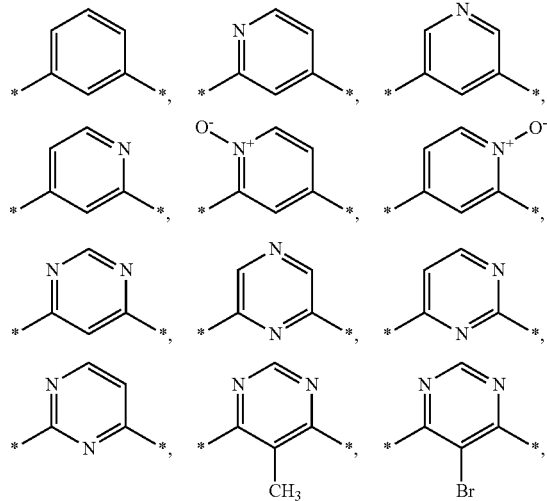

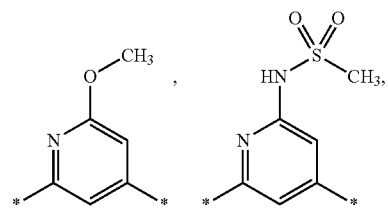

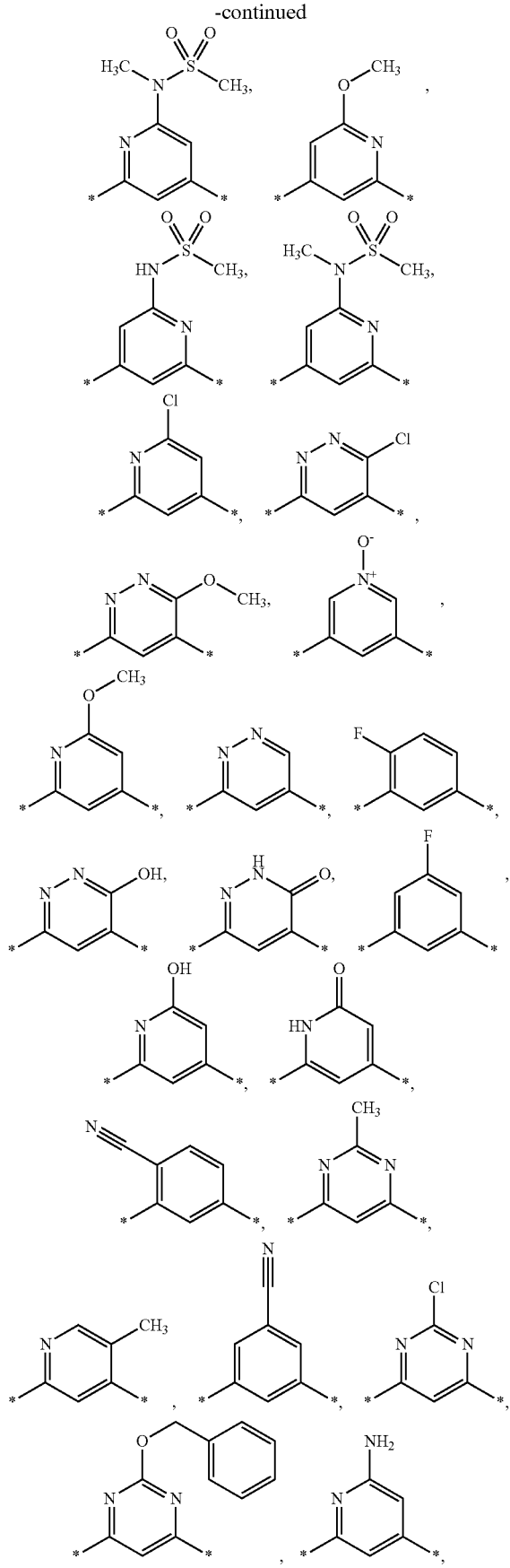

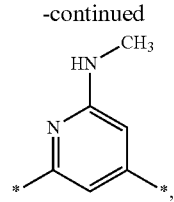

the tautomers, the diastereomers, the enantiomers, the hydrates, the mixtures thereof and the salts thereof and the hydrates of the salts, particularly the physiologically acceptable salts thereof with inorganic or organic acids or bases.

An eighteenth embodiment of the present invention comprises the compounds of the above general formula I wherein $R^1$ denotes a group selected from

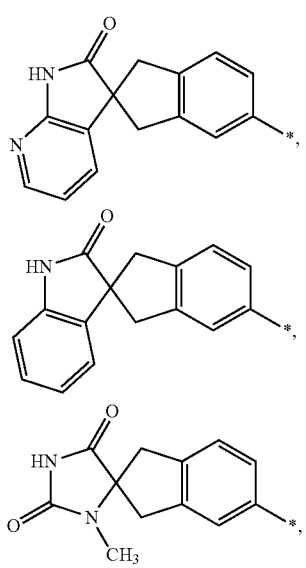

$R^2$ denotes H, $R^3$ denotes a group selected from

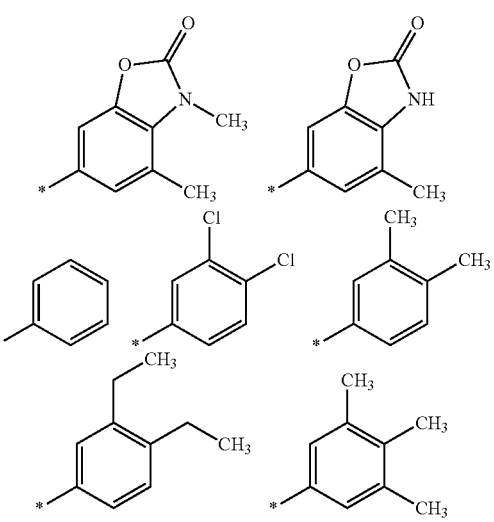

-continued
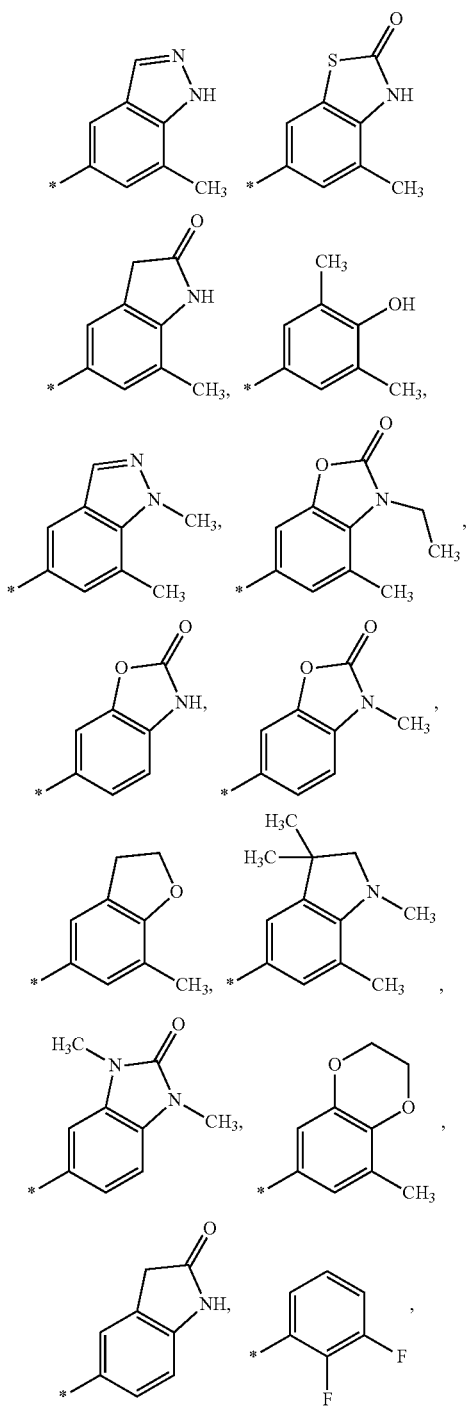
the ring
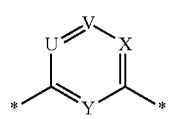
denotes a group selected from
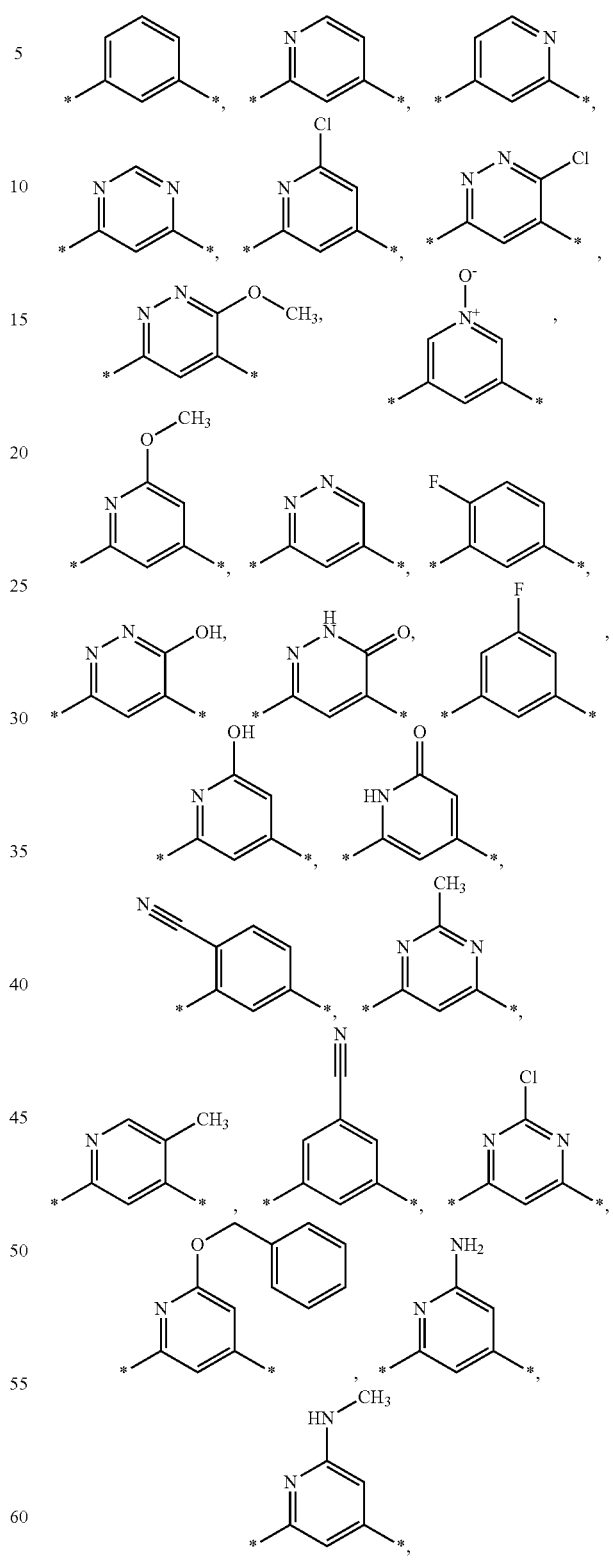
the tautomers, the diastereomers, the enantiomers, the hydrates, the mixtures thereof and the salts thereof and the hydrates of the salts, particularly the physiologically acceptable salts thereof with inorganic or organic acids or bases.

A nineteenth embodiment of the present invention comprises the compounds of the above general formula I wherein R¹ and R² together with the nitrogen atom to which they are bound denote a group selected from
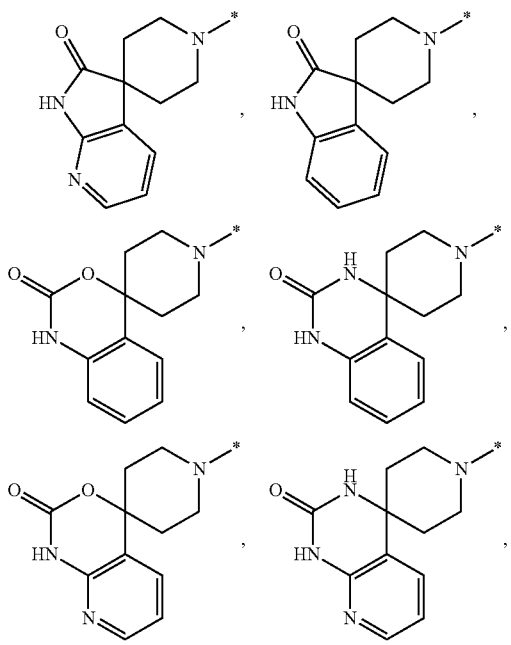
R³ denotes a group selected from
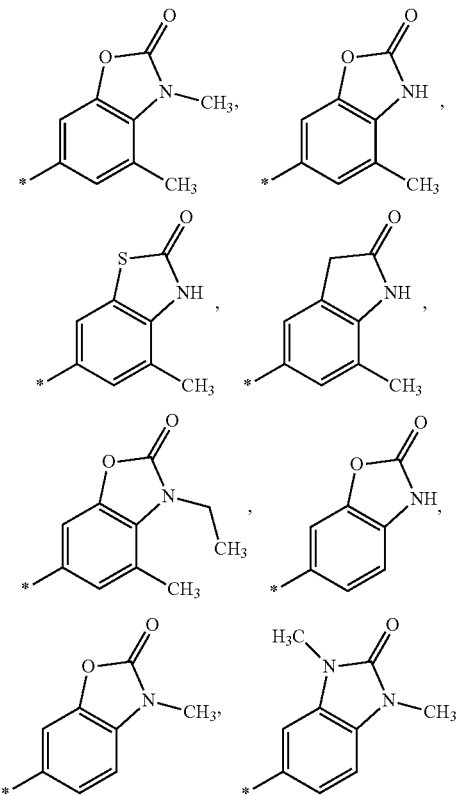
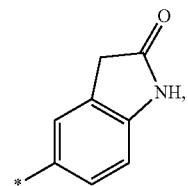
and the ring
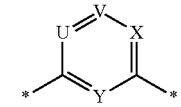
denotes a group selected from
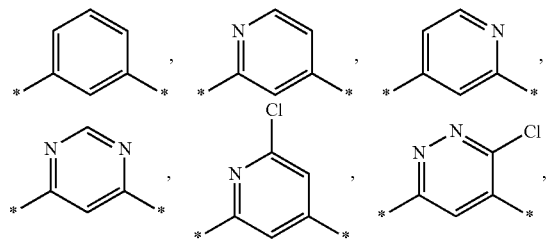
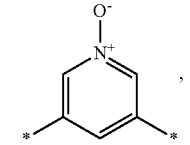
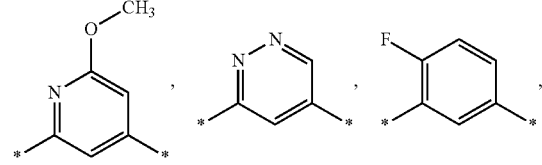
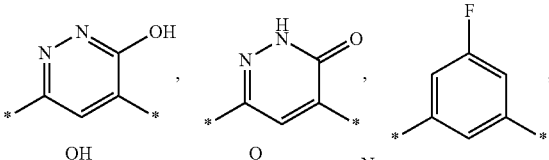
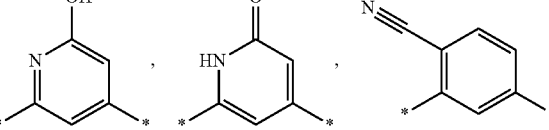
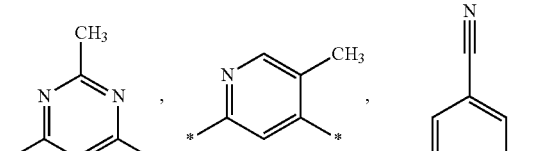
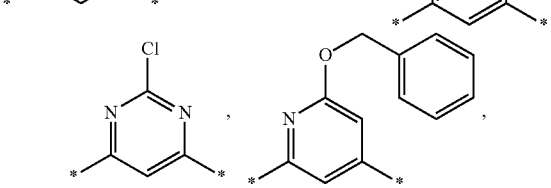

-continued

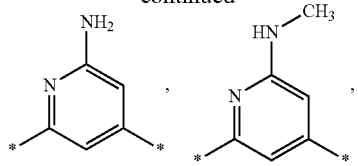

the tautomers, the diastereomers, the enantiomers, the hydrates, the mixtures thereof and the salts thereof and the hydrates of the salts, particularly the physiologically acceptable salts thereof with inorganic or organic acids or bases.

The following compounds are mentioned as examples of most particularly preferred compounds of the above general formula I:

| No. | Structure |
|---|---|
| (1) | 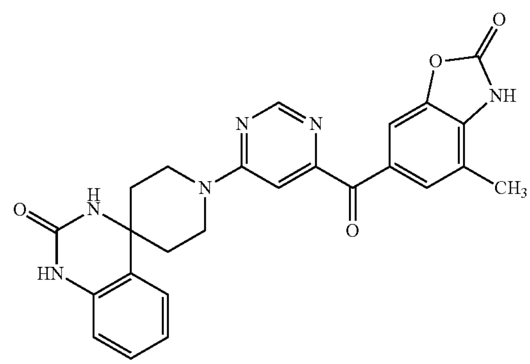 [SMILES: Cc1cc(C(=O)c2cc(N3CCC4(CC3)NC(=O)Nc3ccccc34)ncn2)cc2oc(=O)[nH]c12] |
| (2) | 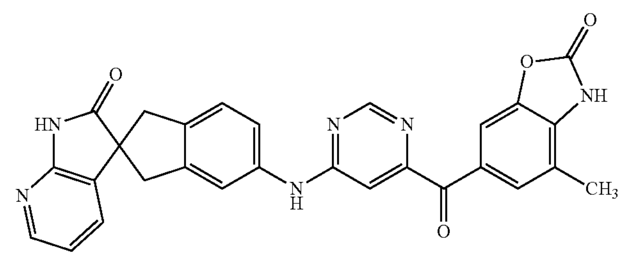 [SMILES: Cc1cc(C(=O)c2cc(Nc3ccc4c(c3)CC3(C4)C(=O)Nc4ncccc43)ncn2)cc2oc(=O)[nH]c12] |
| (3) | 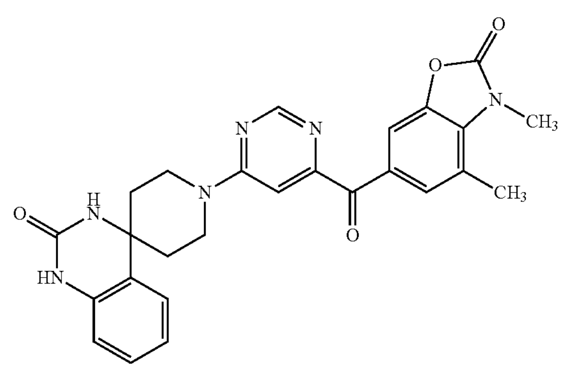 [SMILES: Cc1cc(C(=O)c2cc(N3CCC4(CC3)NC(=O)Nc3ccccc34)ncn2)cc2oc(=O)n(C)c12] |
| (4) | 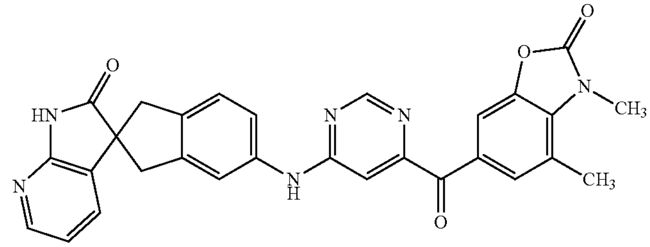 [SMILES: Cc1cc(C(=O)c2cc(Nc3ccc4c(c3)CC3(C4)C(=O)Nc4ncccc43)ncn2)cc2oc(=O)n(C)c12] |

| No. | Structure |
|---|---|
| (5) | 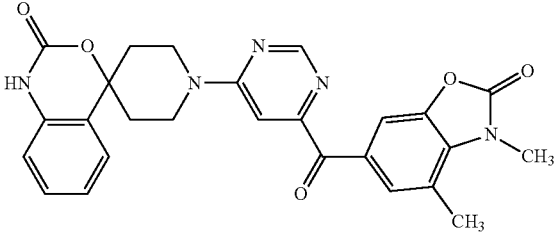 |
| (6) | 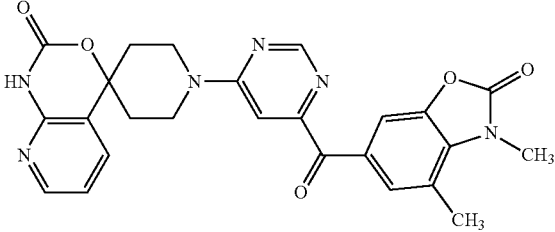 [SMILES: Cc1cc(C(=O)c2cc(N3CCC4(CC3)OC(=O)Nc3ccccc34)ncn2)cc2oc(=O)n(C)c12] |
| (7) | 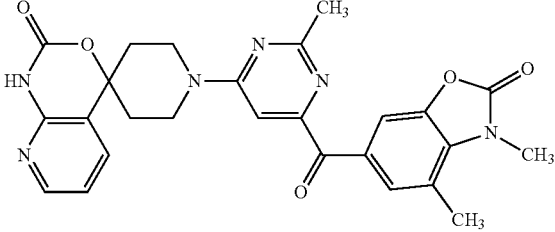 [SMILES: Cc1nc(C(=O)c2cc(C)c3c(c2)oc(=O)n3C)cc(N2CCC3(CC2)OC(=O)Nc2ncccc23)n1] |
| (8) | 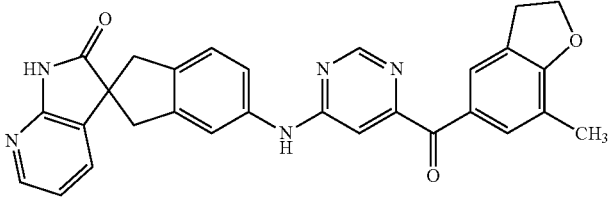 [SMILES: Cc1cc(C(=O)c2cc(Nc3ccc4c(c3)CC3(C4)C(=O)Nc4ncccc43)ncn2)cc2c1OCC2] |
| (9) | 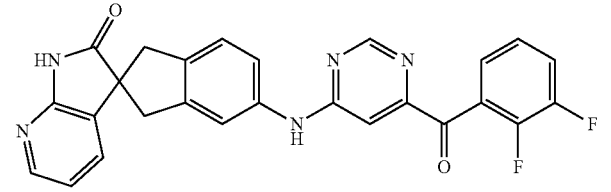 [SMILES: O=C(c1cc(Nc2ccc3c(c2)CC2(C3)C(=O)Nc3ncccc32)ncn1)c1cccc(F)c1F] | the enantiomers, the diastereomers, the hydrates, the mixtures thereof and the salts thereof and the hydrates of the salts, particularly the physiologically acceptable salts thereof with inorganic or organic acids or bases.

Terms and Definitions Used

The present specification of the invention is to be interpreted in accordance with the conventions and rules of chemical bonds.

The compounds included in this invention are those that are also chemically stable.

Unless otherwise stated, all the substituents are independent of one another. If for example there are a plurality of $C_{1-4}$-alkyl groups as substituents in one group, in the case of three $C_{1-4}$-alkyl substituents, independently of one another, one may represent methyl, one ethyl and one n-propyl.

Within the scope of this application, in the definition of possible substituents, these may also be represented in the form of a structural formula. If present, an asterisk (*) in the structural formula of the substituent is to be understood as being the linking point to the rest of the molecule. For example a phenyl group is shown as follows:

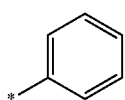 [SMILES: *c1ccccc1]

Moreover, the atom of the substituent that follows the linking point is understood as being the atom at position number 1.

The subject-matter of this invention also includes the compounds according to the invention, including the salts thereof, wherein one or more hydrogen atoms, for example one, two, three, four or five hydrogen atoms, are replaced by deuterium.

By the term "$C_{1-3}$-alkyl" (including those which are a part of other groups) are meant branched and unbranched alkyl groups with 1 to 3 carbon atoms, by the term "$C_{1-4}$-alkyl" are meant branched and unbranched alkyl groups with 1 to 4 carbon atoms and by the term "$C_{1-6}$-alkyl" are meant branched and unbranched alkyl groups with 1 to 6 carbon atoms. Examples include: methyl, ethyl, n-propyl, iso-propyl, n-butyl, iso-butyl, sec-butyl, tert-butyl, pentyl, neopentyl or n-hexyl. The abbreviations Me, Et, n-Pr, i-Pr, n-Bu, i-Bu, t-Bu, etc. may optionally also be used for the above-mentioned groups. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are a part of other groups) are meant branched and unbranched alkylene groups with 1 to 6 carbon atoms and by the term "$C_{1-3}$-alkylene" are meant branched and unbranched alkylene groups with 1 to 3 carbon atoms. Examples include: methylene, ethylene, propylene, 1-methylethylene, butylene, 1-methylpropylene, 1.1-dimethylethylene, 1,2-dimethylethylene, pentylene, 1.1-dimethylpropylene, 2,2-dimethylpropylene, 1,2-dimethylpropylene, 1,3-dimethylpropylene or hexylene. Unless stated otherwise, the definition propylene includes all the possible isomeric forms of the groups in question with the same number of carbons. Thus, for example, propyl also includes 1-methylethylene and butylene includes 1-methylpropylene, 1.1-dimethylethylene, 1,2-dimethylethylene.

The definition for $C_0$-alkylene denotes a bond.

By the term "$C_{2-6}$-alkenyl" (including those which are a part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they comprise at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are a part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they comprise at least one triple bond. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1,2- and 3-butynyl, 1-methyl-1-propynyl, 1-methyl-2-propynyl etc.

By the term "$C_{3-6}$-cycloalkyl" (including those which are a part of other groups) are meant cyclic alkyl groups with 3 to 6 carbon atoms and by the term "$C_{5-6}$-cycloalkyl" are meant cyclic alkyl groups with 5 to 6 carbon atoms. Examples include: cyclopropyl, cyclobutyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{5-6}$-cycloalkenyl" (including those which are a part of other groups) are meant cyclic alkenyl groups with 5 or 6 carbon atoms, which contain an unsaturated bond. Examples include: cyclopentenyl or cyclohexenyl. Unless otherwise stated, the cyclic alkenyl groups may be substituted by one or more groups selected from among methyl, ethyl, iso-propyl, tert-butyl, hydroxy, fluorine, chlorine, bromine and iodine.

By the term "heterocyclyl" or "heterocyclic group" are meant, unless otherwise described in the definitions, stable 5-, 6- or 7-membered monocyclic or 8-, 9-, 10- or 11-membered bicyclic heterocyclic ring systems which do not form an aromatic ring system in at least one ring and besides carbon atoms may carry one to four heteroatoms, which are selected from among nitrogen, oxygen and sulphur. Both nitrogen atoms and sulphur atoms may optionally be oxidised and nitrogen atoms may be quaternised. The heterocyclic ring may contain one or two carbonyl, thiocarbonyl or cyanoimino groups adjacent to a nitrogen atom. The heterocycles mentioned previously may be attached to the rest of the molecule via a carbon atom or a nitrogen atom.

Unless otherwise stated, the heterocycles may be substituted by one or more groups selected from among:
(a) OH, $NO_2$, CN, $OCF_3$, $OCHF_2$, $OCH_2F$, $NH_2$,
(b) halogen, preferably fluorine or chlorine,
(c) $C_{1-6}$-alkyl, preferably $C_{1-3}$-alkyl, particularly preferably ethyl, methyl, iso-propyl or tert-butyl,
(d) —$SO_2$—O—$C_{1-3}$-alkyl, preferably —O-methyl,
(e) —O—$C_{1-3}$-alkyl, preferably —O-methyl or —O-ethyl,
(f) COOH, COO—$C_{1-3}$-alkyl, preferably CO—O-methyl or CO—O-ethyl, while the groups may be identical or different.

The following compounds are mentioned by way of example, but the invention is not restricted to them: azetidine, oxetane, thietane, thietane dioxide, tetrahydrofuran, dihydrofuran, dioxolane, imidazolidine, imidazoline, imidazolidinone, dihydroimidazolone, oxazoline, oxazolidine, oxazolidinone, pyrrolidinone, dihydropyrazole, pyrrolidine, pyrroline, morpholine, tetrahydropyridine, dihydropyran, tetrahydropyran, dioxane, piperazine, piperidine, piperazinone, piperidinone, pyran, thiomorpholine-S-oxide, thiomorpholine-S-dioxide, thiomorpholine, dihydroxazine, morpholinedione, morpholinethione, perhydrothiazinedioxide, ∈-caprolactam, oxazepanone, diazepanone, thiazepanone, perhydroazepine, dihydroquinazolinone, dihydroindole, dihydroisoindole, benzoxazolone, benzimidazolone, chromanone, tetrahydroquinoline, tetrahydrobenzoxazole, tetrahydrobenzisoxazole, tetrahydrobenzthiophene, tetrahydrothieno-pyridine, tetrahydrobenzofuran, tetrahydro-oxazolopyridine, tetrahydro-isoxazolopyridine.

The following heterocycles are preferred according to the invention:

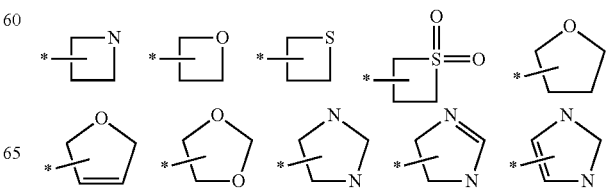

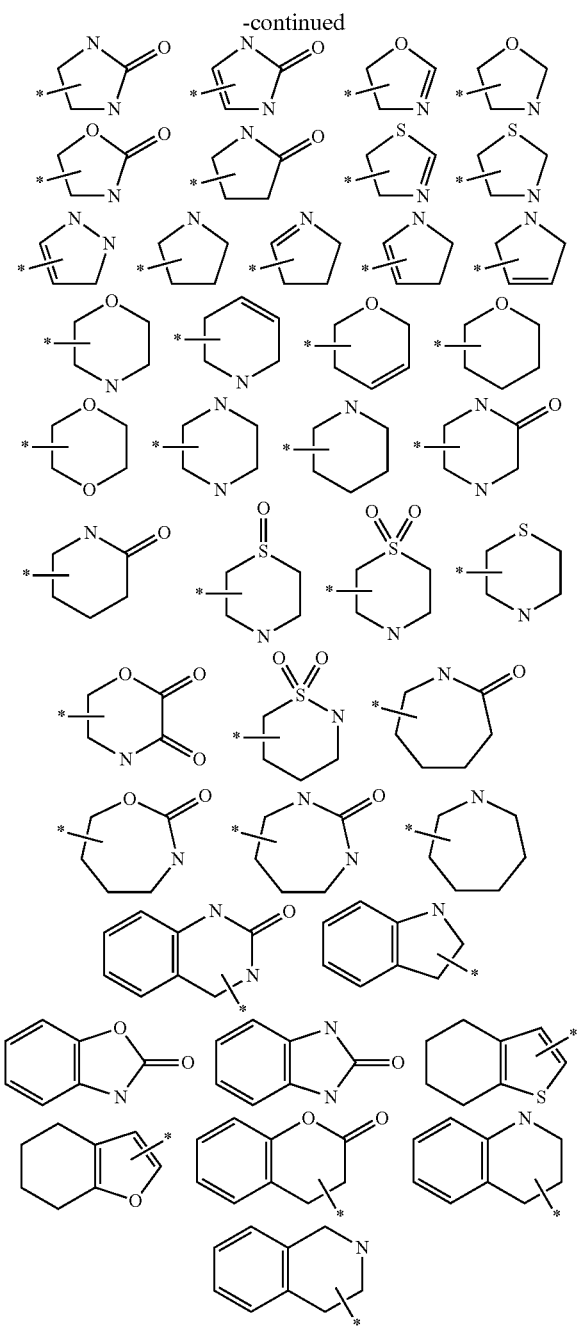

By the term "aryl" (including those which are a part of other groups) are meant monocyclic aromatic ring systems with 6 carbon atoms or bicyclic aromatic ring systems with 10 carbon atoms. Examples include phenyl, 1-naphthyl or 2-naphthyl; the preferred aryl group is phenyl.

Unless otherwise stated, the aromatic groups may be substituted by one or more groups selected from among:
(a) OH, $NO_2$, CN, $OCF_3$, $OCHF_2$, $OCH_2F$, $NH_2$,
(b) halogen, preferably fluorine or chlorine,
(c) $C_{1-6}$-alkyl, preferably $C_{1-3}$-alkyl, particularly preferably ethyl, methyl, iso-propyl or tert-butyl,
(d) —$SO_2$—O—$C_{1-3}$-alkyl, preferably —O-methyl,
(e) —O—$C_{1-3}$-alkyl, preferably —O-methyl or —O-ethyl,
(f) COOH, CO—O—$C_{1-3}$-alkyl, preferably CO—O-methyl or CO—O-ethyl,
while the groups may be identical or different.

By the term "heteroaryl" are meant stable five- or six-membered heterocyclic aromatic groups or 8- to 10-membered bicyclic heteroaryl rings that may contain in each ring one, two or three heteroatoms, selected from among oxygen, sulphur and nitrogen, and additionally sufficient conjugated double bonds to form an aromatic system. Examples of five- or six-membered heterocyclic aromatic groups are as follows, but the invention is not restricted to these:

furan, pyrrole, thiophene, pyrazole, imidazole, oxazole, thiazole, isothiazole, isoxazole, oxadiazole, triazole, tetrazole, furazan, thiadiazole, pyridine, pyrimidine, pyrazine, pyridazine, triazine.

The following five-membered heterocyclic aromatic groups are preferred according to the invention:

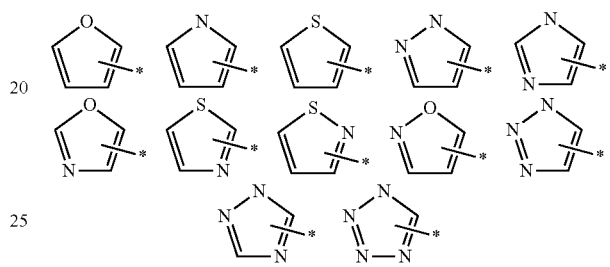

The following six-membered heterocyclic aromatic groups are preferred according to the invention:

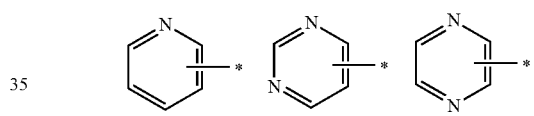

Examples of 9- or 10-membered bicyclic heteroaryl rings are as follows, but the invention is not restricted to these:

indole, isoindole, indazole, indolizine, benzofuran, benzthiophene, benzimidazole, benzoxazole, benzothiazole, benzotriazole, benzisoxazole, benzisothiazole, quinoline, isoquinoline, cinnolin, phthalazine, quinoxaline, quinazoline, pyridopyrimidine, pyridopyrazine, pyridopyridazine, pyrimidopyrimidine, pteridine, purine, quinolizine, benzoxazolecarbonitrile, quinoline, isoquinoline, quinolizine, pteridine, purine, quinolizine, benzoxazole-carbonitrile.

The following bicyclic heteroaryl rings are preferred according to this invention:

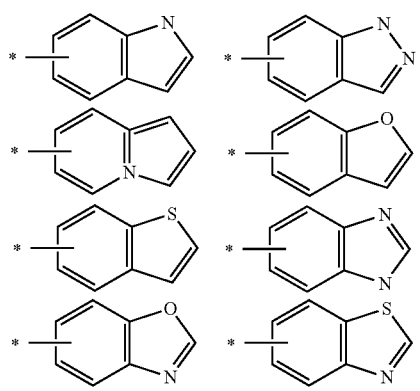

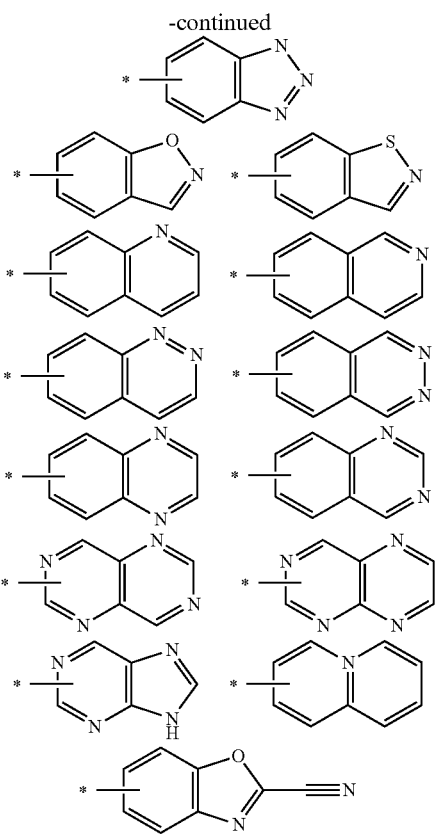

Unless otherwise stated, the heteroaryls previously mentioned may be substituted by one or more groups selected from among:
(a) OH, $NO_2$, CN, $OCF_3$, $OCHF_2$, $OCH_2F$, $NH_2$,
(b) halogen, preferably fluorine or chlorine,
(c) $C_{1-6}$-alkyl, preferably $C_{1-3}$-alkyl, particularly preferably ethyl, methyl, iso-propyl or tert-butyl,
(d) —$SO_2$—O—$C_{1-3}$-alkyl, preferably —O-methyl,
(e) —O—$C_{1-3}$-alkyl, preferably —O-methyl or —O-ethyl,
(f) COOH, CO—O—$C_{1-3}$-alkyl, preferably CO—O-methyl or CO—O-ethyl,
while the groups may be identical or different.

Bicyclic heteroaryl rings may preferably be substituted in the phenyl group.

By the term "halogen" are meant fluorine, chlorine, bromine or iodine atoms.

Compounds of general formula I may have acid groups, mainly carboxyl groups, and/or basic groups such as e.g. amino functions. Compounds of general formula I may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali or alkaline earth metal hydroxides, e.g. sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine, dicyclohexylamine, inter alia.

The compounds according to the invention may be present as racemates, provided that they have only one chiral element, but may also be obtained as pure enantiomers, i.e. in the (R) or (S) form.

Compounds with a carbon double bond may be present in both the E and Z form.

The following nitrogen-containing heteroaryls may be present in different tautomeric forms:

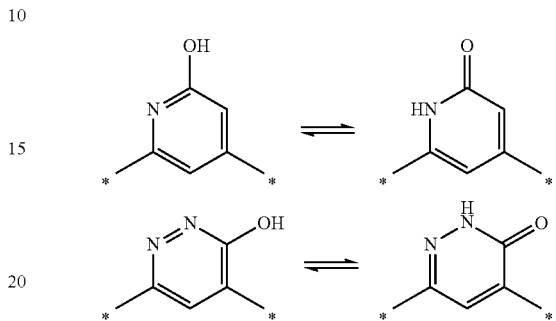

This means that the compound prepared in each case is not restricted to one tautomeric form but encompasses all tautomeric forms.

However, the application also includes the individual diastereomeric pairs of antipodes or mixtures thereof, which are obtained if there is more than one chiral element in the compounds of general formula I, as well as the individual optically active enantiomers of which the above-mentioned racemates are made up.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids.

So-called prodrugs of compounds of general formula I are also encompassed by this invention. The term prodrug is used to denote any molecule that releases the active principle of general formula I in-vivo after administration to mammals. The prodrug may have little or no pharmacological activity per se, but releases the active principle of general formula I in-vivo after administration and this has the activity described. Prodrugs for compounds of general formula I may be prepared by modifying suitable functional groups in the compound of general formula I, as known to the skilled man in this field. (H. Bundgaard (Editor), Design of Prodrugs. (1986), Elsevier)

This invention also includes those metabolites that are derived from the compounds of general formula I. By metabolites are meant, in this context, compounds that are formed in-vivo from the compound of general formula I after administration. Examples of metabolites include:
methyl groups of the compound of general formula I may be converted into the corresponding hydroxymethyl groups. (—$CH_3$->—$CH_2OH$)
alkoxy groups of the compound of general formula I may be converted into the corresponding hydroxyl groups. (—OR->—OH)
secondary amines of the compound of general formula I may be converted into the corresponding primary amines. (—$NR_1R_2$->—$NHR_1$ or —$NHR_2$)
nitrogen atoms of the compound of general formula I may be converted into the corresponding nitrogen oxides. (=N—->=$N^+$—($O^-$)—)

Methods of Preparation

The invention also relates to a process for preparing the compounds of general formula I, wherein the substituents have the meanings stated earlier.

Some methods of preparing the compounds of general formula I according to the invention

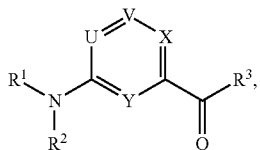
(I)

wherein U, V, X, Y, $R^1$, $R^2$ and $R^3$ are as hereinbefore defined, are illustrated in the following synthesis schemes and Examples.

In some cases the order of carrying out the reaction schemes may be varied in order to simplify the reactions or prevent unwanted by-products. The Examples that follow are provided to make the invention comprehensible. The Examples are intended to illustrate the invention and should in no way restrict it.

In some cases the end product may be further derivatised, e.g. by manipulation of the substituents. These manipulations may be generally known to the skilled man, such as oxidation, reduction, alkylation, acylation and hydrolysis, but need not be restricted to the above.

Starting compounds are prepared by processes which are either known in the art or described herein. Before the reaction is carried out corresponding functional groups in the compounds may be protected by conventional protective groups. These protective groups may be cleaved again at a suitable stage within the reaction sequence using methods known in the art (P. G. M. Wuts, T. W. Greene "Greene's Protective Groups in Organic Synthesis", 4th ed., Wiley Interscience).

The compounds according to the invention may be prepared according to the schemes and specific examples provided or corresponding modifications, using known and/or available starting materials, reagents and conventional methods of synthesis. Modifications to these reactions which are known to the skilled man but not described in detail here may also be implemented.

The following methods of preparing the compounds of general formula I according to the invention and their precursors have proved particularly suitable:

The starting compounds are commercially available or are prepared by methods described in the literature, known to the skilled man in the field or described herein. Before the reaction is carried out any corresponding functional groups in the compounds may be protected by conventional protective groups. These protective groups may be cleaved again at a suitable stage within the reaction sequence using methods known in the art.

In the reactions described below, any reactive groups present such as hydroxy, carboxy, amino, alkylamino, amide or imino groups may be protected during the reaction by conventional protective groups that are cleaved again after the reaction.

For example a suitable protective group for a hydroxy group may be the methoxy, benzyloxy, trimethylsilyl, acetyl, benzoyl, tert.-butyl, trityl, benzyl or tetrahydropyranyl group, suitable protective groups for a carboxyl group may be the trimethylsilyl, methyl, ethyl, tert.-butyl, benzyl or tetrahydropyranyl group, and suitable protective groups for an amide group may be the N-methoxymethyl- (MOM), N-benzyloxymethyl (BOM), N-(trimethylsilyl)ethoxymethyl (SEM), N-tert-butyldimethylsiloxymethyl, N-tert-butyldimethylsilyl (TBDMS), N-triisopropylsilyl- (TIPS), N-benzyl, N-4-methoxybenzyl (PMB), N-triphenylmethyl (Trt), N-tert-butoxycarbonyl (BOC), N-benzyloxycarbonyl (Cbz) or N-trimethylsilylethylsulphonyl (SES)

a suitable protective group for an amino, alkylamino or imino group may be the acetyl, trifluoroacetyl, benzoyl, ethoxycarbonyl, tert.-butoxycarbonyl, benzyloxycarbonyl, benzyl, methoxybenzyl or 2,4-dimethoxybenzyl group and additionally, for the amino group, the phthalyl group.

Other protective groups and their cleavage are described in T. W. Greene, P. G. M. Wuts, "Protective Groups in Organic Synthesis", Wiley, 2006.

Any protecting group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide, or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures of between 0 and 50° C., but preferably at ambient temperature.

A methoxy group is conveniently cleaved in the presence of boron tribromide in a solvent such as methylene chloride at temperatures between −35 and −25° C.

A 2,4-dimethoxybenzyl group is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxan or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

A methoxymethyl group may be cleaved in the presence of an acid such as concentrated hydrochloric acid in a solvent such as dimethoxyethane. Alternatively an acid such as trifluoroacetic acid may also be used without a solvent.

An N-(trimethylsilyl)ethoxymethyl group may be cleaved in the presence of TBAF and 1,3-dimethyl-3,4,5,6-tetrahydro-2(1H)-pyrimidone. Alternatively the SEM protective group may also be cleaved with an acid such as hydrogen chloride in an organic solvent such as dioxane or ethanol.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine at temperatures between 0 and 100° C., preferably at ambient temperature and under an inert gas, or by treating with a catalytic amount of tris-(triphenylphosphine)-rhodium (I)chloride in a solvent such as aqueous ethanol and optionally in the presence of a base such as 1,4-diazabicyclo[2,2,2]octane at temperatures between 20 and 70° C.

The following methods of preparing the compounds of general formula I according to the invention and their precursors have proved particularly suitable:

An end compound of general formula I wherein U, V, X, Y, $R^1$, $R^2$ and $R^3$ are as hereinbefore defined may be obtained by reacting a compound of general formula (1-1) with an electron-poor compound of general formula (1-2) that has a leaving group LG. Halides, preferably chlorides and bromides, —$SO_2CH_3$, —$OSO_2CH_3$, —$OSO_2C_6H_4$—$CH_3$ or —S—$CH_3$ (—S—$CH_3$ requires further reaction with an organic peroxide in order to be converted into the actual leaving group) etc. may act as the leaving group LG, but it is not restricted to this list. The use of chlorides is most particularly preferred.

Scheme 1:

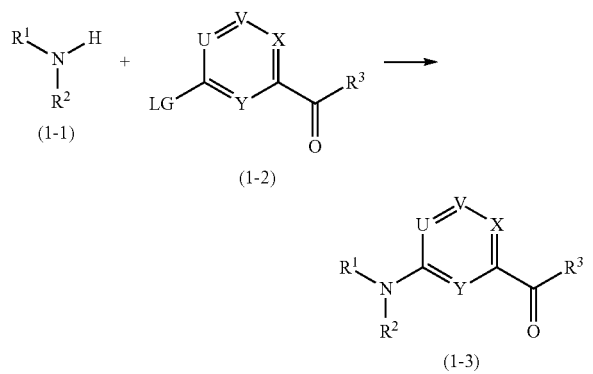

The reaction may be carried out by nucleophilic aromatic substitution in an inert solvent using an auxiliary base in a temperature range of from 0° C. to the reflux temperature of the solvent. The reaction is carried out in a suitable inert solvent, such as tetrahydrofuran, toluene, xylene, dialkylformamide (particularly preferably dimethylformamide), cyclic amide (particularly preferably N-methyl-pyrrolidone), 1,4-dioxane, acetonitrile or in inert solvent mixtures. Suitable auxiliary bases include tertiary amines such as triethylamine or ethyldiisopropylamine, alkali metal carbonates such as potassium carbonate or sodium carbonate, sodium hydride (NaH) or lithium diisopropylamide (LDA). The inert solvent used must be compatible with the base used. The reaction is preferably carried out in dimethylformamide, at temperatures between ambient temperature and the reflux temperature of the solvent, in the presence of a tertiary amine base.

Alternatively the structures of general formula (1-3) shown in Scheme 1 wherein U, V, X, Y, $R^1$, $R^2$ and $R^3$ are as hereinbefore defined may be synthesised by transition metal-catalysed reactions. A compound of general formula (1-1) may react with a compound of general formula (1-2) that has a leaving group LG in an inert solvent in the presence of a catalyst and an auxiliary base. In addition, a suitable ligand may be used for the catalyst. Chlorides, bromides, iodides, trifluoroacetates, trifluoromethanesulphonates, methanesulphonates and toluenesulphonates, but this list is not restrictive. Xylene, tetrahydrofuran, dimethylformamide, dimethoxyethane, toluene, benzene, 1,4-dioxane, acetonitrile or solvent mixtures may be used as inert solvents. The preferred solvent is xylene. Suitable bases are particularly amine bases such as e.g. triethylamine or diisopropylethylamine or also inorganic bases such as caesium carbonate, caesium acetate, potassium carbonate, sodium carbonate or potassium phosphate. Preferred reaction temperatures are from RT to the reflux temperature of the solvent at normal pressure. Typical catalysts are e.g. transition metal catalysts, such as e.g. palladium catalysts of the tris(dibenzylideneacetone)-dipalladium(0), tetrakis-(triphenylphosphine)-palladium(0), palladium-(II)-acetate, $Pd(PPh_3)_2Cl_2$, $Pd(CH_3CN)_2Cl_2$, $Pd(dppf)Cl_2$ or palladium(II)-chloride type. Typical ligands are e.g. triphenylphosphine, triphenylarsene, BINAP, XPhos, XantPhos, or 2-(di-tert-butylphosphino)biphenyl.

Compounds of general formula (2-4), wherein U, V, X, Y, $R^1$, $R^2$ and $R^3$ are as hereinbefore defined, may be prepared as shown in Scheme 2.

Scheme 2:

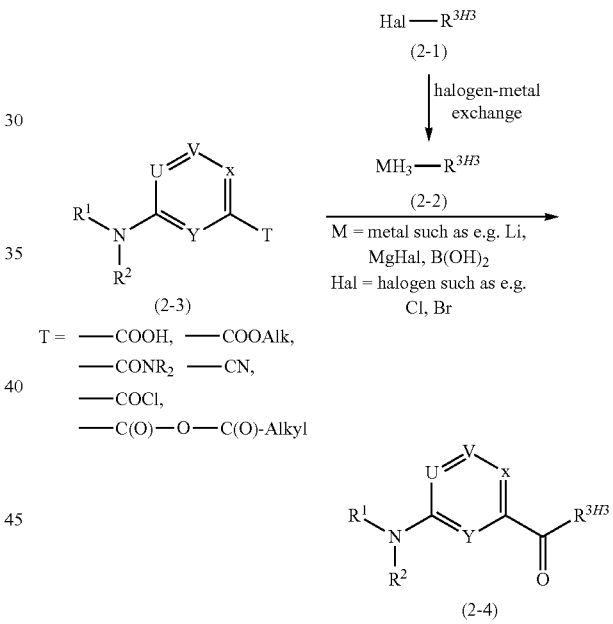

The reaction starts from a compound of general formula (2-1) wherein Hal denotes a halogen atom, preferably chlorine, bromine or iodine. The Grignard or lithiated compound of general formula (2-2) may be prepared from the correspondingly halogenated compound of general formula (2-1) either by a so-called halogen-metal exchange or by inserting the metal in a halogen-carbon bond. In order to synthesise the corresponding lithiated compound of general formula (2-2) the halogen-metal exchange may be carried out for example with an organo-lithium compound such as e.g. n-, sec- or tert.-butyllithium. The corresponding magnesium compounds (Grignard compounds) may also be obtained by a halogen-metal exchange with a corresponding Grignard reagent such as e.g. isopropyl- or sec-butyl-magnesium bromide or isopropyl- or sec-butyl-magnesium chloride or diisopropyl- or di-sec-butylmagnesium with or in the presence of a salt such as e.g. lithium chloride that may accelerate the metallisation process. The corresponding transmetallising organo-magnesium compound may also be synthesised in-situ from corresponding precursors (cf. e.g. Angew. Chem. 2004, 116, 3396-3399 and Angew. Chem. 2006, 118, 165-169 and references contained therein). In addition, -ate complexes of the organo-magnesium compounds may also be used, resulting from the combination of e.g. butylmagnesium chloride or bromide or isopropyl-magnesium chloride or bromide and butyllithium. (cf. Angew. Chem. 2000, 112, 2594-2596 and Tetrahedron Lett. 2001, 42, 4841-4844 and references contained therein). The halogen-metal exchange is preferably carried out between −100° C. and 40° C., most particularly preferred is a temperature range of from −80° C. to 10° C. in an inert solvent, preferably alkylether (most particularly preferably diethyl ether), cyclic ether (most particularly preferably 1,4-dioxane or tetrahydrofuran), toluene, hexane or solvent mixtures thereof. The magnesium or organolithium compounds thus obtained may optionally be transmetallised with metal salts such as e.g. cerium trichloride, zinc chloride or zinc bromide, indium chloride or indium bromide, in order to synthesise alternative organometallic compounds of general formula (2-2) that are also suitable for the reaction described. Alternatively the organo-metallic compound (2-2) may also be prepared by inserting a metal into a carbon-halogen bond. Lithium or magnesium are suitable elemental metals for this transformation. The insertion reaction is preferably carried out between −80° C. and 100° C., while most particularly preferred is a temperature range from −70° C. to 40° C. in an inert solvent, preferably alkylether (most particularly preferably diethyl ether), cyclic ether (most particularly preferably 1,4-dioxane or tetrahydrofuran), toluene, hexane or solvent mixtures thereof. In cases where no spontaneous reaction takes place it may be necessary to activate the metal with e.g. 1,2-dibromoethane, iodine, trimethylsilyl chloride, acetic acid, hydrogen chloride or ultrasound. The reaction of the organo-metallic compound of general formula (2-2) with a compound (2-3) is preferably carried out in a temperature range from −100° C. to 100° C., while a temperature range from −80° C. to 50° C. is particularly preferred. The reaction is carried out in an inert solvent, such as e.g. preferably alkylether (most particularly preferably diethyl ether, dimethoxyethan), cyclic ether (most particularly preferably 1,4-dioxane or tetrahydrofuran), aromatic hydrocarbons (most particularly preferably toluene or benzene), hexane or solvent mixtures thereof. All the reactions may be carried out in the air, but it is preferable to carry them out in a protective gas atmosphere such as argon or nitrogen. It may prove advantageous to temporarily protect the functional group in compound (2-3).

The lithium-substituted or magnesium-substituted compound of general formula (2-2) may react in a desired manner with a compound of general formula (2-3) that contains a carboxyl group or derivatives thereof such as esters, nitriles, carboxylic acid chlorides or amides, such as e.g. grapevine amides. These reactions may often be carried out without any additional transition metal catalyst or transmetallisation to another metal such as e.g. cerium, indium or zinc. In some cases, however, the two modifications mentioned may also prove advantageous. Aromatic boric acids, esters derived therefrom, dialkylarylboranes or aryltrifluoroborates may be reacted with acid chlorides or carboxylic acids in the presence of a transition metal, such as e.g. palladium, as catalyst, to obtain the corresponding ketones (V. Polackova, St. Tama, I. Augustinova, Iveta; Tetrahedron; 2006; 62; 50; 11675-11678 and references cited therein and R. Kakino, H. Narahashi, I. Shimizu, A. Yamamoto, Bull. Chem. Soc. Jpn., 2002, 75, 1333-1345).

The corresponding boron-substituted compound, such as e.g. boric acids, dialkylarylboranes or boric acid ester can be synthesised from the metallised species by reaction with a boron electrophil such as e.g. a boric acid ester or derivatives thereof. Boron-substituted compounds may also be synthesised from the halogenated or pseudohalogenated precursor molecules using a transition metal catalyst, preferably palladium, and a boron or borolan compound. (Tetrahedron Lett. 2003, 4895-4898 and references cited therein).

The metallisation and/or coupling reaction may also be carried out in microreactors and/or in the micromixer. The addition reactions may be carried out without any further additions or, in the case of unreactive reactants, promoters such as e.g. $BF_3 \cdot OEt_2$ may also be added (cf. M. Schlosser, Organometallics in Synthesis, John Wiley & Sons, Chichester/New York/Brisbane/Toronto/Singapore, 1994).

The halogenated compounds of general formula (2-1) are either commercially available or may be synthesised by methods known in the field of organic chemistry or described in the specialist literature (cf. e.g. J. March, Advanced Organic Reactions, Reactions Mechanism, and Structure, 4th Edition, John Wiley & Sons, Chichester/New York/Brisbane/Toronto/Singapore, 1992 and literature cited therein). The use of transition metals and organometallic compounds for the synthesis is described in detail in monographs (cf. e.g. L. Brandsma, S. F. Vasilevsky, H. D. Verkruijsse, Application of Transition Metals Catalysts in Organic Synthesis, Springer-Verlag, Berlin/Heidelberg, 1999; M. Schlosser, Organometallics in Synthesis, John Wiley & Sons, Chichester/New York/Brisbane/Toronto/Singapore, 1994, P. J. Stang, F. Diederich, Metal-Catalyzed Cross-Coupling Reactions, Wiley-VCH, Weinheim, 1997 and references contained therein.)

A method of synthesising compounds of general formula (3-4) wherein U, V, X, Y and $R^3$ are as hereinbefore defined is illustrated in Scheme 3.

Scheme 3:

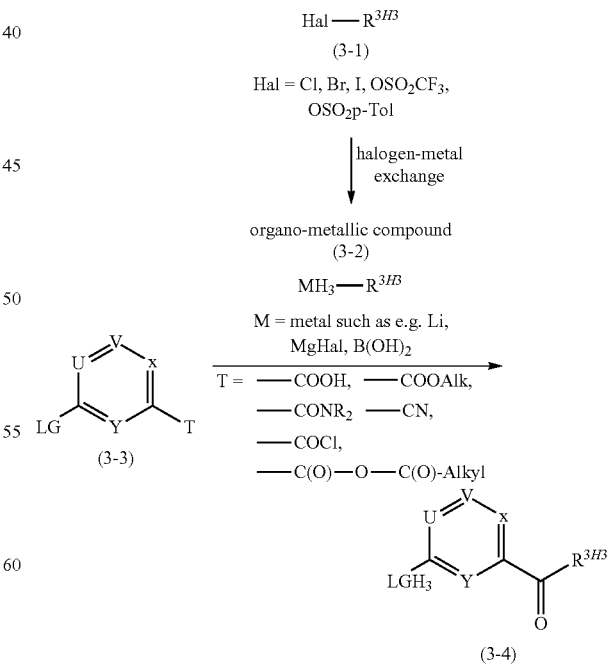

Starting from a halogenated compound (particularly preferred are the chlorides, bromides and iodides) of general formula (3-1) the corresponding lithium or magnesium-substituted compound may be synthesised by a halogen-metal exchange reaction, e.g. with butyllithium, isopropylmagnesium halide or diisopropylmagnesium or by insertion of an elemental metal into the halogen-carbon bond. The corresponding boron-substituted compounds, such as e.g. boric acid, dialkylarylborane or boric acid ester, can be synthesised from the metallised species by reaction with a boron electrophil such as e.g. a boric acid ester or derivatives thereof. Boron-substituted compounds may also be synthesised from the halogenated or pseudohalogenated precursor molecules using a transition metal catalyst, preferably palladium, and a boron or borolan compound (Tetrahedron Lett. 2003, 4895-4898 and references cited therein). The lithium-substituted or magnesium-substituted compound of general formula (3-2) may be added to a compound of general formula (3-3) that contains a carboxyl group or derivatives thereof such as esters, nitriles, carboxylic acid chlorides or amides, such as e.g. grapevine amides. These reactions may often be carried out without any additional transition metal catalyst or transmetallisation to another metal such as e.g. cerium, indium or zinc. In some cases, however, the two modifications mentioned may also prove advantageous. Aromatic boric acids, esters derived therefrom, dialkylarylboranes or aryltrifluoroborates may be reacted with acid chlorides or carboxylic acids in the presence of a transition metal, such as e.g. palladium, as catalyst, to obtain the corresponding ketones (V. Polackova, St. Toma, I. Augustinova, Iveta; Tetrahedron; 2006; 62; 50; 11675-11678 and references cited therein and R. Kakino, H. Narahashi, I. Shimizu, A. Yamamoto, Bull. Chem. Soc. Jpn., 2002, 75, 1333-1345).

Compounds of general formula (4-3), wherein U, V, X, Y and $R^3$ are as hereinbefore defined, may be prepared as shown in Scheme 4.

Scheme 4:

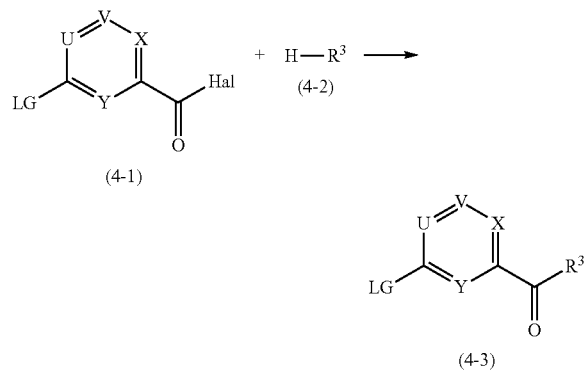

Hal = Halogen

A compound of general formula (4-1) that has a leaving group LG and an acid halide group may be reacted with an aromatic compound of general formula (4-2) under Friedel-Crafts acylation conditions or variations thereof. Friedel-Crafts reactions are carried out in the presence of a catalyst which is used in either catalytic or stoichiometric amounts. Suitable catalysts are, in particular, $AlCl_3$, $FeCl_3$, iodine, iron, $ZnCl_2$, sulphuric acid or trifluoromethanesulphonic acid. Instead of the acid halide the corresponding carboxylic acid, anhydride, ester or nitrile may also be used. The reaction is preferably carried out in halogenated hydrocarbons. Dichloromethane and 1,2-dichloroethane are particularly preferred. Friedel-Crafts reactions are carried out in a temperature range of from −30° C. to 120° C., preferably from 30° C. to 100° C. However, the reactions may also be carried out without a solvent. The reactions may also be carried out in the microwave.

Compounds of general formula (5-3), wherein U, V, X, Y, $R^1$, $R^2$ and $R^3$ are as hereinbefore defined, may be prepared as shown in Scheme 5.

Scheme 5:

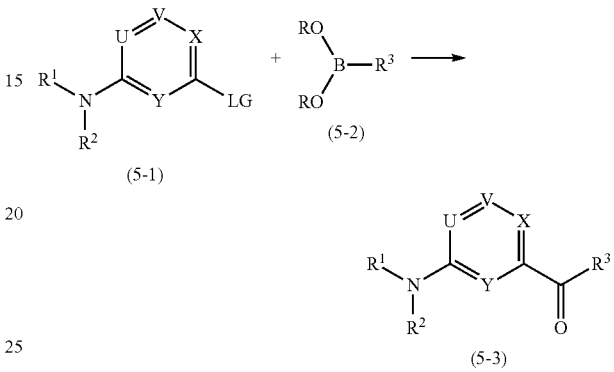

Analogously to a method of T. Ishiyama et al. (J. Org. Chem., 1998, 63, 4726) a compound of general formula (5-1) that has a leaving group LG may be reacted with a boron-substituted compound, such as boric acid (R=H), boric acid ester (R=alkyl) dialkylarylborane in the presence of a catalyst and a base, in an inert solvent and a carbon monoxide atmosphere, preferably in a temperature range from ambient temperature to the reflux temperature of the solvent. Preferably, elevated reaction temperatures from 80° C. to 110° C. are used, under elevated carbon monoxide pressure. A suitable ligand may additionally be used for the catalyst. Alkali metal iodides such as sodium iodide or potassium iodide may be added as additives. Bromides, iodides, trifluoroacetates, trifluoromethanesulphonates, methanesulphonates and toluenesulphonates may act as the leaving group LG, although this list is not restrictive. The inert solvents used may be xylene, tetrahydrofuran, dimethylformamide, dimethoxyethane, toluene, benzene, anisole, 1,4-dioxane, acetonitrile or solvent mixtures. The preferred solvent is anisol. Suitable bases are inorganic bases such as caesium carbonate, caesium acetate, potassium carbonate, sodium carbonate or potassium phosphate. The reactions are carried out in a carbon monoxide atmosphere, in which the carbon monoxide pressure may be 1 to 50 bar. Typical catalysts are e.g. palladium catalysts such as tris-(dibenzylideneacetone)-dipalladium(0), tetrakis-(triphenylphosphine)-palladium(0), palladium-(II)-acetate, $Pd(PPh_3)_2Cl_2$, $Pd(CH_3CN)_2Cl_2$, $Pd(dppf)Cl_2$ or palladium (II)-chloride. Typical ligands are e.g. triphenylphosphine, tricyclohexylphosphine, tri-tert-butylphosphine, triphenylarsene, 2,2'-bis(diphenylphosphino)-1,1-binaphthyl (BINAP), 2-di-tert-butylphosphino-2',4',6'-triisopropylbiphenyl (XPhos), 4,5-bis-diphenylphosphanyl-9,9-dimethyl-9H-xanthene (XantPhos), or 2-(di-tert-butylphosphino)biphenyl, 1,1'-bis(diphenylphosphino)ferrocene (Dppf), 1,2-bis(diphenylphosphino)ethane (dppe), 1,3-bis (diphenylphosphino)propane(dppp) and 1,4-bis (diphenylphosphino)butane (dppb).

It is particularly preferable to use $Pd(PPh_3)_2Cl_2$ as catalyst, potassium carbonate as base, 1 bar of carbon monoxide, potassium iodide as additive and anisole as solvent. The corresponding boron-substituted compounds are either commercially obtainable or can be synthesised from metallised compounds by reaction with a boron electrophil such as e.g. a boric acid ester or a derivative thereof. Moreover, the boron-substituted compounds may be prepared from the corresponding halogenated or pseudohalogenated precursor molecules in a transition metal-catalysed reaction, e.g. with palladium and a diborolane or borolane compound. (Tetrahedron Lett. 2003, 4895-4898 and references cited therein).

A method of synthesising compounds of general formula (6-3), wherein U, V, X, Y and $R^3$ are as hereinbefore defined, is shown in Scheme 6:

Scheme 6:

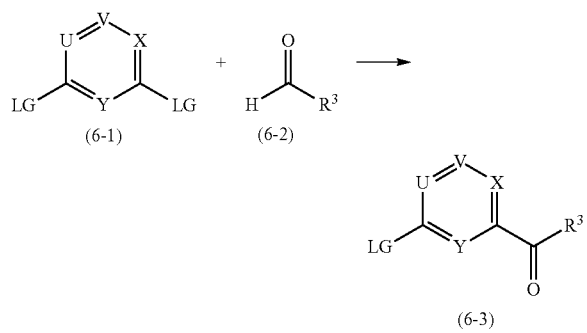

Analogously to a method of A. Miyashita et al. (Heterocycles, 1997, Vol. 45, No. 11, 2159-2173) compounds of general formula (6-1) that have a leaving group LG can be reacted with aromatic aldehydes in the presence of a catalyst and a base in inert solvents to obtain compounds of general formula (6-3). Fluorides, chlorides, bromides, iodides, trifluoromethanesulphonates, methanesulphonates and toluenesulphonates may act as the leaving group LG, but the list is not restrictive. Particularly preferred are chlorides and bromides. Cyclic ethers (preferably tetrahydrofuran) and dialkylformamides (preferably dimethylformamide), may be used as inert solvents. Suitable catalysts are azolium salts, such as 1,3-dimethylimidazolium iodide or 1,3-dimethylbenz-imidazolium iodide. Suitable bases are metal hydrides. Sodium hydride is most particularly preferred. The reactions are carried out in a temperature range from RT to the reflux temperature of the solvent. Elevated temperatures are preferred. The reaction may also be carried out with sodium p-tolylsulphinate instead of azolium salts and base, in the presence of an alkali metal cyanide (preferably potassium cyanide) in an inert solvent at elevated temperatures. (A. Miyashita et al., Heterocycles, 1998, Vol. 47, No. 1, 407-414).

Compounds of general formula (7-4) wherein U, V, X, Y and $R^3$ are as hereinbefore defined, as shown in Scheme 7, may be prepared analogously to A. Miyashita et al., (Heterocycles, 1997, Vol. 45, No. 11, 2159-2173) and the literature cited therein.

Scheme 7:

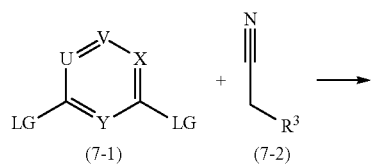

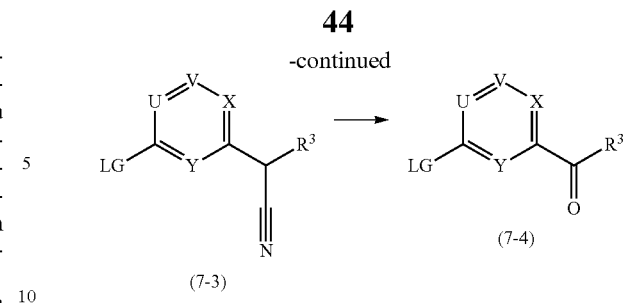

Compounds of general formula (7-1) that have a leaving group LG may be reacted with 2-arylacetonitrile or 2-heteroarylacetonitrile in the presence of a base in an inert solvent to obtain compounds of general formula (7-3). Fluorides, chlorides, bromides, iodides, trifluoromethanesulphonates, methanesuiphonates and toluenesulphonates may act as the leaving group LG, but the list is not restrictive. Particularly preferred are chlorides and bromides. The inert solvent may be a dialkylformamide (preferably dimethylformamide). Metal hydrides are suitable as the base. Sodium hydride is most particularly preferred. The reactions are carried out in a temperature range from RT to the reflux temperature of the solvent. Preferably the reactions are carried out at elevated temperatures.

The compounds of general formula (7-4) are synthesised by oxidative decyanisation of compounds of general formula (7-3). Oxidative decyanisations are carried out in inert solvents through which oxygen gas is passed in the presence of a base. Cyclic ethers (preferably tetrahydrofuran) may be used as inert solvents. Suitable bases are metal hydrides. Sodium hydride is most particularly preferred. The reactions are carried out in a temperature range from −20° C. to the reflux temperature of the solvent. Reactions are preferably carried out at RT.

The new compounds of general formula I according to the invention may contain one or more chiral centres. If for example there are two chiral centres present, the compounds may occur in the form of two diastereomeric pairs of antipodes. The invention includes the individual isomers as well as the mixtures thereof. The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula I may be separated for example by HPLC on suitable chiral stationary phases (e.g. chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+) or (−)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula I is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The new compounds of general formula I and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 µl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 µl. The incubation is ended by rapid filtration through GF/B glass fibre filters treated with polyethyleneimine (0.1%) using a cell harvester. The protein-bound radioactivity is measured using a gamma counter. Non-specific binding is defined as the bound radioactivity after the presence of 1 µM human CGRP-alpha during incubation.

The concentration binding curves are analysed using computer-aided non-linear curve fitting.

The compounds mentioned hereinbefore show Ki values ≦50 µM in the test described.

B. CGRP Antagonism in SK-N-MC Cells

SK-N-MC cells (1 million cells) are washed twice with 250 µl incubation buffer (Hanks' HEPES, 1 mM 3-isobutyl-1-methylxanthine, 1% BSA, pH 7.4) and pre-incubated at 37° C. for 15 minutes. After the addition of CGRP (10 µl) as agonist in increasing concentrations ($10^{-11}$ to $10^{-6}$ M), or additionally the substance in 3 to 4 different concentrations, the mixture is incubated for another 15 minutes.

Intracellular cAMP is then extracted by the addition of 20 µl of 1M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the pA$_2$ values of antagonistically acting substances are determined graphically.

The compounds according to the invention exhibit CGRP-antagonistic properties in the in vitro test model described, in a dosage range between $10^{-12}$ and $10^{-4}$ M.

To demonstrate that the compounds of general formula I exhibit good to very good CGRP-antagonistic activities with different structural elements, the following Table gives the K$_i$ values obtained according to the test procedure described above. It should be noted that the compounds were selected for their different structural elements and not in order to emphasise specific compounds:

| Example | K$_i$ [nM] |
| --- | --- |
| (1) | 6 |
| (2) | 27 |

Indications

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, such as e.g. irritable bowel syndrome (IBS) and inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the CGRP antagonists of the present application in a preventive and acute-therapeutic capacity, this therapeutic approach being distinguished from hormone replacement by the absence of side effects.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from 1/5 of the lower limits mentioned above up to 1/1 of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Combinations

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal antiphlogistics, corticosteroids, calcium antagonists, 5-$HT_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, imipramine, venlafaxine, lidocaine or diltiazem and other 5-$HT_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. MGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. INOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. Sst2 receptor agonists may be added.

The dosage of these active substances is expediently 1/5 of the lowest usually recommended dose to 1/1 of the normally recommended dose, i.e. for example 20 to 100 mg of sumatriptan.

Formulations

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula I according to the preferred embodiments above.

It is particularly preferable if the compounds of formula I are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

EXPERIMENTAL SECTION

As a rule IR, $^1$H-NMR and/or mass spectra have been obtained for the compounds prepared. Unless stated otherwise, $R_f$ values are determined using ready-made TLC silica gel plates 60 F254 (E. Merck, Darmstadt, Item no. 1.05714) without chamber saturation.

The ratios given for the eluants relate to units by volume of the particular solvents. The units by volume given for $NH_3$ relate to a concentrated solution of $NH_3$ in water.

Unless stated otherwise, the acid, base and salt solutions used in working up the reaction solutions are aqueous systems of the specified concentrations. Silica gel made by Millipore (MATREX™, 35-70 μm) is used for chromatographic purifications.

The HPLC data provided are measured under the parameters listed below and using the columns mentioned:

Columns used:
(column temperature: 30° C.; injection volume: 5 μL; detection at 254 nm)

| | |
|---|---|
| S1 | Zorbax column (Agilent Technologies), SB (Stable Bond) C18; 3.5 μm; 4.6 × 75 mm |
| S2 | Zorbax column (Agilent Technologies), SB (Stable Bond) C18; 1.8 μm; 3.0 × 30 mm |
| S3 | Zorbax column (Agilent Technologies), SB (Stable Bond) C18; 5 μm; 4.6 × 75 mm |
| S4 | Xbridge (Waters) C18; 3.0 × 30 mm, 2.5 μm |
| S5 | Sunfire C18 (Waters); 3.5 μm; 4.6 × 75 mm |
| S6 | Symmetry C18 (Waters); 4.6 × 75 mm, 3.5 μm |

Solvents used:
solvent A: water (with 0.1% formic acid), solvent B: acetonitrile (with 0.1% formic acid), solvent C: water (with 0.1% ammonia), solvent D: acetonitrile (with 0.1% ammonia); the percentages are based on the total volume Gradients:

| gradient | time [min] | % A | % B |
|---|---|---|---|
| G1 | 0.00 | 95 | 5 |
| (1.6 mL/min) | 0.10 | 95 | 5 |
| | 1.75 | 5 | 95 |
| | 1.90 | 5 | 95 |
| | 1.95 | 95 | 5 |
| | 2.00 | 95 | 5 |
| G2 | 0.00 | 95 | 5 |
| (1.6 mL/min) | 4.50 | 10 | 90 |
| | 5.00 | 10 | 90 |
| | 5.50 | 95 | 5 |
| G3 | 0.00 | 95 | 5 |
| (1.6 mL/min) | 4.00 | 50 | 50 |
| | 4.50 | 10 | 90 |
| | 5.00 | 10 | 90 |
| | 5.50 | 95 | 5 |
| G4 | 0.00 | 95 | 5 |
| (1.6 mL/min) | 1.00 | 10 | 90 |
| | 2.50 | 50 | 50 |
| | 2.75 | 95 | 5 |
| G5 | 0.00 | 95 | 5 |
| (1.6 mL/min) | 2.00 | 10 | 90 |
| | 5.00 | 10 | 90 |
| | 5.50 | 95 | 5 |

| gradient | time [min] | % C | % D |
|---|---|---|---|
| G6 | 0.00 | 95 | 5 |
| (1.4 mL/min) | 1.80 | 10 | 90 |
| | 2.00 | 10 | 90 |
| | 2.20 | 95 | 5 |
| G7 | 0.00 | 95 | 5 |
| (1.6 mL/min) | 2.00 | 50 | 50 |
| | 2.25 | 10 | 90 |
| | 2.50 | 10 | 90 |
| | 2.75 | 95 | 5 |

Methods:

| | column | gradient |
|---|---|---|
| method A | S1 | G1 |
| method B | S2 | G1 |
| method C | S1 | G2 |
| method D | S1 | G3 |
| method E | S2 | G4 |
| method F | S1 | G5 |

| | column | gradient |
|---|---|---|
| method G | S4 | G6 |
| method H | S2 | G7 |
| method I | S5 | G3 |
| method K | S5 | G2 |
| method L | S6 | G3 |
| method M | S6 | G8 |

In preparative HPLC purifications as a rule the same gradients are used as were used to obtain the analytical HPLC data. The products are collected under mass control, the fractions containing product are combined and freeze-dried.

In the absence of any more information regarding the configuration, it is unclear whether there are pure enantiomers involved or whether partial or even total racemisation has taken place.

The following abbreviations are used in the test descriptions:
AcOH acetic acid
BINAP 2,2'-bis(diphenylphosphino-)1,1'-binaphthyl
BOC tert-butyloxycarbonyl
CDI 1,1'-carbonyldiimidazole
cyc cyclohexane
DCM dichloromethane
DIPE diisopropylether
DIPEA diisopropylethylamine
DMF N,N-dimethylformamide
of th. of theory
d-water demineralised water
EI electron impact ionisation (in MS)
ESI electron spray ionisation (in MS)
EtOAc ethyl acetate
EtOH ethanol
el. eluant
HCl hydrochloric acid
HCOOH formic acid
HPLC High Performance Liquid Chromatography
HPLC-MS HPLC coupled mass spectrometry
HV high vacuum
i.vac. under vacuum (in vacuo)
conc. concentrated
MeOH methanol
MS mass spectrometry
MW molecular weight [g/mol]
NaOH sodium hydroxide
NH$_4$OH ammonium hydroxide (aqueous ammonia solution, 30%)
NMP N-methyl-2-pyrrolidine
Pd$_2$dba$_3$ bis(dibenzylideneacetone) palladium-(0)
PE petroleum ether
R$_f$ retention index (in TLC)
RT ambient temperature
R$_t$ retention time (in HPLC)
TEA triethylamine
TFA trifluoroacetic acid
THF tetrahydrofuran
DC drying cupboard
CAD circulating air dryer
Preparation of the Starting Compounds Intermediate 1

6-chloropyrimidine-4-carboxylic acid chloride

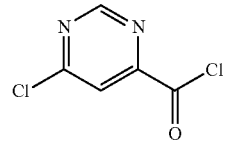

Step 1: 6-hydroxypyrimidine-4-carboxylic acid

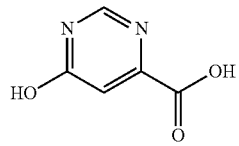

63.5 g (287 mmol) sodium diethyl-oxalacetate and 30.2 g (287 mmol) formamidine acetate were added to 24.1 g (0.597 mol) NaOH in 3.6 L water. The mixture was stirred overnight at RT. Then activated charcoal was added and the mixture was refluxed for 1 h. It was filtered while hot and after cooling acidified with aqueous HCl. The solution was concentrated to dryness by rotary evaporation. The residue contained the desired product and was used in the next step without any further purification.

Yield: 83.0 g

Step 2: 6-chloropyrimidine-4-carboxylic acid chloride

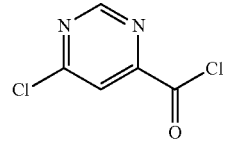

50 g (0.352 mol) 6-hydroxypyrimidine-4-carboxylic acid was taken and 500 mL phosphorus oxychloride was added thereto. Then phosphorus pentachloride was added batchwise with stirring 150 g (0.720 mol). The reaction mixture was refluxed for 5 h. The phosphorus oxychloride was distilled off and the residue was purified by vacuum distillation through a column.

Yield: 52 (83% of theoretical)
EI-MS: m/z=176/178/180 (M)$^+$ (2 Cl)

Intermediate 2

4-methyl-3H-benzoxazol-2-one

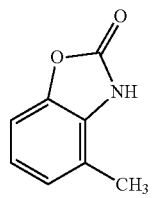

25.0 g (200 mmol) 2-amino-m-cresol and 70.4 ml. (400 mmol) DIPEA were placed in 1.0 L DCM and cooled to 0° C.

A solution of 38.0 g (227 mmol) 1.1'-carbonyldiimidazole was added dropwise thereto over 30 min. The mixture was stirred for 30 min at 0° C., then overnight at RT. After evaporation of the reaction mixture i.vac. down to half its volume the aqueous phase was washed with water (2×250 mL), 1M aqueous potassium hydrogen sulphate solution (1×250 mL) and again water (1×250 mL). The organic phase was evaporated down i.vac. The crude product remaining as a solid was triturated with a mixture of diethyl ether and PE, the precipitated solid was suction filtered, washed with PE and dried i. vac.

Yield: 25.0 g (86% of theoretical)
ESI-MS: m/z=150(M+H)$^+$
R$_t$ (HPLC)=2.67 min (Method C)

Intermediate 3

6-(6-chloropyrimidine-4-carbonyl)-4-methyl-3H-benzoxazol-2-one

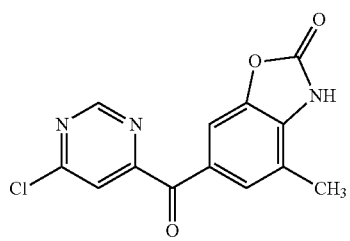 [SMILES: Cc1cc(C(=O)c2cc(Cl)ncn2)cc2oc(=O)[nH]c12]

2.34 g (13.2 mmol) 6-chloropyrimidine-4-carbonyl chloride, 8.00 g (60.0 mmol) aluminium trichloride and 1.79 g (12.0 mmol) 4-methyl-3H-benzoxazol-2-one were heated to 130° C. for 1.5 h. After cooling to RT the mixture was mixed with ice water, then extracted with ethyl acetate, the organic phase was dried on sodium sulphate and evaporated down i.vac. The crude product left as a solid was triturated with diethyl ether, suction filtered and dried in the air.

Yield: 2.00 g (52% of theoretical)
ESI-MS: m/z=290/292 (M+FI)$^+$ (Cl)
R$_t$ (HPLC)=3.17 min (Method C)

Intermediate 4

6-(6-Chlorpyrimidin-4-carbonyl)-3,4-dimethyl-3H-benzoxazol-2-one

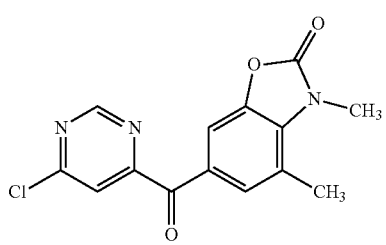 [SMILES: Cc1cc(C(=O)c2cc(Cl)ncn2)cc2oc(=O)n(C)c12]

0.35 g (8.0 mmol) sodium hydride (55%, suspension in mineral oil) were added to 2.2 g (7.6 mmol) 6-(6-chloropyrimidin-4-carbonyl)-4-methyl-3H-benzoxazol-2-one in 10 mL DMF. The reaction mixture was stirred for 30 min at RT. Then 0.95 mL (15.0 mmol) iodomethane were added and the mixture was stirred for 1 h at RT. The reaction mixture was combined with ice water and the aqueous phase was extracted several times with EtOAc. The combined organic phases were dried on sodium sulphate, filtered and evaporated to dryness by rotary evaporation. The residue was triturated with diethyl ether, suction filtered and dried.

Yield: 1.6 g (69% of theoretical)
ESI-MS: m/z=304/306 (M+H)$^+$
R$_t$ (HPLC): 3.55 min (method C)

Intermediate 5

1'H-spiro[piperidin-4,4'-quinazolin]-2'(3'H)-one

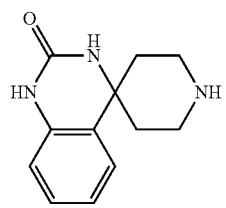 [SMILES: O=C1Nc2ccccc2C2(CCNCC2)N1]

This compound and its precursors were synthesised as described in WO2003/104236.

ESI-MS: m/z=218 (M+H)$^+$
R$_f$: 0.08 (silica gel, DCM/cyc/MeOH/NH$_4$OH=70/15/15/2)

Intermediate 6 spiro[benzo[d][1,3]oxazin-4,4'-piperidin]-2(1H)-one hydrochloride

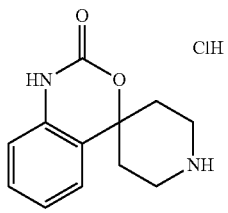 [SMILES: O=C1Nc2ccccc2C2(CCNCC2)O1 ; Cl]

This compound and its precursors were synthesised as described in U.S. Pat. No. 6,436,962.

ESI-MS: m/z=219 (M+H)$^+$
R$_f$: 0.14 (silica gel, DCM/cyc/MeOH/NH$_4$OH=70/15/15/2)

Intermediate 7 spiro[piperidin-4,4'-pyrido[2,3-d][1,3]oxazin]-2'(1'H)-one hydrochloride

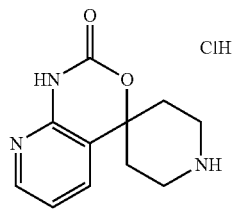 [SMILES: O=C1Nc2ncccc2C2(CCNCC2)O1 ; Cl]

Step 1: tert-butyl (6-chloro-pyridin-2-yl)-carbamate

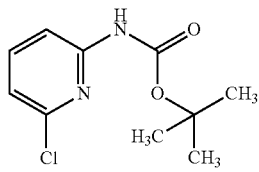

Under a nitrogen atmosphere a solution of 32.7 g (0.150 mol) BOC-anhydride in 100 mL THF was added dropwise at RT to a mixture of 17.4 g (0.135 mol) 6-chloropyridin-2-ylamine and 300 mL (0.300 mol) of a sodium hexamethyldisilazide solution (1M in THF) in 200 mL of THF. The reaction mixture was stirred overnight at RT and evaporated down i.vac. The residue was stirred between EtOAc and 1N aqueous hydrochloric acid solution. The organic phase was separated off and the aqueous phase was extracted with EtOAc. The combined organic phases were washed with saturated sodium hydrogen carbonate solution, dried and evaporated down. The residue was recrystallised from EtOH, the solid was suction filtered and dried.

Yield: 29.2 g (95% of theoretical)
ESI-MS: m/z=228 (M+)
R$_t$(HPLC): 1.70 min (method B)

Step 2: benzyl-7'-chloro-2'-oxo-1',2'-dihydrospiro[piperidin-4,4'-pyrido[2,3d][1,3]oxazin]-1-carboxylate

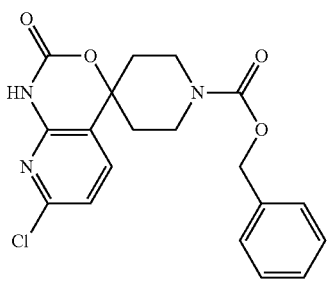 [SMILES: O=C1Nc2nc(Cl)ccc2C2(CCN(C(=O)OCc3ccccc3)CC2)O1]

Under a nitrogen atmosphere 26.0 mL (173 mmol) N,N,N,N-tetramethylene-ethylenediamine in 180 mL THF were cooled to −20° C. and combined with 70.0 mL (175 mmol) 2.5 M butyllithium solution. After 30 minutes' stirring the reaction mixture was cooled to −78° C., and at this temperature 17.8 g (78.0 mmol) tert-butyl (6-chloro-pyridin-2-yl)-carbamate in 120 mL THF were slowly added dropwise. The reaction mixture was stirred for 2.5 h at −78° C. and then combined with 27.2 g (117 mmol) Cbz-protected piperidone in 60 mL of THF. After one hour at −78° C. the mixture was heated to RT and then stirred for 18 h at 40° C. The reaction mixture was decomposed by the dropwise addition of 150 mL saturated sodium hydrogen carbonate solution. Then it was extracted with DCM. The combined organic phases were washed with water, dried and evaporated down. The residue was triturated with PE/EtOAc (1/1), the precipitate formed was suction filtered, washed with PE/EtOAc (1/1) and dried.

Yield: 16.4 g (54% of theoretical)
ESI-MS: m/z=388 (M+H)$^+$
R$_t$(HPLC): 1.57 min (method B)

Step 3: Spiro[piperidin-4,4'-pyrido[2,3-d][1,3]oxazin]-2'(1'H)-one hydrochloride

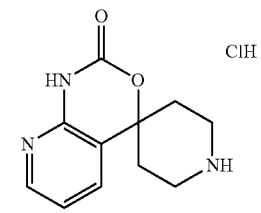 [SMILES: O=C1Nc2ncccc2C2(CCNCC2)O1 ; Cl]

16.4 g (42.0 mmol) benzyl-7'-chloro-2'-oxo-1',2'-dihydrospiro[piperidin-4,4'-pyrido[2,3d][1,3]oxazin]-1-carboxylate and 2.00 g palladium on charcoal (Pd/C 10%) in 500 mL EtOH were hydrogenated for 6 h at RT in a hydrogen atmosphere. Then 1.0 g palladium on charcoal (Pd/C 10%) were added and the reaction mixture was hydrogenated for a further 3 h at RT in a hydrogen atmosphere. After filtration of the reaction mixture the solvent was eliminated i.vac. The residue was triturated with EtOH, the precipitate formed was suction filtered, washed with EtOH and dried.

Yield: 5.40 g (50% of theoretical)
ESI-MS: m/z=220 (M+H)$^+$
R$_t$(HPLC): 0.90 min (method C)

Intermediate 8

6-(6-chloro-2-methyl-pyrimidin-4-carbonyl)-4-methyl-3H-benzoxazol-2-one

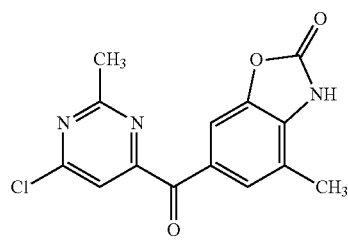 [SMILES: Cc1nc(Cl)cc(C(=O)c2cc(C)c3[nH]c(=O)oc3c2)n1]

Step 1: 6-chloro-2-methyl-pyrimidine-4-carboxylic acid chloride

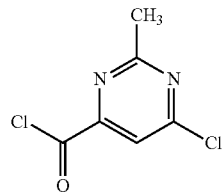

2.00 g (13.0 mmol) 6-hydroxy-2-methylpyrimidin-4-carboxylic acid were refluxed for 2 h with 11.9 mL (130 mmol) phosphorus oxychloride. After cooling to RT, 2.70 g (13.0 mmol) phosphorus-(V)-chloride were added and the mixture was boiled for 2 h. The reaction mixture was cooled to RT cooled, evaporated to dryness i.vac. And co-evaporated twice with toluene. The residue was triturated several times with DCM and the excess DCM was decanted off. The combined DCM phases were evaporated down and the residue was further reacted as the crude product.

Yield: 2.48 g (quantitative)

Step 2: 6-(6-chloro-2-methyl-pyrimidin-4-carbonyl)-4-methyl-3H-benzoxazol-2-one

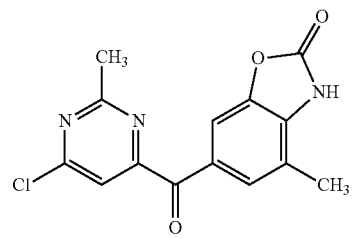 [SMILES: Cc1nc(Cl)cc(C(=O)c2cc(C)c3[nH]c(=O)oc3c2)n1]

2.48 g (13.0 mmol) 6-chloro-2-methyl-pyrimidine-4-carboxylic acid chloride, 1.94 g (13.0 mmol) 4-methyl-3H-benzoxazol-2-one and 6.93 g (52.0 mmol) aluminium trichloride were heated to 125° C. with stirring for 1.5 h. The mixture was combined with ice water and the precipitate formed was suction filtered and washed with water. Then the precipitate was dissolved in MeOH/DCM and suction filtered through silica gel. The filtrate was evaporated down and the residue was purified by flash chromatography. The fractions containing the product were combined, evaporated down and triturated with diethyl ether. The precipitate was suction filtered, washed with diethyl ether and dried i. vac.

Yield: 0.600 g (15% of theoretical)
ESI-MS: m/z=304 (M+H)$^+$
R$_t$(HPLC): 1.42 min (method B)

Intermediate 9

6-(6-chloro-2-methyl-pyrimidin-4-carbonyl)-3,4-dimethyl-3H-benzoxazol-2-one

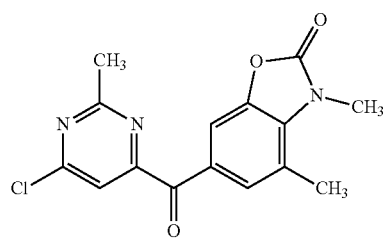 [SMILES: Cc1nc(Cl)cc(C(=O)c2cc(C)c3c(c2)oc(=O)n3C)n1]

59 mg (1.4 mmol) sodium hydride (55%, suspension in mineral oil) were added at RT to 0.37 g (1.2 mmol) 6-(6-chloro-2-methyl-pyrimidin-4-carbonyl)-4-methyl-3H-benzoxazol-2-one in 5.0 mL. DMF. The reaction mixture was stirred for 30 min at RT. Then 0.10 ml. (1.60 mmol) iodomethane were added and the mixture was stirred for 1 h at RT. Then another 0.10 ml. (1.60 mmol) iodomethane were added and the mixture was stirred overnight at RT. The reaction mixture was diluted with ice water and the precipitate formed was suction filtered. The residue was washed with water and dried i. vac.

Yield: 0.37 g (96% of theoretical)
ESI-MS: m/z=318 (M+H)$^+$
R$_t$(HPLC): 1.53 min (method B)

Intermediate 10

(6-chloro-pyrimidin-4-yl)-(7-methyl-2,3-dihydro-benzofuran-5-yl)-methanone

Step 1: 7-methyl-2,3-dihydro-benzofuran-3-ol

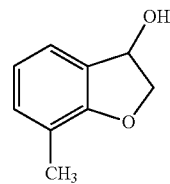

Under a nitrogen atmosphere 0.945 g (7.35 mmol) trimethylsulphoxonium chloride were placed in 20 mL THF and combined batchwise with 0.300 g (7.50 mmol) sodium hydride (55%, suspension in mineral oil). The reaction mixture was refluxed for 2 h. Then 1.00 g (7.35 mmol) 2-hydroxy-3-methylbenzaldehyde in 20 ml. THF were added dropwise to the reaction mixture and refluxed overnight. Then PE was added and the suspension obtained was filtered. The filtrate was evaporated down i.vac. and purified by flash chromatography. The fractions containing the product were combined and evaporated down.

Yield: 0.615 g (56% of theoretical)
ESI-MS: m/z=133 (M−H$_2$O+H)$^+$
R$_t$ (HPLC): 1.09 min (method B)

Step 2: 7-methyl-2,3-dihydro-benzofuran

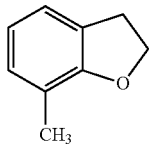

Under a nitrogen atmosphere 0.610 g (4.06 mmol) 7-methyl-2,3-dihydro-benzofuran-3-ol in 5 mL acetic acid were refluxed with 770 µL. (8.16 mmol) acetic anhydride for 2 h. After cooling to RT, 60 mg palladium on charcoal (Pd/C 10%) were added and the mixture was hydrogenated for 3.5 h under a hydrogen atmosphere (3 bar). The catalyst was filtered off and the solvent was evaporated down.

Yield: 0.350 g (64% of theoretical)
MS: m/z=134 (M$^+$)

Step 3: (6-chloro-pyrimidin-4-yl)-(7-methyl-2,3-dihydro-benzofuran-5-yl)-methanone

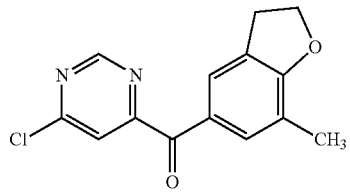 [SMILES: Cc1cc(C(=O)c2cc(Cl)ncn2)cc2c1OCC2]

0.396 g (2.24 mmol) 6-chloropyrimidin-4-carboxylic acid chloride and 0.328 g (2.46 mmol) aluminium trichloride in 10 mL DCM were stirred for 20 min at RT. Then 0.300 g (2.24 mmol) 7-methyl-2,3-dihydro-benzofuran in DCM were added dropwise to the reaction mixture and this was stirred for 1.5 h at RT. After the addition of water and DCM to the reaction mixture the phases were separated and the aqueous phase was extracted with DCM. The combined organic phases were washed with saturated aqueous sodium hydrogen carbonate solution, dried on sodium sulphate, filtered and evaporated down i.vac.

Yield: 0.550 g (62% of theoretical)
purity: 70%
ESI-MS: m/z=275/277 (Cl) (M+H)$^+$
R$_t$ (HPLC): 1.54 min (method B)

Intermediate 11

5-amino-1,3-dihydrospiro[inden-2,3'-pyrrolo[2,3-b]pyridin]-2'(1'H)-one

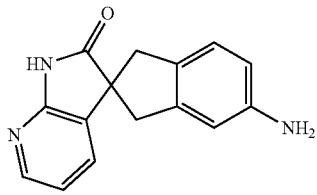 [SMILES: Nc1ccc2c(c1)CC1(C2)C(=O)Nc2ncccc21]

This compound was synthesised as described in WO2006/029153.

ESI-MS: m/z=252 (M+H)$^+$
R$_f$(DC)=0.4 (10% methanol/chloroform)

Intermediate 12

(6-chloro-pyrimidin-4-yl)-(2,3-difluoro-phenyl)-methanone

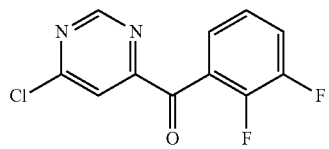 [SMILES: O=C(c1cc(Cl)ncn1)c1cccc(F)c1F]

Step 1: S-phenyl 6-chloro-pyrimidin-4-carbothionate

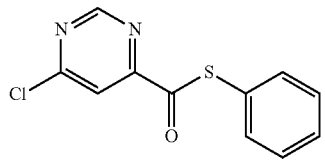 [SMILES: O=C(Sc1ccccc1)c1cc(Cl)ncn1]

1.58 mL (15.4 mmol) thiophenol and 2.75 mL (16.08 mmol) DIPEA were added at 0° C. to 3.00 g (16.1 mmol) 6-chloropyrimidine-4-carboxylic acid chloride in 100 mL DCM and stirred for 1 h at 0° C. and 1 h at RT. Then the reaction mixture was diluted with DCM and washed with saturated sodium hydrogen carbonate solution and water. The organic phase was dried on sodium sulphate, filtered, additionally filtered through silica gel and washed with DCM. The filtrate was then evaporated down.

Yield: 3.80 g (99% of theoretical)
MS: m/z=250/252 (Cl) (M$^+$)
R$_t$ (HPLC): 2.95 min (method F)

Step 2: (6-chloro-pyrimidin-4-yl)-(2,3-difluoro-phenyl)-methanone

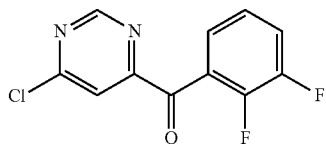 [SMILES: O=C(c1cc(Cl)ncn1)c1cccc(F)c1F]

Argon was piped through 0.50 g (2.0 mmol) S-phenyl 6-chloro-pyrimidine-4-carbothionate, 0.38 g (2.4 mmol) 2,3-difluorophenylboric acid and 0.46 g (2.4 mmol) copper-thiophene-2-carboxylate in 25 mL THF for 3 min and then 46 mg (0.05 mmol) $Pd_2dba_3$ and 35 µL (0.20 mmol) triethylphosphite were added. The reaction mixture was stirred for another 48 h at RT, then the precipitate formed was filtered off and the filtrate was evaporated down. The residue was purified by flash chromatography.

Yield: 0.47 g (83% of theoretical)
purity: 90%
ESI-MS: m/z=255/257 (Cl) (M+H)$^+$
$R_t$ (HPLC): 4.23 min (method C)

Preparation of the End Compounds

Example 1

4-methyl-6-(6-(2'-oxo-2',3'-dihydro-1'H-spiro[piperidin-4,4'-quinazolin]-1-yl)pyrimidine-4-carbonyl)benzo[d]oxazol-2(3H)-one

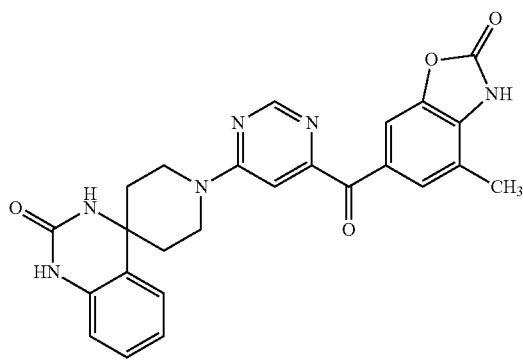 [SMILES: Cc1cc(C(=O)c2cc(N3CCC4(CC3)NC(=O)Nc3ccccc34)ncn2)cc2oc(=O)[nH]c12]

144 mg (0.500 mmol) 6-(6-chloropyrimidine-4-carbonyl)-4-methyl-3H-benzoxazol-2-one, 108 mg (0.500 mmol) 1'H-spiro[piperidin-4,4'-quinazolin]-2'(3'H)-one and 0.174 mL (1.00 mmol) DIPEA were combined in 5.0 mL DMF and stirred overnight at RT. The reaction mixture was purified by preparative HPLC, the fractions containing the product were combined and the organic solvent was eliminated i.vac. The aqueous phase was neutralised by the addition of 4N aqueous NaOH solution. The product precipitated as a solid was filtered off, washed with water and dried.

Yield: 130 mg (55% of theoretical)
ESI-MS: m/z=471 (M+H)$^+$
$R_t$ (HPLC)=2.55 min (Method C)

Example 2

4-methyl-6-(6-(2'-oxo-1,1',2',3-tetrahydrospiro[inden-2,3'-pyrrolo[2,3-b]pyridin]-5-ylamino)pyrimidine-4-carbonyl)benzo[d]oxazol-2(3H)-one

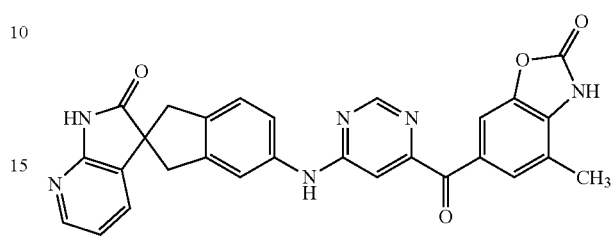

144 mg (0.500 mmol) 6-(6-chloropyrimidine-4-carbonyl)-4-methyl-3H-benzoxazol-2-one, 126 mg (0.500 mmol) 5-amino-1,3-dihydrospiro[inden-2,3'-pyrrolo[2,3-b]pyridin]-2'(1'H)-one and 16.1 mg (0.100 mmol) benzenesulphonic acid were combined in 5.0 mL 2-pentanol and refluxed for 4 h. The reaction mixture was evaporated down, the residue was triturated with PE, suction filtered and washed with PE. The residue was purified by preparative HPLC, the fractions containing the product were combined and the organic solvent was eliminated i.vac. The aqueous phase was neutralised by the addition of 1N aqueous NaOH solution. The product precipitated as a solid was filtered off, washed with water and dried.

Yield: 85 mg (34% of theoretical)
ESI-MS: m/z=505 (M+H)$^+$
$R_t$ (HPLC)=2.88 min (Method C)

Example 3

3,4-dimethyl-6-(6-(2'-oxo-2',3'-dihydro-1'H-spiro[piperidin-4,4'-quinazolin]-1-yl)pyrimidin-4-carbonyl)benzo[d]oxazol-2(3H)-one

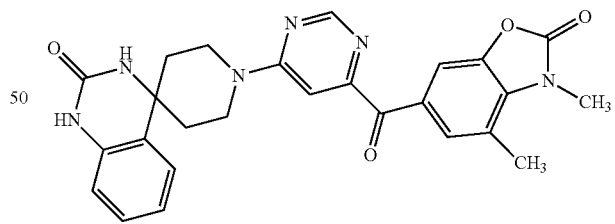

87.0 mg (0.400 mmol) 1'H-spiro[piperidin-4,4'-quinazolin]-2'(3'H)-one, 122 mg (0.400 mmol) 6-(6-chloropyrimidin-4-carbonyl)-3,4-dimethyl-3H-benzoxazol-2-one and 0.140 mL (0.800 mmol) DIPEA were combined in 3.0 mL DMF and stirred for 48 h at RT. The reaction mixture was diluted with MeOH, the precipitate was suction filtered, washed with diethyl ether and dried.

Yield: 184 mg (95% of theoretical)
ESI-MS: m/z=485 (M+H)$^+$
$R_t$ (HPLC): 1.14 min (method A)

Example 4

3,4-dimethyl-6-(6-(2'-oxo-1,1',2',3-tetrahydrospiro[inden-2,3'-pyrrolo[2,3-b]pyridin]-5-ylamino)pyrimidin-4-carbonyl)benzo[d]oxazol-2(3H)-one

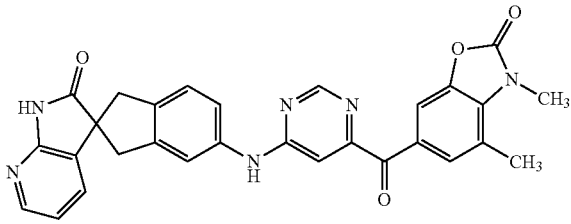 [SMILES: Cc1cc(C(=O)c2cc(Nc3ccc4c(c3)CC3(C4)C(=O)Nc4ncccc43)ncn2)cc2oc(=O)n(C)c12]

16.0 mg (0.100 mmol) benzenesulphonic acid were added to 126 mg (0.500 mmol) 5-amino-1,3-dihydrospiro[inden-2,3'-pyrrolo[2,3-b]pyridin]-2'(1'H)-one and 152 mg (0.500 mmol) 6-(6-chloro-pyrimidin-4-carbonyl)-3,4-dimethyl-3H-benzoxazol-2-one in 5.0 mL of 2-pentanol and boiled for 4 h. The reaction mixture was evaporated down and purified by preparative HPLC. The fractions containing the product were combined, the organic solvent was eliminated i.vac. and the aqueous phase remaining was neutralised with 1M aqueous NaOH solution. The product precipitated as a solid was suction filtered, washed with water and dried i. vac.

Yield: 110 mg (42% of theoretical)

ESI-MS: m/z=519 (M+H)$^+$ $R_t$ (HPLC)=1.3 min (method B)

Example 5

1'-(6-(3,4-dimethyl-2-oxo-2.3-dihydrobenzo[d]oxazol-6-carbonyl)pyrimidin-4-yl)spiro[benzo[d][1,3]oxazin-4,4'-piperidin]-2(1H)-one

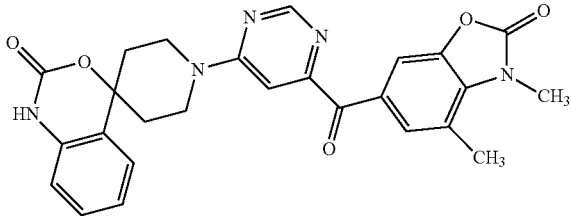 [SMILES: Cc1cc(C(=O)c2cc(N3CCC4(CC3)OC(=O)Nc3ccccc34)ncn2)cc2oc(=O)n(C)c12]

102 mg (0.400 mmol) spiro[benzo[d][1,3]oxazin-4,4'-piperidin]-2(1H)-on hydrochloride, 122 mg (0.400 mmol) 6-(6-chloropyrimidin-4-carbonyl)-4-methyl-3H-benzoxazol-2-one and 0.210 mL (1.20 mmol) DIPEA were combined in 3.0 mL DMF and stirred for 48 h. The mixture was purified by preparative HPLC-MS. The fractions containing the product were combined, the organic solvent was eliminated i.vac. and the aqueous phase remaining was neutralised with 4M aqueous NaOH solution. The product precipitated as a solid was suction filtered, washed with water and dried in the CAD.

Yield: 90 mg (46% of theoretical)

ESI-MS: m/z=486 (M+H)$^+$ $R_t$ (HPLC): 1.25 min (method B)

Example 6

1-(6-(3,4-dimethyl-2-oxo-2.3-dihydrobenzo[d]oxazol-6-carbonyl)pyrimidin-4-yl)spiro[piperidin-4,4'-pyrido[2.3-d][1,3]oxazin]-2'(1'H)-one

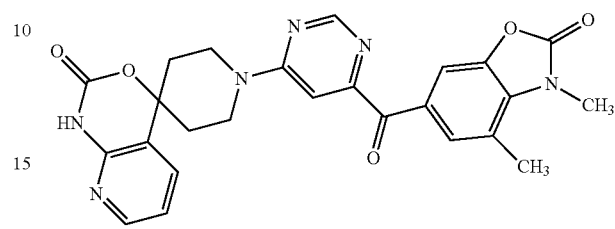

55 mg (0.21 mmol) spiro[piperidin-4,4'-pyrido[2.3-d][1,3]oxazin]-2'(1'H)-one hydrochloride, 65 mg (0.21 mmol) 6-(6-chloropyrimidin-4-carbonyl)-3,4-dimethyl-3H-benzoxazol-2-one and 0.15 mL (0.84 mmol) DIPEA were combined in 1.8 mL DMF and stirred overnight at RT. Then the reaction mixture was purified by preparative HPLC-MS. The fractions containing the product were combined and freeze-dried.

Yield: 73.0 mg (70% of theoretical)

ESI-MS: m/z=487 (M+H)$^+$ $R_t$ (HPLC): 2.60 min (method C)

Example 7

1-(6-(3,4-dimethyl-2-oxo-2.3-dihydrobenzo[d]oxazol-6-carbonyl)-2-methylpyrimidin-4-yl)spiro[piperidin-4,4'-pyrido[2,3-d][1,3]oxazin]-2'(1'H)-one

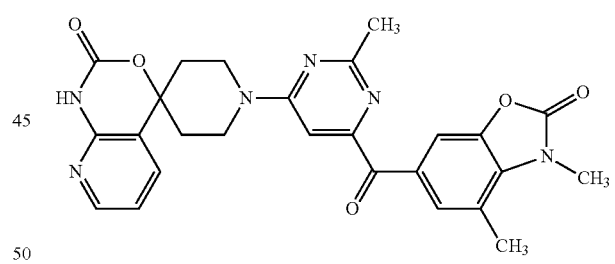

77 mg (0.30 mmol) spiro[piperidin-4,4'-pyrido[2,3-d][1,3]oxazin]-2'(1'H)-one hydrochloride, 88 mg (0.28 mmol) 6-(6-chloro-2-methyl-pyrimidin-4-carbonyl)-3,4-dimethyl-3H-benzoxazol-2-one and 0.17 mL (1.0 mmol) DIPEA were combined in 2 mL DMF and stirred overnight at RT. Then the reaction mixture was purified by preparative HPLC-MS. The fractions containing the product were combined and the organic solvent was evaporated down. The residue was neutralised with 4N aqueous sodium hydroxide solution. The precipitate formed was suction filtered, washed with water and dried i. vac.

Yield: 53 mg (35% of theoretical)

ESI-MS: m/z=501 (M+H)$^+$ $R_t$ (HPLC): 1.07 min (method B)

Example 8

5-(6-(7-methyl-2.3-dihydrobenzofuran-5-carbonyl)pyrimidin-4-ylamino)-1,3-dihydrospiro[inden-2,3'-pyrrolo[2,3-b]pyridin]-2'(1'H)-one

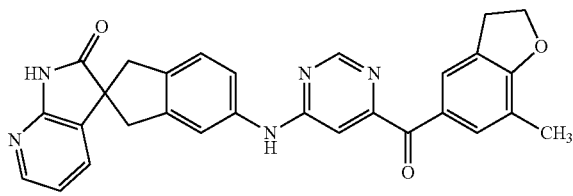 [SMILES: Cc1cc(C(=O)c2cc(Nc3ccc4c(c3)CC3(C4)C(=O)Nc4ncccc43)ncn2)cc2c1OCC2]

A spatula tip of benzenesulphonic acid was added to 70 mg (0.28 mmol) 5-amino-1,3-dihydrospiro[inden-2,3'-pyrrolo[2,3-b]pyridin]-2'(1'H)-one and 0.10 g (0.26 mmol) (6-chloro-pyrimidin-4-yl)-(7-methyl-2,3-dihydro-benzofuran-5-yl)-methanone in 2 mL 1-pentanol and the mixture was stirred at 85° C. for 1 h. The reaction mixture was evaporated down, taken up in DMF, acidified with a few drops of hydrochloric acid and purified by preparative HPLC. The fractions containing the product were combined and freeze-dried.

Yield: 60 mg (48% of theoretical)

ESI-MS: m/z=490 (M+H)$^+$ $R_t$ (HPLC): 1.39 min (method B)

Example 9

5-(6-(2,3-difluorobenzoyl)pyrimidin-4-ylamino)-1,3-dihydrospiro[inden-2,3'-pyrrolo[2,3-b]pyridin]-2'(1'H)-one

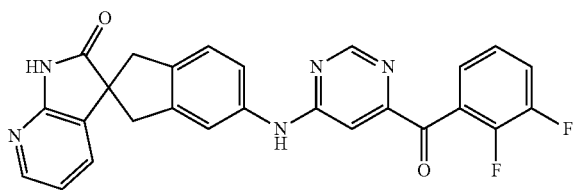 [SMILES: O=C(c1cc(Nc2ccc3c(c2)CC2(C3)C(=O)Nc3ncccc32)ncn1)c1cccc(F)c1F]

70 mg (0.28 mmol) 5-amino-1,3-dihydrospiro[inden-2,3'-pyrrolo[2,3-b]pyridin]-2'(1'H)-one, 80 mg (0.28 mmol) (6-chloro-pyrimidin-4-yl)-(2.3-difluoro-phenyl)-methanone and 60 μL DIPEA in 600 μL dimethylsulphoxide were stirred for 1 h at 80° C. After cooling the reaction mixture was combined with approx. 10 mL ice water. The liquid was decanted off and the residue was dissolved in DCM and MeOH. After drying with sodium sulphate the mixture was filtered and the solvent was evaporated down. The residue was triturated with ether, suction filtered and dried.

Yield: 82 mg (60% of theoretical)

ESI-MS: m/z=470 (M+H)$^+$ $R_t$ (HPLC): 3.97 min (method C)

The following Examples describe the preparation of pharmaceutical formulations that contain as active substance any desired compound of general formula I:

Example I

Capsules for Powder Inhalation Containing 1 mg of Active Ingredient

Composition:

1 capsule for powder inhalation contains:

| active ingredient | 1.0 mg |
|---|---|
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

Example II

Inhalable Solution for Respimat® Containing 1 mg of Active Ingredient

Composition:

1 puff contains:

| active ingredient | 1.0 mg |
|---|---|
| benzalkonium chloride | 0.002 mg |
| disodium edetate | 0.0075 mg |
| purified water ad | 15.0 μl |

Method of Preparation:

The active ingredient and benzalkonium chloride are dissolved in water and transferred into Respimat® cartridges.

Example III

Inhalable Solution for Nebulisers Containing 1 mg of Active Ingredient

Composition:

1 vial contains:

| active ingredient | 0.1 g |
|---|---|
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

Example IV

Propellant Gas-Operated Metered Dose Aerosol Containing 1 mg of Active Ingredient Composition:

1 puff contains:

| active ingredient | 1.0 mg |
|---|---|
| lecithin | 0.1% |
| propellant gas ad | 50.0 μl |

Method of Preparation:

The micronised active ingredient is homogeneously suspended in the mixture of lecithin and propellant gas. The suspension is transferred into a pressurised container with a metering valve.

Example V

Nasal Spray Containing 1 mg of Active Ingredient
Composition:

| active ingredient | 1.0 mg |
| --- | --- |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

Example VI

Injectable Solution Containing 5 mg of Active Substance Per 5 ml
Composition:

| active substance | 5 mg |
| --- | --- |
| glucose | 250 mg |
| human serum albumin | 10 mg |
| glycofurol | 250 mg |
| water for injections ad | 5 ml |

Preparation:

Glycofurol and glucose are dissolved in water for injections (WfI); human serum albumin is added; active ingredient is dissolved with heating; made up to specified volume with WfI; transferred into ampoules under nitrogen gas.

Example VII

Injectable Solution Containing 100 mg of Active Substance Per 20 ml
Composition:

| active substance | 100 mg |
| --- | --- |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

Example VIII

Lyophilisate Containing 10 mg of Active Substance
Composition:

| Active substance | 10 mg |
| --- | --- |
| Mannitol | 300 mg |
| human serum albumin | 20 mg |
| water for injections ad | 2 ml |

Preparation:

Mannitol is dissolved in water for injections (WfI); human serum albumin is added; active ingredient is dissolved with heating; made up to specified volume with WfI; transferred into vials; freeze-dried.

Solvent for Lyophilisate:

| Polysorbate 80 = Tween 80 | 20 mg |
| --- | --- |
| mannitol | 200 mg |
| water for injections ad | 10 ml |

Preparation:

Polysorbate 80 and mannitol are dissolved in water for injections (WfI); transferred into ampoules.

Example IX

Tablets Containing 20 mg of Active Substance
Composition:

| active substance | 20 mg |
| --- | --- |
| lactose | 120 mg |
| corn starch | 40 mg |
| magnesium stearate | 2 mg |
| Povidone K 25 | 18 mg |

Preparation:

Active substance, lactose and corn starch are homogeneously mixed; granulated with an aqueous solution of Povidone; mixed with magnesium stearate; compressed in a tablet press; weight of tablet 200 mg.

Example X

Capsules Containing 20 mg Active Substance
Composition:

| active substance | 20 mg |
| --- | --- |
| corn starch | 80 mg |
| highly dispersed silica | 5 mg |
| magnesium stearate | 2.5 mg |

Preparation:

Active substance, corn starch and silica are homogeneously mixed; mixed with magnesium stearate; the mixture is packed into size for 3 hard gelatine capsules in a capsule filling machine.

Example XI

Suppositories Containing 50 mg of Active Substance
Composition:

| active substance | 50 mg |
|---|---|
| hard fat (Adeps solidus) q.s. Ad | 1700 mg |

Preparation:

Hard fat is melted at about 38° C.; ground active substance is homogeneously dispersed in the molten hard fat; after cooling to about 35° C. it is poured into chilled moulds.

Example XII

Injectable Solution Containing 10 mg of Active Substance Per 1 ml
Composition:

| active substance | 10 mg |
|---|---|
| mannitol | 50 mg |
| human serum albumin | 10 mg |
| water for injections ad | 1 ml |

Preparation:

Mannitol is dissolved in water for injections (WfI); human serum albumin is added; active ingredient is dissolved with heating; made up to specified volume with WfI; transferred into ampoules under nitrogen gas.

The invention claimed is:

1. A compound of the general formula I

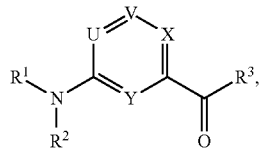
(I)

wherein
R$^1$ denotes a group of general formula IIa or IIb

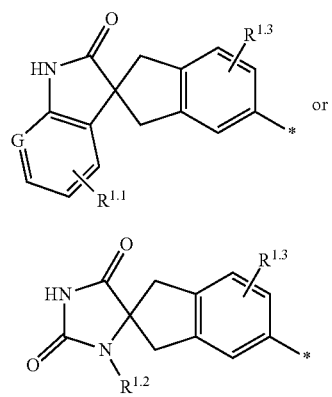
(IIa)

(IIb)

and
R$^2$ denotes H or C$_{1-3}$-alkyl, or
R$^1$ and R$^2$ together with the nitrogen atom to which they are bound denote a group of the formulae IIIa or IIIb

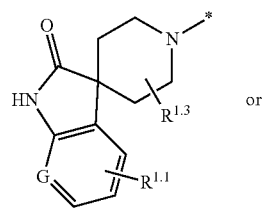
(IIIa)

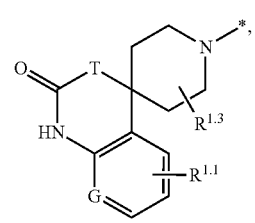
(IIIb)

G denotes C—R$^{1.1}$ or N,
T denotes N—R$^{1.2}$ or O,
R$^{1.1}$ independently of one another denote
(a) H,
(b) halogen, C$_{1-3}$-alkyl, —OH, —CN, —O—C$_{1-3}$-alkyl, —C(O)—O—C$_{1-3}$-alkyl, C$_{2-4}$-alkenyl, —C$_{2-4}$-alkynyl, C$_{1-3}$-alkyl-S, cyclopropyl, —NH$_2$, —COOH, —NH—C(O)—O—C$_{1-3}$-alkyl, —NH—C(O)—C$_{1-3}$-alkyl,
(c) a C$_{1-3}$-alkyl group or C$_{1-3}$-alkyl-O— group wherein each methylene group is substituted by up to two fluorine atoms and each methyl group is substituted by up to three fluorine atoms,
R$^{1.2}$ independently of one another denote
H or
C$_{1-3}$-alkyl,
R$^{1.3}$ denotes
(a) H,
F, —CN, C$_{1-3}$-alkyl, —CO$_2$—R$^{1.3.1}$ or
a C$_{1-3}$-alkyl group wherein each methylene group may be substituted by up to two fluorine atoms and each methyl group may be substituted by up to three fluorine atoms,
R$^{1.3.1}$ denotes
(a) H,
(b) C$_{1-6}$-alkyl,
R$^3$ a 6 or 10-membered aryl group substituted by the groups R$^{3.1}$, R$^{3.2}$ and R$^{3.3}$ or a 6-membered heteroaryl group substituted by the groups R$^{3.1}$, R$^{3.2}$ and R$^{3.3}$ which is attached via a carbon atom,
R$^{3.1}$ denotes
(a) H,
(b) halogen, —NH$_2$, C$_{1-4}$-alkyl-NH, (C$_{1-4}$-alkyl)$_2$N, C$_{1-3}$-alkyl-C(O)—NH, C$_{1-3}$-alkyl-S(O$_2$)—NH, —CN, —OH, —O—C(O)—NH—C$_{1-3}$-alkyl,
(c) C$_{1-4}$-alkyl, R$^{3.1.1}$—C$_{1-3}$-alkylene, C$_{2-4}$-alkenyl, C$_{2-4}$-alkynyl, C$_{1-3}$-alkyl-O, C$_{1-3}$-alkyl-S(O)$_m$, cyclopropyl,
(d) a C$_{1-3}$-alkyl or C$_{1-3}$-alkyl-O— group wherein each methylene group is substituted by up to two fluorine atoms and each methyl group is substituted by up to three fluorine atoms,
(e) —C(O)—R$^{3.1.2}$,
(f) —S(O)$_2$—R$^{3.1.3}$, $R^{3.1.1}$ denotes
  (a) H,
    $C_{3-6}$-cycloalkyl, $C_{5-6}$-cycloalkenyl,
    $(R^{3.1.1.1})_2N$,
    a saturated, mono- or diunsaturated 5- or 6-membered heterocyclic group which is substituted at a nitrogen atom by a group $R^{3.1.1.1}$ and is substituted at a carbon atom by one or two groups $R^{3.1.1.2}$, or
    a heteroaryl group which is substituted at a carbon atom by a group $R^{3.1.1.2}$,
$R^{3.1.1.1}$ independently of one another denote
  (a) H, $C_{1-4}$-alkyl, $C_{3-6}$-cycloalkyl,
  (b) heterocyclyl,
  (c) aryl-$C_{0-3}$-alkylene or heteroaryl-$C_{0-3}$-alkylene,
$R^{3.1.1.2}$ independently of one another denote
  (a) H, F, $C_{1-3}$-alkyl, —CN, —OH, —O—$C_{1-3}$-alkyl, —CO(O)$R^{3.1.1.2.1}$, $H_2N$, $(C_{1-4}$-alkyl)-NH, $(C_{1-4}$-alkyl)$_2$N,
  (b) phenyl or phenyl-$CH_2$,
  (c) a $C_{1-3}$-alkyl or —O—$C_{1-3}$-alkyl group wherein each methylene group is substituted by up to two fluorine atoms and each methyl group is substituted by up to three fluorine atoms, or
$R^{3.1.1.2.1}$ denotes H, $C_{1-6}$-alkyl, benzyl,
$R^{3.1.2}$ denotes —O—$C_{1-3}$-alkyl, —OH, —NR$^{3.1.2.1}$R$^{3.1.2.2}$,
$R^{3.1.2.1}$ denotes H, $C_{1-3}$-alkyl,
$R^{3.1.2.2}$ denotes H, $C_{1-3}$-alkyl,
$R^{3.1.2.1}$ and $R^{3.1.2.2}$ together may also form a ring which is selected from among azetidinyl, pyrrolidinyl, piperidinyl, piperazinyl and morpholinyl,
$R^{3.1.3}$ denotes —O—$C_{1-3}$-alkyl, —NR$^{3.1.3.1}$R$^{3.1.3.2}$,
$R^{3.1.3.1}$ denotes H, $C_{1-3}$-alkyl,
$R^{3.1.3.2}$ denotes H, $C_{1-3}$-alkyl,
$R^{3.1.3.1}$ and $R^{3.1.3.2}$ together may also form a ring which is selected from among azetidinyl, pyrrolidinyl, piperidinyl, piperazinyl and morpholinyl,
$R^{3.2}$ denotes
  (a) H,
  (b) halogen, —NH$_2$, $C_{1-4}$-alkyl-NH, $(C_{1-4}$-alkyl)$_2$N, $C_{1-3}$-alkyl-C(O)—NH, $C_{1-3}$-alkyl-S(O$_2$)—NH, —CN, —OH, —O—C(O)—NH—$C_{1-3}$-alkyl,
  (c) $C_{1-4}$-alkyl, $C_{2-4}$-alkenyl, $C_{2-4}$-alkynyl, $C_{1-3}$-alkyl-O, $C_{1-3}$-alkyl-S(O)$_m$, cyclopropyl,
  (d) a $C_{1-3}$-alkyl or $C_{1-3}$-alkyl-O— group wherein each methylene group is substituted by up to two fluorine atoms and each methyl group is substituted by up to three fluorine atoms,
  (e) —C(O)—$R^{3.2.1}$,
  (f) —S(O)$_2$—$R^{3.2.2}$,
$R^{3.2.1}$ denotes —O—$C_{1-3}$-alkyl, —OH, —NR$^{3.2.1.1}$R$^{3.2.1.2}$,
$R^{3.2.1.1}$ denotes H, $C_{1-3}$-alkyl,
$R^{3.2.1.2}$ denotes H, $C_{1-3}$-alkyl,
$R^{3.2.1.1}$ and $R^{3.2.1.2}$ together may also form a ring which is selected from among azetidinyl, pyrrolidinyl, piperidinyl, piperazinyl and morpholinyl,
$R^{3.2.2}$ denotes —NR$^{3.2.2.1}$R$^{3.2.2.2}$,
$R^{3.2.2.1}$ denotes H, $C_{1-3}$-alkyl,
$R^{3.2.2.2}$ denotes H, $C_{1-3}$-alkyl,
$R^{3.2.2.1}$ and $R^{3.2.2.2}$ together may also form a ring which is selected from among azetidinyl, pyrrolidinyl, piperidinyl, piperazinyl and morpholinyl, $R^{3.3}$ denotes
  (a) H,
  (b) halogen, —NH$_2$, $C_{1-4}$-alkyl-NH, $(C_{1-4}$-alkyl)$_2$N, $C_{1-3}$-alkyl-C(O)—NH, $C_{1-3}$-alkyl-S(O$_2$)—NH, —CN, —OH, —O—C(O)—NH—$C_{1-3}$-alkyl,
  (c) $C_{1-4}$-alkyl, $C_{2-4}$-alkenyl, $C_{2-4}$-alkynyl, $C_{1-3}$-alkyl-O, $C_{1-3}$-alkyl-S(O)$_m$, cyclopropyl,
  (d) a $C_{1-3}$-alkyl or $C_{1-3}$-alkyl-O— group wherein each methylene group is substituted by up to two fluorine atoms and each methyl group is substituted by up to three fluorine atoms,
  (e) —C(O)—$R^{3.3.1}$,
  (f) —S(O)$_2$—$R^{3.3.2}$,
$R^{3.3.1}$ denotes —O—$C_{1-3}$-alkyl, —OH, —NR$^{3.3.1.1}$R$^{3.3.1.2}$,
$R^{3.3.1.1}$ denotes H, $C_{1-3}$-alkyl,
$R^{3.3.1.2}$ denotes H, $C_{1-3}$-alkyl,
$R^{3.3.1.1}$ and $R^{3.3.1.2}$ together may also form a ring which is selected from among azetidinyl, pyrrolidinyl, piperidinyl, piperazinyl and morpholinyl,
$R^{3.3.2}$ denotes —O—$C_{1-3}$-alkyl, —NR$^{3.3.2.1}$R$^{3.3.2.2}$,
$R^{3.3.2.1}$ denotes H, $C_{1-3}$-alkyl,
$R^{3.3.2.2}$ denotes H, $C_{1-3}$-alkyl,
$R^{3.3.2.1}$ and $R^{3.3.2.2}$ together may also form a ring which is selected from among azetidinyl, pyrrolidinyl, piperidinyl, piperazinyl and morpholinyl, or
$R^{3.2}$ and $R^{3.3}$ together with the carbon atoms to which they are attached form a monounsaturated 5-membered or a mono- or diunsaturated 6-membered heterocyclic group or a 5- to 6-membered heteroaryl group, wherein
  the heterocycles mentioned previously may contain a carbonyl, thiocarbonyl or cyanoimino group adjacent to a nitrogen atom, and
  may optionally be additionally substituted at one or two nitrogen atoms by a group $R^{3.3.3}$ in each case and
  may optionally be additionally substituted at one or two carbon atoms by one or two groups $R^{3.3.4}$ in each case,
$R^{3.3.3}$ independently of one another denote
  (a) $C_{1-4}$-alkyl or
  (b) $C_{3-6}$-cycloalkyl,
$R^{3.3.4}$ independently of one another denote
  (a) $C_{1-4}$-alkyl or
  (b) $C_{3-6}$-cycloalkyl,
  (c) halogen, CN, —O—$C_{1-3}$-alkyl, —NH$_2$,
  (d) a $C_{1-3}$-alkyl or $C_{1-3}$-alkyl-O— group wherein each methylene group is substituted by up to two fluorine atoms and each methyl group is substituted by up to three fluorine atoms,
U denotes N, or C—$R^4$,
V denotes C—$R^5$,
X denotes N, or CR$^6$,
Y denotes N or C—$R^7$,
  while two of the previously mentioned groups U, X and Y simultaneously denote a nitrogen atom,
$R^4$ denotes
  (a) H,
  (b) a $C_{1-6}$-alkyl or $C_{1-3}$-alkyl-O— group which is substituted in each case by a group $R^{4.1}$,
  (c) $R^{4.2}R^{4.3}N$, $R^{4.2}R^{4.3}N$—$C_{1-3}$-alkylene,
  (d) halogen, —CN, —OH, —COOH, $C_{1-3}$-alkyl-O, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
  (e) a $C_{1-3}$-alkyl or $C_{1-3}$-alkyl-O— group wherein each methylene group is substituted by up to two fluorine atoms and each methyl group is substituted by up to three fluorine atoms,
$R^{4.1}$ denotes H, OH or —O—$CH_3$,
$R^{4.2}$ denotes H or $C_{1-3}$-alkyl, $R^{4.3}$ denotes H or $C_{1-3}$-alkyl, or $R^{4.2}$ and $R^{4.3}$ together with the nitrogen atom to which they are bound denote a 3- to 6-membered heterocyclic group, $R^5$ denotes (a) H, (b) a $C_{1-6}$-alkyl or $C_{1-3}$-alkyl-O— group which is substituted in each case by a group $R^{5.1}$, (c) —$NR^{5.2}R^{5.3}$, $NR^{5.2}R^{5.3}$—$C_{1-3}$-alkylene, (d) halogen, —CN, —OH, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene, (e) aryl-$C_{0-3}$-alkylene-O— group, (f) a $C_{1-3}$-alkyl or $C_{1-3}$-alkyl-O— group wherein each methylene group is substituted by up to two fluorine atoms and each methyl group is substituted by up to three fluorine atoms, $R^{5.1}$ denotes H, OH or —O—$CH_3$, $R^{5.2}$ denotes H or $C_{1-6}$-alkyl, $R^{5.3}$ denotes H, $C_{1-6}$-alkyl or —$SO_2$—$C_{1-3}$-alkyl, or $R^{5.2}$ and $R^{5.3}$ together with the nitrogen atom to which they are bound denote a 3- to 6-membered heterocyclic group, $R^6$ denotes (a) H, (b) a $C_{1-6}$-alkyl or $C_{1-3}$-alkyl-O— group which is substituted in each case by a group $R^{6.1}$, (c) $R^{6.2}R^{6.3}N$, $R^{6.2}R^{6.3}N$—$C_{1-3}$-alkylene, (d) halogen, —CN, —OH, —COOH, $C_{1-3}$-alkyl-O, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene, (e) a $C_{1-3}$-alkyl or $C_{1-3}$-alkyl-O— group wherein each methylene group is substituted by up to two fluorine atoms and each methyl group is substituted by up to three fluorine atoms, $R^{6.1}$ denotes H, OH or —O—$CH_3$, $R^{6.2}$ denotes H or $C_{1-3}$-alkyl, $R^{6.3}$ denotes H or $C_{1-3}$-alkyl, or $R^{6.2}$ and $R^{6.3}$ together with the nitrogen atom to which they are bound denote a 3- to 6-membered heterocyclic group, and $R^7$ denotes H, halogen or $C_{1-3}$-alkyl, or a tautomer or salt thereof.

2. compound of the formula I according to claim 1, wherein $R^1$ denotes a group of the formula

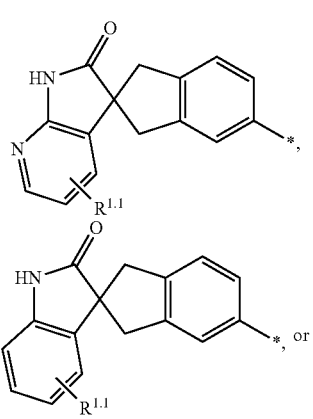

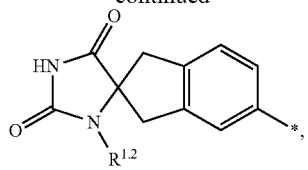

$R^{1.1}$ denotes (a) H, (b) halogen, $C_{1-3}$-alkyl, —OH, —CN, —O—$C_{1-3}$-alkyl, —C(O)—O—$C_{1-3}$-alkyl, $C_{2-4}$-alkenyl, $C_{2-4}$-alkynyl, $C_{1-3}$-alkyl-S, —$NH_2$, (c) a $C_{1-3}$-alkyl group or $C_{1-3}$-alkyl-O— group wherein each methylene group is substituted by up to two fluorine atoms and each methyl group is substituted by up to three fluorine atoms, and $R^{1.2}$ denotes (a) H or (b) $CH_3$, or a tautomer or salt thereof.

3. A compound of the formula I according to claim 1, wherein $R^1$ and $R^2$ together with the nitrogen atom to which they are bound denote a group of the formula

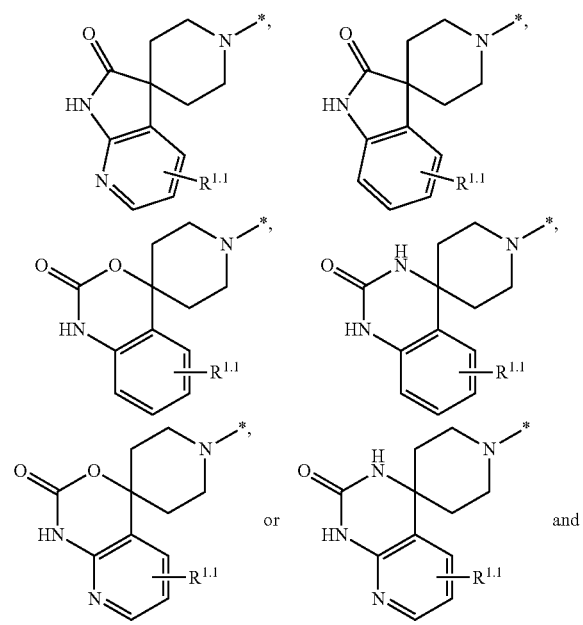

$R^{1.1}$ denotes (a) H, halogen, $C_{1-3}$-alkyl, —OH, —CN, —O—$C_{1-3}$-alkyl, —C(O)—O—$C_{1-3}$-alkyl, $C_{2-4}$-alkenyl, $C_{2-4}$-alkynyl, $C_{1-3}$-alkyl-S, —$NH_2$, a $C_{1-3}$-alkyl group or $C_{1-3}$-alkyl-O— group wherein each methylene group is substituted by up to two fluorine atoms and each methyl group is substituted by up to three fluorine atoms, or a tautomer or salt thereof.

4. A compound of the formula I according to claim 1, wherein $R^1$ denotes a group of the formula

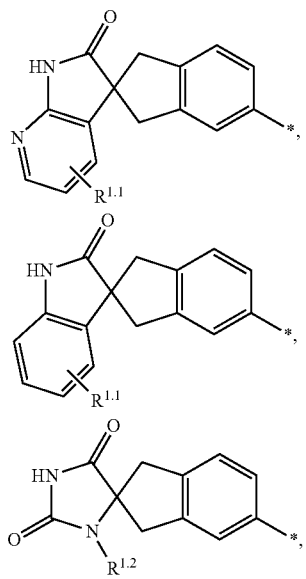

$R^{1.1}$ denotes
(a) F, CH$_3$, —OH, —O—CH$_3$ or
(b) CF$_3$, or a tautomer or salt thereof.

5. A compound of the formula I according to claim 1, wherein $R^1$ and $R^2$ together with the nitrogen atom to which they are bound denote a group of the formula

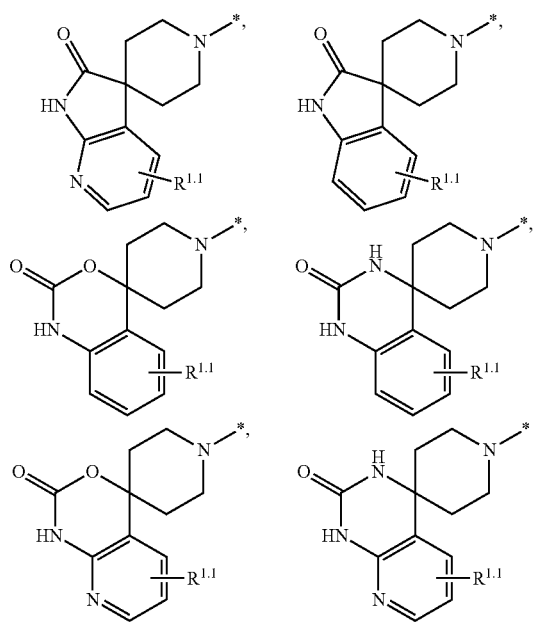

$R^{1.1}$ denotes
(a) F, CH$_3$, —OH, —O—CH$_3$ or CF$_3$, or a tautomer or salt thereof.

6. A Compound of the formula I according to claim 1, wherein $R^1$ denotes a group of the formula

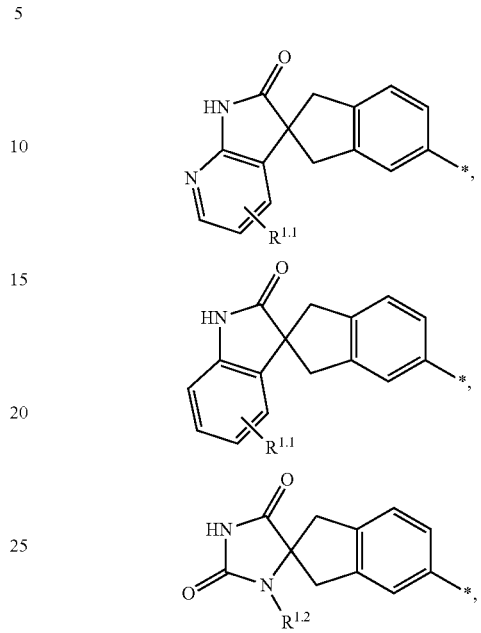

or a tautomer or salt thereof.

7. A compounds of the formula I according to claim 1, wherein $R^1$ and $R^2$ together with the nitrogen atom to which they are bound denote a group of from the formula

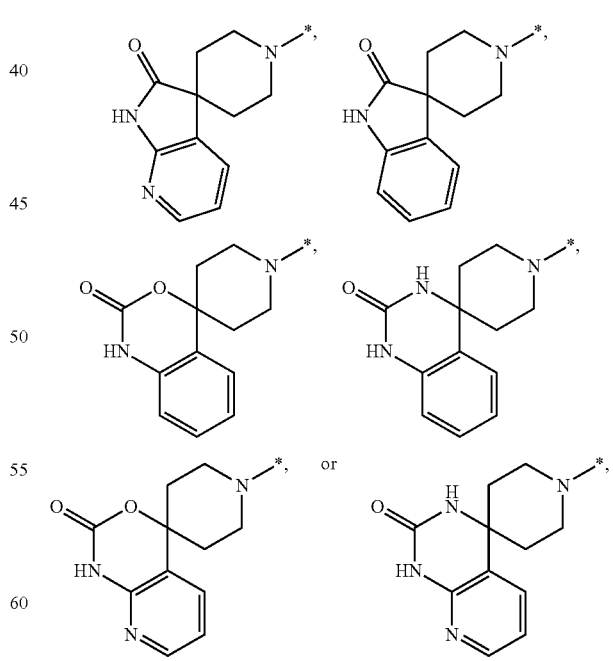

or a tautomer or salt thereof.

8. A compound of the formula I according to claim 1, wherein $R^3$ denotes a group of the formula IV

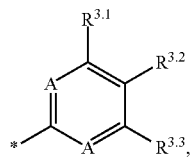
(IV)

A independently of one another denote C—H, C—F or N,
$R^{3.1}$ denotes
(a) H,
halogen, —NH$_2$, C$_{1-4}$-alkyl-NH, (C$_{1-4}$-alkyl)$_2$N, C$_{1-3}$-alkyl-C(O)—NH, C$_{1-3}$-alkyl-S(O)$_2$—NH, —CN, —OH, —O—C(O)—NH—C$_{1-3}$-alkyl,
C$_{1-4}$-alkyl, $R^{3.1.1}$—C$_{1-3}$-alkylene, C$_{2-4}$-alkenyl, C$_{2-4}$-alkynyl, C$_{1-3}$-alkyl-O, C$_{1-3}$-alkyl-S,
a C$_{1-3}$-alkyl or C$_{1-3}$-alkyl-O— group wherein each methylene group is substituted by up to two fluorine atoms and each methyl group is substituted by up to three fluorine atoms,
—C(O)—$R^{3.1.2}$,
—S(O)$_2$—$R^{3.1.3}$,
$R^{3.1.1}$ denotes
(a) H,
C$_{3-6}$-cycloalkyl, C$_{5-6}$-cycloalkenyl,
($R^{3.1.1.1}$)$_2$N,
a saturated, mono- or diunsaturated 5- or 6-membered heterocyclic group which is substituted at a nitrogen atom by a group $R^{3.1.1.1}$ and is substituted at a carbon atom by one or two groups $R^{3.1.1.2}$, or
a heteroaryl group which is substituted at a carbon atom by a group $R^{3.1.1.2}$,
$R^{3.1.1.1}$ independently of one another denote
H, C$_{1-4}$-alkyl, C$_{3-6}$-cycloalkyl,
heterocyclyl,
aryl-C$_{0-3}$-alkylene or heteroaryl-C$_{0-3}$-alkylene,
$R^{3.1.1.2}$ independently of one another denote
H, F, C$_{1-3}$-alkyl, —CN, —OH, —O—C$_{1-3}$-alkyl, —CO(O)$R^{3.1.1.2.1}$, H$_2$N, (C$_{1-4}$-alkyl)-NH, (C$_{1-4}$-alkyl)$_2$N, phenyl or phenyl-CH$_2$,
a C$_{1-3}$-alkyl or —O—C$_{1-3}$-alkyl group wherein each methylene group is substituted by up to two fluorine atoms and each methyl group is substituted by up to three fluorine atoms, or
$R^{3.1.1.2.1}$ denotes H, C$_{1-6}$-alkyl, benzyl,
$R^{3.1.2}$ denotes —O—C$_{1-3}$-alkyl, —OH, —NR$^{3.1.2.1}$R$^{3.1.2.2}$,
$R^{3.1.2.1}$ denotes H, C$_{1-3}$-alkyl,
$R^{3.1.2.2}$ denotes H, C$_{1-3}$-alkyl,
$R^{3.1.3}$ denotes —NR$^{3.1.3.1}$R$^{3.1.3.2}$,
$R^{3.1.3.1}$ denotes H, C$_{1-3}$-alkyl,
$R^{3.1.3.2}$ denotes H, C$_{1-3}$-alkyl,
$R^{3.2}$ denotes
(a) H,
halogen, —NH$_2$, C$_{1-4}$-alkyl-NH, (C$_{1-4}$-alkyl)$_2$N, C$_{1-3}$-alkyl-C(O)—NH, C$_{1-3}$-alkyl-S(O)$_2$—NH, —CN, —OH, —O—C(O)—NH—C$_{1-3}$-alkyl,
C$_{1-4}$-alkyl, C$_{2-4}$-alkenyl, C$_{2-4}$-alkynyl, C$_{1-3}$-alkyl-O, C$_{1-3}$-alkyl-S,
a C$_{1-3}$-alkyl or C$_{1-3}$-alkyl-O— group wherein each methylene group is substituted by up to two fluorine atoms and each methyl group is substituted by up to three fluorine atoms,
—C(O)—$R^{3.2.1}$,
—S(O)$_2$—$R^{3.2.2}$,
$R^{3.2.1}$ denotes —O—C$_{1-3}$-alkyl, —OH, —NR$^{3.2.1.1}$R$^{3.2.1.2}$,
$R^{3.2.1.1}$ denotes H, C$_{1-3}$-alkyl,
$R^{3.2.1.2}$ denotes H, C$_{1-3}$-alkyl,
$R^{3.2.2}$ denotes —NR$^{3.2.2.1}$R$^{3.2.2.2}$,
$R^{3.2.2.1}$ denotes H, C$_{1-3}$-alkyl,
$R^{3.2.2.2}$ denotes H, C$_{1-3}$-alkyl,
$R^{3.3}$ denotes
(a) H,
halogen, —NH$_2$, C$_{1-4}$-alkyl-NH, (C$_{1-4}$-alkyl)$_2$N, C$_{1-3}$-alkyl-C(O)—NH, C$_{1-3}$-alkyl-S(O)$_2$—NH, —CN, —OH, —O—C(O)—NH—C$_{1-3}$-alkyl,
C$_{1-4}$-alkyl, C$_{2-4}$-alkenyl, C$_{2-4}$-alkynyl, C$_{1-3}$-alkyl-O, C$_{1-3}$-alkyl-S,
a C$_{1-3}$-alkyl or C$_{1-3}$-alkyl-O— group wherein each methylene group is substituted by up to two fluorine atoms and each methyl group is substituted by up to three fluorine atoms,
—C(O)—$R^{3.3.1}$,
—S(O)$_2$—$R^{3.3.2}$,
$R^{3.3.1}$ denotes —O—C$_{1-3}$-alkyl, —OH, —NR$^{3.3.1.1}$R$^{3.3.1.2}$,
$R^{3.3.1.1}$ denotes H, C$_{1-3}$-alkyl,
$R^{3.3.1.2}$ denotes H, C$_{1-3}$-alkyl,
$R^{3.3.2}$ denotes —O—C$_{1-3}$-alkyl, —NR$^{3.3.2.1}$R$^{3.3.2.2}$,
$R^{3.3.2.1}$ denotes H, C$_{1-3}$-alkyl,
$R^{3.3.2.2}$ denotes H, C$_{1-3}$-alkyl, or
$R^{3.2}$ and $R^{3.3}$ together with the carbon atoms to which they are attached form a monounsaturated 5-membered or a mono- or diunsaturated 6-membered heterocyclic group or a 5- to 6-membered heteroaryl group, wherein
the heterocycles mentioned previously may contain a carbonyl, thiocarbonyl or cyanoimino group adjacent to a nitrogen atom, and
may optionally be additionally substituted at one or two nitrogen atoms by a group $R^{3.3.3}$ in each case and
may optionally be additionally substituted at one or two carbon atoms by one or two groups $R^{3.3.4}$ in each case,
$R^{3.3.3}$ independently of one another denote
C$_{1-4}$-alkyl or
C$_{3-6}$-cycloalkyl,
$R^{3.3.4}$ independently of one another denote
C$_{1-4}$-alkyl, C$_{3-6}$-cycloalkyl,
halogen, CN, C$_{1-3}$-alkyl-O—, —NH$_2$,
a C$_{1-3}$-alkyl or C$_{1-3}$-alkyl-O— group wherein each methylene group is substituted by up to two fluorine atoms and each methyl group is substituted by up to three fluorine atoms,
or a tautomer or salt thereof.

9. A compound of the formula I according to claim 1, wherein
$R^3$ denotes a group of the formula IV

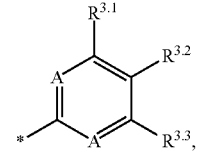
(IV)

A independently of one another denote C—H, C—F or N,
$R^{3.1}$ denotes
(a) H,
halogen, —NH$_2$, C$_{1-4}$-alkyl-NH, (C$_{1-4}$-alkyl)$_2$N, C$_{1-3}$-alkyl-C(O)—NH, —CN, —OH, —O—C(O)—NH—C$_{1-3}$-alkyl, $C_{1-4}$-alkyl, $C_{2-4}$-alkenyl, $C_{2-4}$-alkynyl, $C_{1-3}$-alkyl-O, $C_{1-3}$-alkyl-S, a $C_{1-3}$-alkyl or $C_{1-3}$-alkyl-O— group wherein each methylene group is substituted by up to two fluorine atoms and each methyl group is substituted by up to three fluorine atoms, $R^{3.2}$ denotes
(a) H,
(b) halogen, —NH$_2$, $C_{1-4}$-alkyl-NH, $(C_{1-4}$-alkyl)$_2$N, $C_{1-3}$-alkyl-C(O)—NH, —CN, —OH, —O—C(O)—NH—$C_{1-3}$-alkyl,
(c) $C_{1-4}$-alkyl, $C_{2-4}$-alkenyl, $C_{2-4}$-alkynyl, $C_{1-3}$-alkyl-O, $C_{1-3}$-alkyl-S,
(d) a $C_{1-3}$-alkyl or $C_{1-3}$-alkyl-O— group wherein each methylene group is substituted by up to two fluorine atoms and each methyl group is substituted by up to three fluorine atoms, $R^{3.3}$ denotes
H,
halogen, —NH$_2$, $C_{1-4}$-alkyl-NH, $(C_{1-4}$-alkyl)$_2$N, $C_{1-3}$-alkyl-C(O)—NH, —CN, —OH, —O—C(O)—NH—$C_{1-3}$-alkyl,
$C_{1-4}$-alkyl, $C_{2-4}$-alkenyl, $C_{2-4}$-alkynyl, $C_{1-3}$-alkyl-O, $C_{1-3}$-alkyl-S,
a $C_{1-3}$-alkyl or $C_{1-3}$-alkyl-O— group wherein each methylene group is substituted by up to two fluorine atoms and each methyl group is substituted by up to three fluorine atoms, $R^{3.2}$ and $R^{3.3}$ together with the carbon atoms to which they are attached form a monounsaturated 5-membered or a mono- or diunsaturated 6-membered heterocyclic group or a 5- to 6-membered heteroaryl group, wherein
the heterocycles mentioned previously may contain a carbonyl, thiocarbonyl or cyanoimino group adjacent to a nitrogen atom, and
may optionally be additionally substituted at one or two nitrogen atoms by a group $R^{3.3.3}$ in each case and
may optionally be additionally substituted at one or two carbon atoms by one or two groups $R^{3.3.4}$ in each case, $R^{3.3.3}$ independently of one another denote
$C_{1-4}$-alkyl or
$C_{3-6}$-cycloalkyl, $R^{3.3.4}$ independently of one another denote
$C_{1-4}$-alkyl, $C_{3-6}$-cycloalkyl,
halogen, CN, $C_{1-3}$-alkyl-O—, —NH$_2$,
a $C_{1-3}$-alkyl or $C_{1-3}$-alkyl-O— group wherein each methylene group is substituted by up to two fluorine atoms and each methyl group is substituted by up to three fluorine atoms, or a tautomers or salt thereof.

10. A compounds of the formula I according to claim 1, wherein
$R^3$ denotes a group of the formula IVa

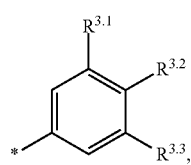

(IVa)

$R^{3.1}$ denotes
(a) H,
F, Cl, Br, —NH$_2$, $C_{1-3}$-alkyl-NH, $(C_{1-3}$-alkyl)$_2$N, $C_{1-3}$-alkyl-C(O)—NH, —CN, —OH, $C_{1-4}$-alkyl, $C_{2-4}$-alkenyl, $C_{2-4}$-alkynyl, $C_{1-3}$-alkyl-O, $C_{1-3}$-alkyl-S, a $C_{1-3}$-alkyl or $C_{1-3}$-alkyl-O— group wherein each methylene group is substituted by up to two fluorine atoms and each methyl group is substituted by up to three fluorine atoms, $R^{3.2}$ denotes
(a) H,
F, Cl, Br, H$_2$N, $(C_{1-4}$-alkyl)-NH, $(C_{1-4}$-alkyl)$_2$N, $(C_{1-3}$-alkyl)-C(O)—NH, —OH,
$C_{1-4}$-alkyl,
a $C_{1-3}$-alkyl or $C_{1-3}$-alkyl-O— group wherein each methylene group is substituted by up to two fluorine atoms and each methyl group is substituted by up to three fluorine atoms, $R^{3.3}$ denotes
(a) H,
(b) F, Cl, Br, H$_2$N, $(C_{1-4}$-alkyl)-NH, $(C_{1-4}$-alkyl)$_2$N, $(C_{1-3}$-alkyl)-C(O)—NH, —OH,
(c) $C_{1-4}$-alkyl,
(d) a $C_{1-3}$-alkyl or $C_{1-3}$-alkyl-O— group wherein each methylene group is substituted by up to two fluorine atoms and each methyl group is substituted by up to three fluorine atoms, $R^{3.2}$ and $R^{3.3}$ together with the carbon atoms to which they are attached form a monounsaturated 5-membered or a mono- or diunsaturated 6-membered heterocyclic group or a 5- to 6-membered heteroaryl group, wherein
the heterocycles mentioned previously may contain a carbonyl, thiocarbonyl or cyanoimino group adjacent to a nitrogen atom, and
may optionally be additionally substituted at one or two nitrogen atoms by a group $R^{3.3.3}$ in each case and
may optionally be additionally substituted at one or two carbon atoms by one or two groups $R^{3.3.4}$ in each case, $R^{3.3.3}$ independently of one another denote
$C_{1-4}$-alkyl or
$C_{3-6}$-cycloalkyl, $R^{3.3.4}$ independently of one another denote
$C_{1-4}$-alkyl, $C_{3-6}$-cycloalkyl,
halogen, CN, $C_{1-3}$-alkyl-O—, —NH$_2$,
a $C_{1-3}$-alkyl or $C_{1-3}$-alkyl-O— group wherein each methylene group is substituted by up to two fluorine atoms and each methyl group is substituted by up to three fluorine atoms, and $R^{3.4}$ denotes H or F, or a tautomer or salt thereof.

11. A compound of the formula I according to claim 1, wherein
$R^3$ denotes a group of the formula

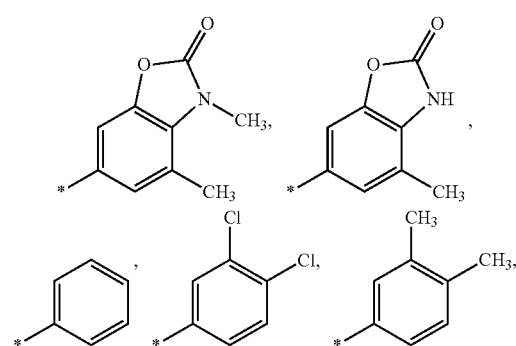

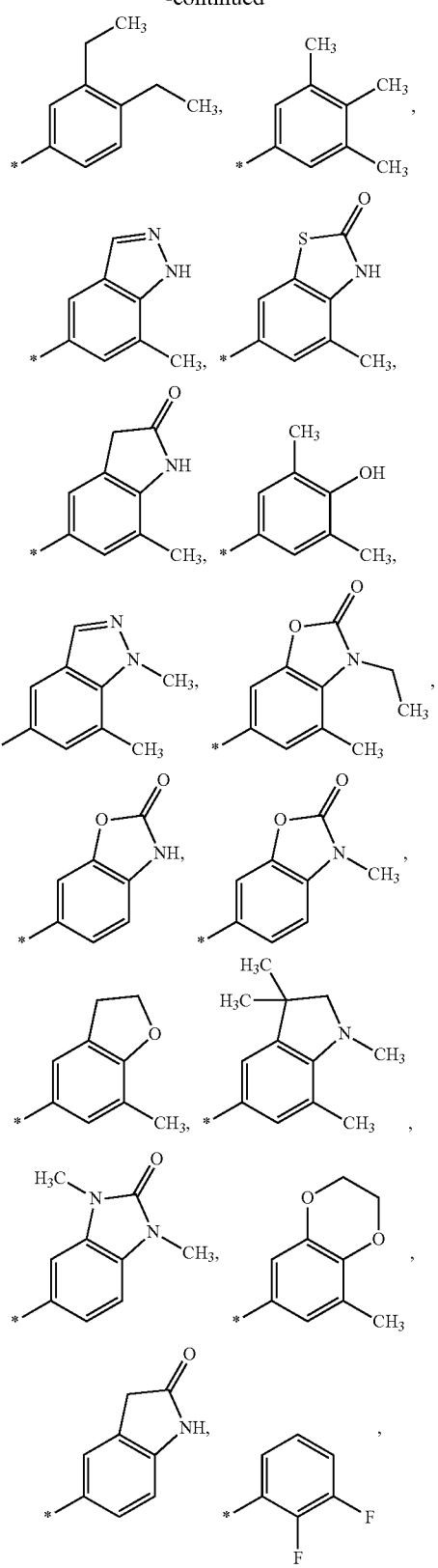

or a tautomer or salt thereof.

12. A compounds of the formula I according to claim 1, wherein $R^3$ denotes a group of the formula IVb

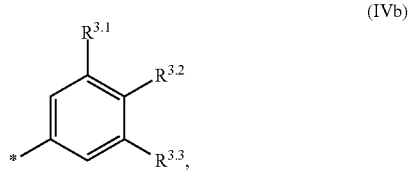

(IVb)

$R^{3.1}$ denotes
   (a) H,
   F, Cl, Br, —NH$_2$, C$_{1-3}$-alkyl-NH, (C$_{1-3}$-alkyl)$_2$N, C$_{1-3}$-alkyl-C(O)—NH, —CN, —OH,
   C$_{1-4}$-alkyl, C$_{2-4}$-alkenyl, C$_{2-4}$-alkynyl, C$_{1-3}$-alkyl-O, C$_{1-3}$-alkyl-S,
   a C$_{1-3}$-alkyl or C$_{1-3}$-alkyl-O— group wherein each methylene group is substituted by up to two fluorine atoms and each methyl group is substituted by up to three fluorine atoms,
$R^{3.2}$ and $R^{3.3}$ together with the carbon atoms to which they are bound form a monounsaturated 5-membered heterocyclic group or a mono- or diunsaturated 6-membered heterocyclic group or a 5- to 6-membered heteroaryl group, wherein
   the previously mentioned heterocycles contain a carbonyl, thiocarbonyl or cyanimino group adjacent to a nitrogen atom, and
   may each optionally additionally be substituted at one or two nitrogen atoms by a group $R^{3.3.3}$ and
   may each optionally additionally be substituted at one or two carbon atoms by one or two groups $R^{3.3.4}$,
$R^{3.3.3}$ independently of one another denote
   C$_{1-4}$-alkyl or
   C$_{3-6}$-cycloalkyl, and
$R^{3.3.4}$ independently of one another denote
   C$_{1-4}$-alkyl, C$_{3-6}$-cycloalkyl,
   halogen, —CN, —O—C$_{1-3}$-alkyl, —NH$_2$,
   a C$_{1-3}$-alkyl or C$_{1-3}$-alkyl-O— group wherein each methylene group is substituted by up to two fluorine atoms and each methyl group is substituted by up to three fluorine atoms,
or a tautomer or salt thereof.

13. A compounds of the formula I according to claim 1, wherein
$R^3$ denotes a group of the formula IVb

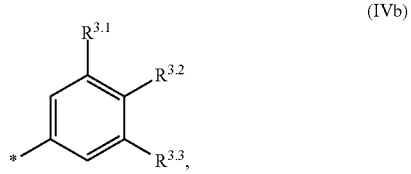

(IVb)

$R^{3.1}$ denotes
   (a) H,
   F, Cl, Br, —NH$_2$, C$_{1-3}$-alkyl-NH, (C$_{1-3}$-alkyl)$_2$N, C$_{1-3}$-alkyl-C(O)—NH, —CN, —OH,
   C$_{1-4}$-alkyl, C$_{2-4}$-alkenyl, C$_{2-4}$-alkynyl, C$_{1-3}$-alkyl-O, C$_{1-3}$-alkyl-S,
   a C$_{1-3}$-alkyl or C$_{1-3}$-alkyl-O— group wherein each methylene group is substituted by up to two fluorine atoms and each methyl group is substituted by up to three fluorine atoms, $R^{3.2}$ and $R^{3.3}$ together with the carbon atoms to which they are bound form a monounsaturated 5-membered heterocyclic group or a 5-membered heteroaryl group, wherein the previously mentioned heterocycles contain a carbonyl, thiocarbonyl or cyanimino group adjacent to a nitrogen atom, and may each optionally additionally be substituted at one or two nitrogen atoms by a group $R^{3.3.3}$ and may each optionally additionally be substituted at one or two carbon atoms by one or two groups $R^{3.3.4}$, $R^{3.3.3}$ independently of one another denote
(a) $C_{1-4}$-alkyl or
(b) $C_{3-6}$-cycloalkyl, and $R^{3.3.4}$ independently of one another denote
(a) $C_{1-4}$-alkyl, $C_{3-6}$-cycloalkyl,
(b) halogen, —CN, —O—$C_{1-3}$-alkyl, —$NH_2$,
(c) a $C_{1-3}$-alkyl or $C_{1-3}$-alkyl-O— group wherein each methylene group is substituted by up to two fluorine atoms and each methyl group is substituted by up to three fluorine atoms, or a tautomer or salt thereof.

14. A compounds of the formula I according to claim 1, wherein $R^3$ denotes a group of the formula IVc

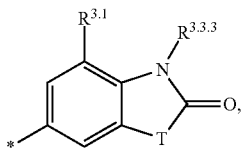

(IVc)

T denotes O, S, $CH_2$, NH or N—$R^{3.3.3}$, $R^{3.1}$ denotes
(a) H,
(b) F, Cl, Br, —$NH_2$, $C_{1-3}$-alkyl-NH, $(C_{1-3}$-alkyl$)_2$N, $C_{1-3}$-alkyl-C(O)—NH, —CN, —OH,
(c) $C_{1-4}$-alkyl, $C_{2-4}$-alkenyl, $C_{2-4}$-alkynyl, $C_{1-3}$-alkyl-O, $C_{1-3}$-alkyl-S,
(d) a $C_{1-3}$-alkyl or $C_{1-3}$-alkyl-O— group wherein each methylene group is substituted by up to two fluorine atoms and each methyl group is substituted by up to three fluorine atoms, and $R^{3.3.3}$ independently of one another denote
(a) $C_{1-4}$-alkyl or
(b) $C_{3-6}$-cycloalkyl, or a tautomer or salt thereof.

15. A compounds of the formula I according to claim 1, wherein $R^3$ denotes a group of the formula

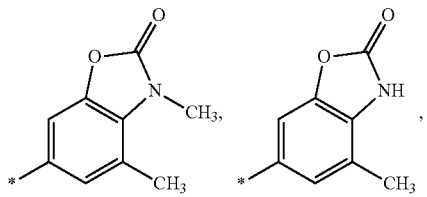

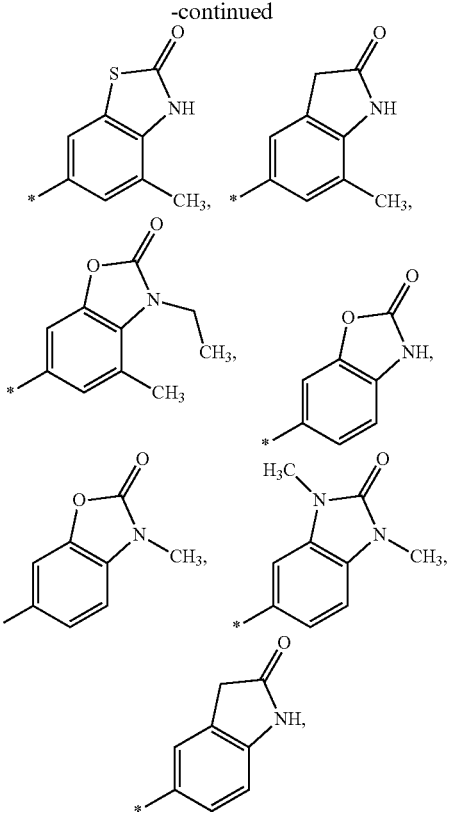

or a tautomer or salt thereof.

16. A compound of the formula I according to claim 1, wherein

U—V—X denotes
—N=(C—$R^5$)—N=, —N=(C—$R^5$)—(C—$R^6$)=,
—(C$R^4$)=(C—$R^5$)—N=, and $R^4$ denotes
(a) H,
(b) a $C_{1-6}$-alkyl or $C_{1-3}$-alkyl-O— group which is substituted in each case by a group $R^{4.1}$,
(c) $R^{4.2}R^{4.3}$N, $R^{4.2}R^{4.3}$N—$C_{1-3}$-alkylene,
(d) halogen, —CN, —OH, —COOH, $C_{1-3}$-alkyl-O, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
(e) a $C_{1-3}$-alkyl or $C_{1-3}$-alkyl-O— group wherein each methylene group is substituted by up to two fluorine atoms and each methyl group is substituted by up to three fluorine atoms, $R^{4.1}$ denotes H, OH or —O—$CH_3$,
$R^{4.2}$ denotes H or $C_{1-3}$-alkyl,
$R^{4.3}$ denotes H or $C_{1-3}$-alkyl, or
$R^{4.2}$ and $R^{4.3}$ together with the nitrogen atom to which they are bound denote a 3- to 6-membered heterocyclic group, $R^5$ denotes
(a) H,
(b) a $C_{1-6}$-alkyl or $C_{1-3}$-alkyl-O— group which is substituted by a group $R^{5.1}$ in each case,
(c) —$NR^{5.2}R^{5.3}$, $NR^{5.2}R^{5.3}$—$C_{1-3}$-alkylene,
(d) halogen, —CN, —OH, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
(e) aryl-$C_{0-3}$-alkylen-O— group, (f) a $C_{1-3}$-alkyl or $C_{1-3}$-alkyl-O— group wherein each methylene group is substituted by up to two fluorine atoms and each methyl group is substituted by up to three fluorine atoms, $R^{5.1}$ denotes H, OH or —O—CH$_3$,
$R^{5.2}$ denotes H or $C_{1-6}$-alkyl,
$R^{5.3}$ denotes H, $C_{1-6}$-alkyl or —SO$_2$—$C_{1-3}$-alkyl
$R^6$ denotes
(a) H,
(b) a $C_{1-6}$-alkyl or $C_{1-3}$-alkyl-O— group which is substituted in each case by a group $R^{6.1}$,
(c) $R^{6.2}R^{6.3}N$, $R^{6.2}R^{6.3}N$—$C_{1-3}$-alkylene,
(d) halogen, —CN, —OH, —COOH, $C_{1-3}$-alkyl-O, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
(e) a $C_{1-3}$-alkyl or $C_{1-3}$-alkyl-O— group wherein each methylene group is substituted by up to two fluorine atoms and each methyl group is substituted by up to three fluorine atoms, $R^{6.1}$ denotes H, OH or —O—CH$_3$,
$R^{6.2}$ denotes H or $C_{1-3}$-alkyl,
$R^{6.3}$ denotes H or $C_{1-3}$-alkyl, or
$R^{6.2}$ and $R^{6.3}$ together with the nitrogen atom to which they are bound denote a 3- to 6-membered heterocyclic group, or a tautomer or salt thereof.

17. A compound of the formula I according to claim 1, wherein the ring

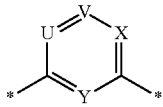

denotes a group of the formula

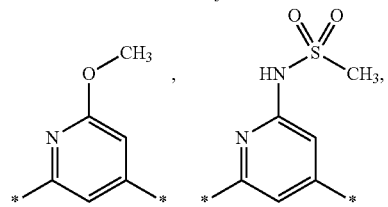
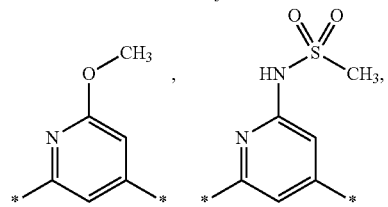

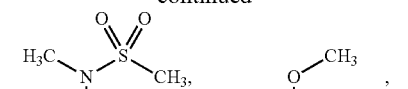
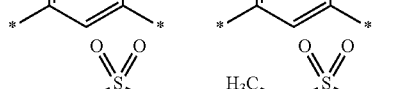
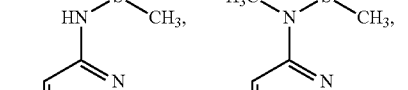
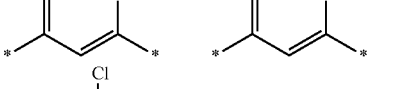
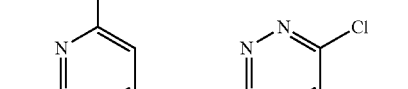
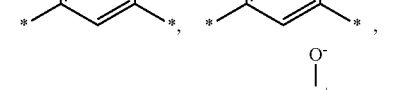
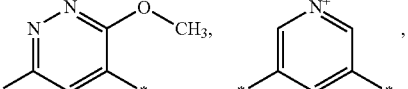
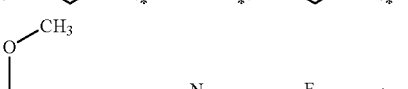
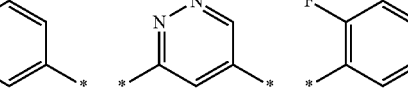
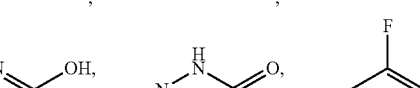
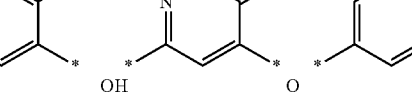
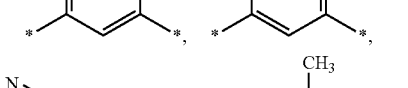
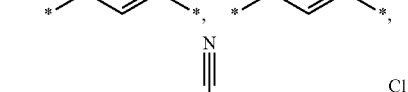
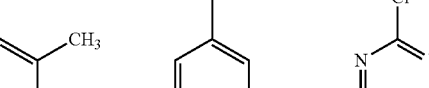
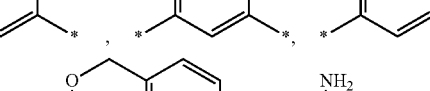
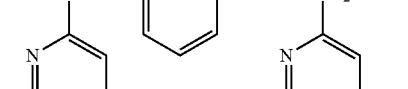

-continued
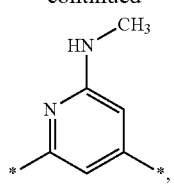
or a tautomer or salt thereof.
18. A compounds of the formula I according to claim 1, wherein
R¹ denotes a group of the formula
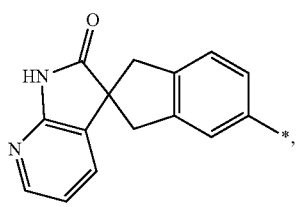
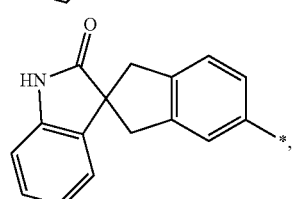
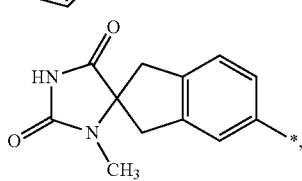
R² denotes H,
R₃ denotes a group of the formula
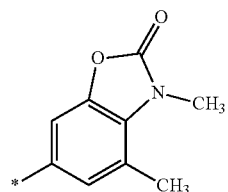
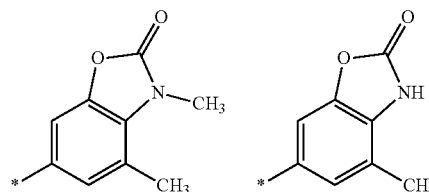
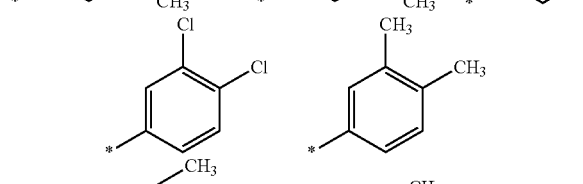
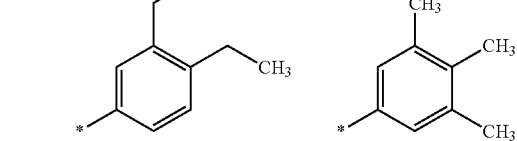
-continued
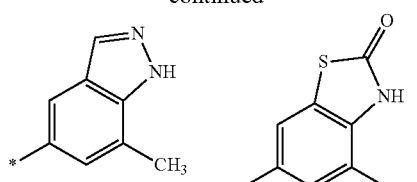
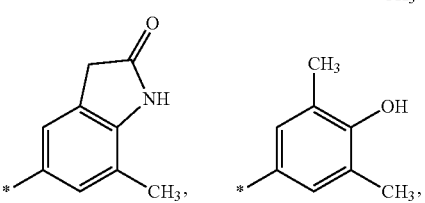
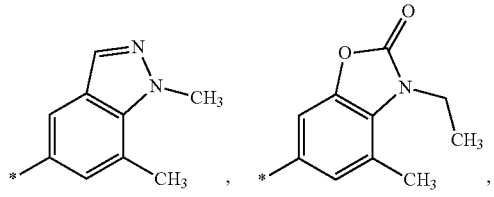
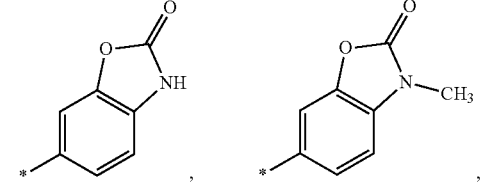
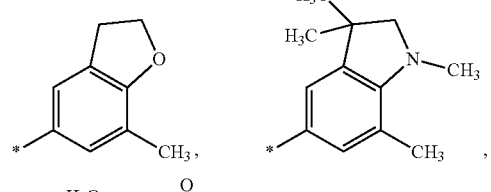
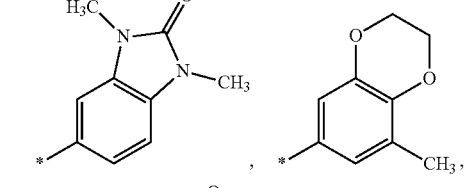
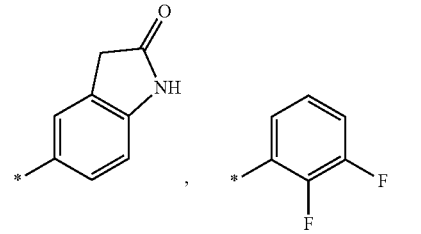
the ring
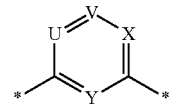

denotes a group selected from
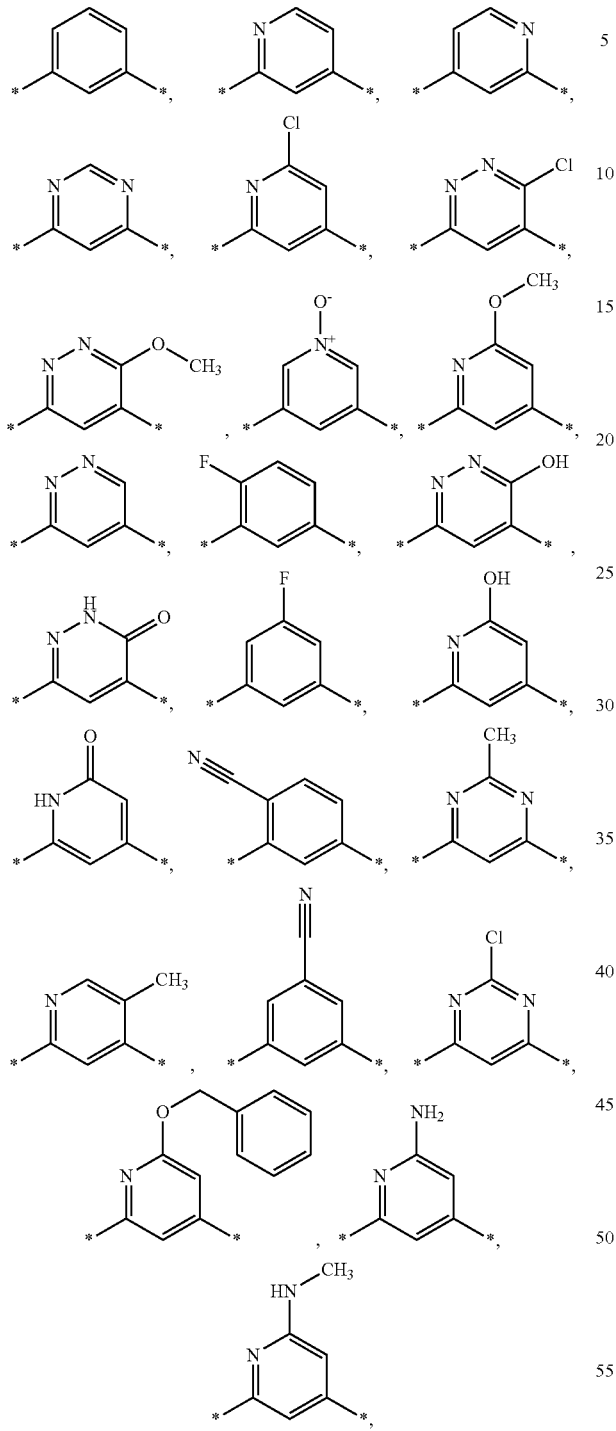
or a tautomer or salt thereof.
19. A compound of the formula I according to claim 1, wherein
R¹ and R² together with the nitrogen atom to which they are bound denote a group of the formula
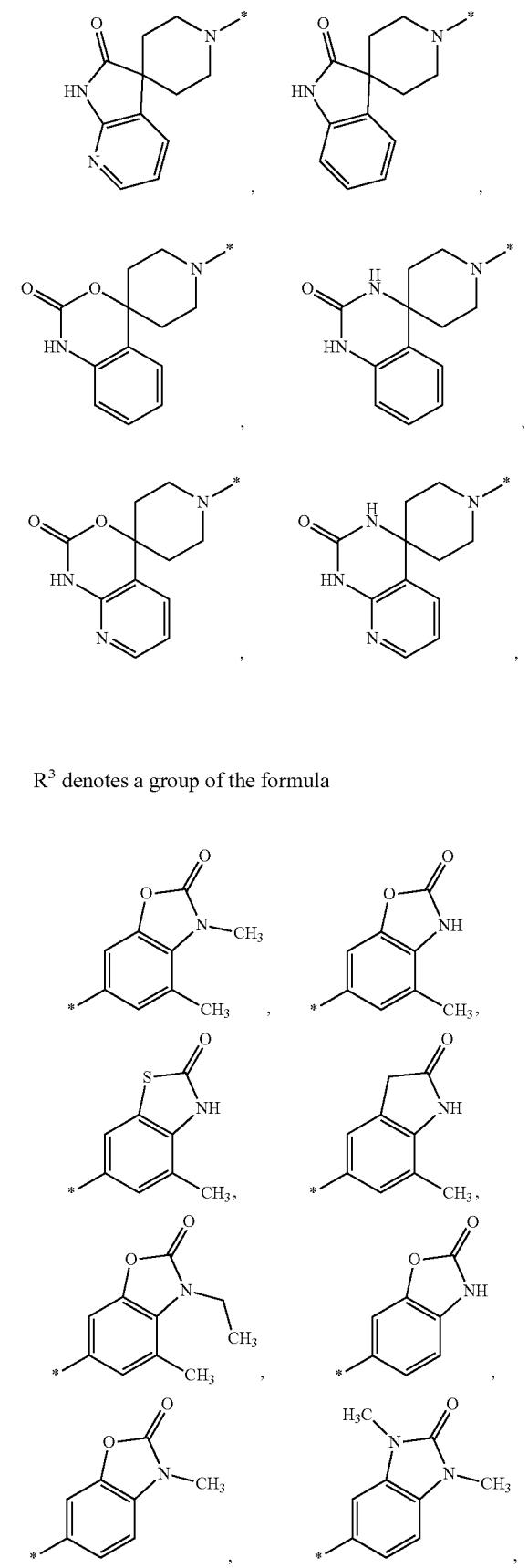
$R^3$ denotes a group of the formula 91
-continued
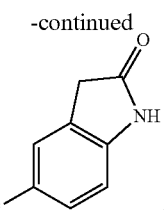
and the ring
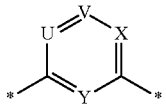
denotes a group selected from
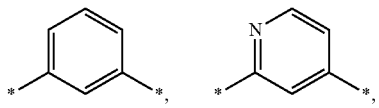
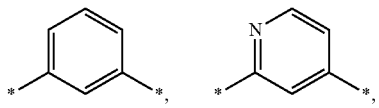
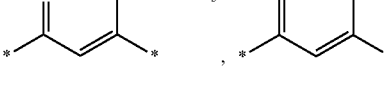
92
-continued
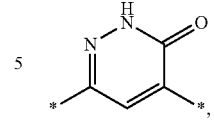
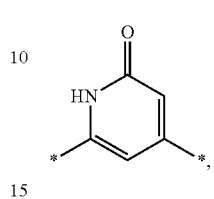
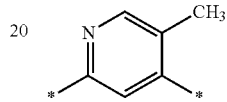
or a tautomer or salt thereof.
20. A compound according to claim 1 selected from the group consisting of:
| No. | Structure |
|---|---|
| (1) | 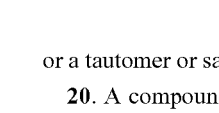 |

| No. | Structure |
|---|---|
| (2) | 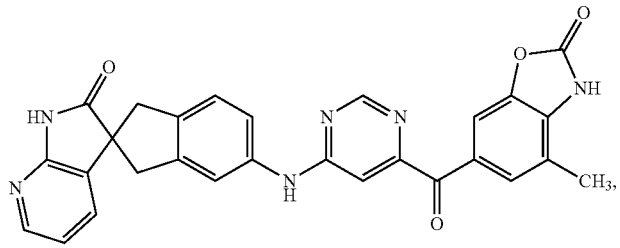 [SMILES: Cc1cc(C(=O)c2cc(Nc3ccc4c(c3)CC3(C4)C(=O)Nc4ncccc43)ncn2)cc2oc(=O)[nH]c12] |
| (3) | 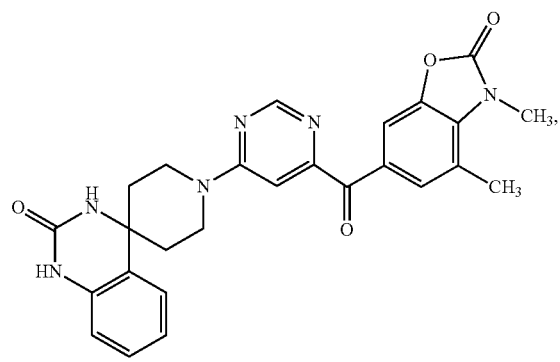 [SMILES: Cc1cc(C(=O)c2cc(N3CCC4(CC3)NC(=O)Nc3ccccc34)ncn2)cc2oc(=O)n(C)c12] |
| (4) | 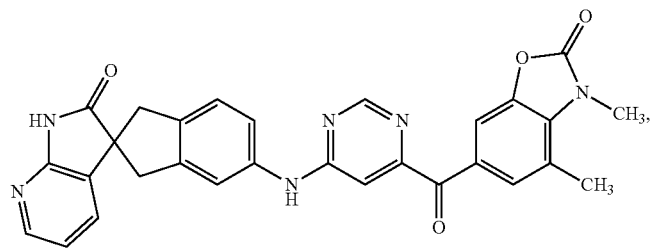 [SMILES: Cc1cc(C(=O)c2cc(Nc3ccc4c(c3)CC3(C4)C(=O)Nc4ncccc43)ncn2)cc2oc(=O)n(C)c12] |
| (5) | 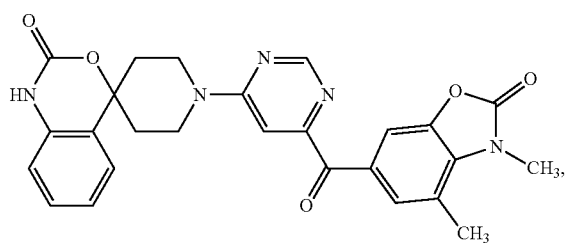 [SMILES: Cc1cc(C(=O)c2cc(N3CCC4(CC3)OC(=O)Nc3ccccc34)ncn2)cc2oc(=O)n(C)c12] |
| (6) | 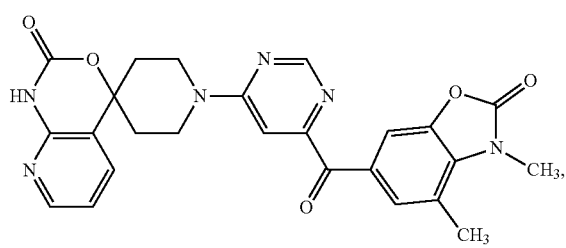 [SMILES: Cc1cc(C(=O)c2cc(N3CCC4(CC3)OC(=O)Nc3ncccc34)ncn2)cc2oc(=O)n(C)c12] |

| No. | Structure |
|---|---|
| (7) | 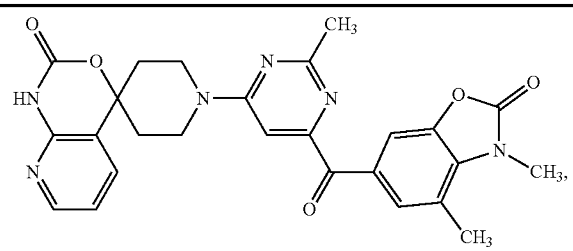 |
| (8) | 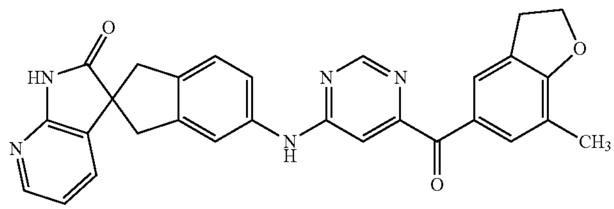 |
| (9) | | or a tautomer or salt thereof.

21. A physiologically acceptable salt of a compound according to any one of claims 1 to 20.

22. A pharmaceutical composition comprising a compound according to any one of claims 1 to 20, or a physiologically acceptable salt thereof and a carrier or diluent.

23. A method of treating headache, migrain headache or cluster headache which method comprises administering to a host in need of such treatment a therapeutically effective amount of a compound according to any one of claims 1 to 20, or a physiologically acceptable salt thereof.

* * * * *